US011084781B2

(12) United States Patent
Zhang et al.

(10) Patent No.: US 11,084,781 B2
(45) Date of Patent: Aug. 10, 2021

(54) DIARYLUREAS AS CB1 ALLOSTERIC MODULATORS

(71) Applicant: Research Triangle Institute, Research Triangle Park, NC (US)

(72) Inventors: Yanan Zhang, Apex, NC (US); Thuy Nguyen, Morrisville, NC (US); Nadezhda German, Amarillo, TX (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 16/612,680

(22) PCT Filed: May 10, 2018

(86) PCT No.: PCT/US2018/031977
§ 371 (c)(1),
(2) Date: Nov. 11, 2019

(87) PCT Pub. No.: WO2018/209030
PCT Pub. Date: Nov. 15, 2018

(65) Prior Publication Data
US 2020/0062699 A1    Feb. 27, 2020

Related U.S. Application Data

(60) Provisional application No. 62/505,383, filed on May 12, 2017.

(51) Int. Cl.
| | | |
|---|---|---|
| *C07C 275/38* | (2006.01) |
| *C07D 205/04* | (2006.01) |
| *C07D 207/335* | (2006.01) |
| *C07D 211/38* | (2006.01) |
| *C07D 213/643* | (2006.01) |
| *C07D 215/12* | (2006.01) |
| *C07D 239/26* | (2006.01) |
| *C07D 295/135* | (2006.01) |
| *C07D 333/20* | (2006.01) |
| *C07D 487/08* | (2006.01) |
| *C07D 491/107* | (2006.01) |
| *A61P 25/30* | (2006.01) |

(52) U.S. Cl.
CPC ............ *C07C 275/38* (2013.01); *A61P 25/30* (2018.01); *C07D 205/04* (2013.01); *C07D 207/335* (2013.01); *C07D 211/38* (2013.01); *C07D 213/643* (2013.01); *C07D 215/12* (2013.01); *C07D 239/26* (2013.01); *C07D 295/135* (2013.01); *C07D 333/20* (2013.01); *C07D 487/08* (2013.01); *C07D 491/107* (2013.01)

(58) Field of Classification Search
CPC . C07C 2603/18; C07C 275/28; C07C 275/30; C07C 275/32; C07C 275/38
See application file for complete search history.

(56) References Cited

U.S. PATENT DOCUMENTS

| | | | |
|---|---|---|---|
| 6,093,742 A | 7/2000 | Salituro et al. | |
| 2005/0154230 A1* | 7/2005 | Yura | C07D 317/58 564/52 |
| 2009/0239841 A1* | 9/2009 | Hutchison | A61P 19/08 514/214.02 |
| 2011/0118234 A1 | 5/2011 | Biswas et al. | |

FOREIGN PATENT DOCUMENTS

| | | |
|---|---|---|
| CN | 104744350 A | 7/2015 |
| KR | 101332830 B1 | 11/2013 |
| WO | 2006018662 A2 | 2/2006 |
| WO | 2006049941 A2 | 5/2006 |

OTHER PUBLICATIONS

Supplementary European Search Report for EP 18 79 8464, dated Dec. 18, 2020.
Gelfand, E.V. et al., "Rimonabant: A cannabinoid receptor type 1 blocker for management of multiple cardiometabolic risk factors", Journal of the American College of Cardiology (2006), vol. 47, No. 10, pp. 1919-1926.
Nguyen, T., et al., "Novel diarylurea based allosteric modulators of the cannabinoid CB1 receptor: evaluation of importance of 6-pyrrolidinylpyridinyl substitution", Journal of Medicinal Chemistry (Aug. 18, 2017), vol. 60, No. 17, pp. 7410-7424.
Chemical Abstract compound, STN express, RN 892457-95-3, entered Jul. 13, 2006.
Bioorganic & Medicinal Chemistry, 2015, vol. 23, No. 13, pp. 3228-3236.
International Search Report for PCT/US2018/031977, dated Aug. 31, 2018.
Chemical Abstract compound, STN express, RN 1026403-10-0, entered Jun. 8, 2008.
Chemical Abstract compound, STN express, RN 1905905-60-3, entered May 8, 2016.

\* cited by examiner

*Primary Examiner* — Valerie Rodriguez-Garcia
(74) *Attorney, Agent, or Firm* — Barnes & Thornburg LLP

(57) ABSTRACT

The present invention provides novel diarylurea derivatives (compounds of formula (I)) and their uses. The compounds of the present invention are demonstrated to be allosteric modulators of the CB1 receptor, and therefore useful for the treatment of diseases and conditions mediated by CB1.

25 Claims, 2 Drawing Sheets

DIARYLUREAS AS CB1 ALLOSTERIC MODULATORS

CROSS-REFERENCE TO RELATED APPLICATIONS

This patent application is a National Stage application of International Application No. PCT/US2018/031977, filed May 10, 2018, which claims the benefit of United States Provisional Patent Application No. 62/505,383, filed May 12, 2017, which is herein incorporated by reference in its entirety.

FEDERALLY SPONSORED RESEARCH

This invention was made with government support under DA040693 which was awarded by the National Institutes of Health. The government has certain rights in the invention.

FIELD OF THE INVENTION

The present invention provides novel cannabinoid CB1 receptor allosteric modulator compounds and uses therefor. The compounds of the present invention are believed to be useful for the treatment of diseases and conditions caused by physiological processes implicating the cannabinoid CB1 receptor including appetite control, cardiovascular regulation, metabolic syndromes, pain regulation, learning and memory, and drug dependence.

BACKGROUND OF THE INVENTION

The 2014 National Survey on Drug Use and Health (NSDUH) reports that 45 millions Americans aged 12 and older reported having used cocaine in their lifetime. In 2014, there were an estimated 1.5 million current (past-month) cocaine users aged 12 and older in the US (0.6% of the population), and about 913,000 Americans met the *Diagnostic and Statistical Manual of Mental Disorders* criteria for dependence or abuse of cocaine (in any form) during the past 12 months. The National Institute of Drug Addiction (NIDA) projected the global size of first-in-class cocaine dependence treatments at USD 1.2 billion in annual revenue. The overall market for the treatment of addiction is estimated to be USD 35 billion per year according to the Substance Abuse and Mental Health Services Administration (SAMHSA). In 2014, WHO estimated that more than 1.9 billion adults worldwide were overweight, of those over 600 million had obesity. Around 35% of the US adult population have obesity (BMI>30). (Flegal, K M. JAMA, 2012, 307(5), 491-497). Cost of obesity to healthcare systems was estimated at USD 147 billion (Finkelstein et al, Health Affairs 28, no 5, 2009, w822-831).

The cannabinoid CB1 and CB2 receptors are components of the endocannabinoid system which is involved in many important physiological processes such as cardiovascular regulation, learning and memory, appetite and pain control. See, for example, Mackie, K. Cannabinoid receptors as therapeutic targets. *Annu. Rev. Pharmacol. Toxicol.* 2006, 46, 101-122; Howlett, A. C.; Breivogel, C. S.; S. R., C.; Deadwyler, S. A.; Hampson, R. E.; Porrino, L. J. Cannabinoid physiology and pharmacology: 30 years of progress. *Neuropharmacology* 2004, 47 Suppl 1, 345-358; and Di, M.; Bisogno, T.; De Petrocellis, L. Endocannabinoids: new targets for drug development. *Curr Pharm Des* 2000, 6, 1361-80; each herein incorporated by reference with regarding to such background teaching.

Expressed abundantly in the central nervous system, CB1 receptor has been demonstrated as a viable target in a number of disorders including obesity, drug addiction, pain, inflammation, gastrointestinal diseases, multiple sclerosis, psychosis, schizophrenia, and osteoporosis. See, Pertwee, R. G. The therapeutic potential of drugs that target cannabinoid receptors or modulate the tissue levels or actions of endocannabinoids. *AAPS Journal* 2005, 7, E625-54; herein incorporated by reference with regard to such teaching. The CB2 receptor is found mainly in immune cells and is responsible for modulation of cytokine release and immune cell migration. A wide range of selective and non-selective agonists and antagonists for CB1 and CB2 receptors have been developed thus far. Currently, licensed cannabinoid medications all contain tetrahydrocannabinol ($\Delta^9$-THC), the principal psychoactive constituent of the plant *cannabis* or its synthetic analog (nabilone); however, they are prescribed with many restrictions because of their adverse effects such as marijuana-like psychoactivity and addictive tendency. The CB1 selective antagonist/inverse agonist Rimonabant (SR141716A) was first approved for treatment of obesity but was subsequently withdrawn due to a risk of suicidal ideation.

An alternate approach to target the CB1-mediated signaling pathways is to develop allosteric modulators that bind to distinct binding sites from the orthosteric site. Compared to orthosteric ligands, allosteric modulators offer benefits, such as better spatial and temporal selectivity due to their dependence on the presence of an orthosteric agonist for signaling, better subtype selectivity due to less conserved allosteric binding sites, and improved safety profiles due to "ceiling" effect. See, for example, Christopoulos, A. Allosteric binding sites on cell-surface receptors: novel targets for drug discovery. *Nat Rev Drug Discov* 2002, 1, 198-210; and Bridges, T. M.; Lindsley, C. W. G-protein-coupled receptors: from classical modes of modulation to allosteric mechanisms. *ACS Chem. Biol.* 2008, 3, 530-541; each incorporated herein with regard to such background teaching. Recently, several allosteric modulators have been advanced to the market as therapeutics, including cinacalcet (Sensipar/Mimpara; Amgen), a positive allosteric modulator (PAM) of the calcium sensing receptor (CasR, a member of the GPCR C family), and Maraviroc (Celsentri/selzentry; Pfizer), a negative allosteric modulator (NAM) of the CCR5 receptor, demonstrating that allosteric modulation can be a safe and therapeutically relevant approach to targeting GPCRs. See, for example, Harrington, P. E.; Fotsch, C. Calcium sensing receptor activators: calcimimetics. *Curr Med Chem* 2007, 14, 3027-34; Dorr, P.; Westby, M.; Dobbs, S.; Griffin, P.; Irvine, B.; Macartney, M.; Mori, J.; Rickett, G.; Smith-Burchnell, C.; Napier, C.; Webster, R.; Armour, D.; Price, D.; Stammen, B.; Wood, A.; Perros, M. Maraviroc (UK-427,857), a potent, orally bioavailable, and selective small-molecule inhibitor of chemokine receptor CCR5 with broad-spectrum anti-human immunodeficiency virus type 1 activity. *Antimicrob Agents Chemother* 2005, 49, 4721-32; Bridges, T. M.; Lindsley, C. W. G-protein-coupled receptors: from classical modes of modulation to allosteric mechanisms. *ACS Chem Biol* 2008, 3, 530-41; and Conn, P. J.; Christopoulos, A.; Lindsley, C. W. Allosteric modulators of GPCRs: a novel approach for the treatment of CNS disorders. *Nat. Rev. Drug. Discov.* 2009, 8, 41-54; each herein incorporated by reference with regard to such background teaching.

Since 2005 with the discovery of the first CB1 modulator (A) Org27569:

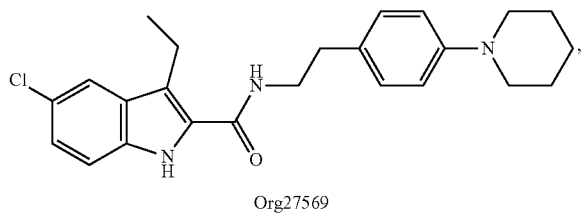 [SMILES: CCc1c(C(=O)NCCc2ccc(N3CCCCC3)cc2)[nH]c2ccc(Cl)cc12]

Org27569 several negative and positive allosteric modulators have been reported, including NAMs PSNCBAM-1 (B):

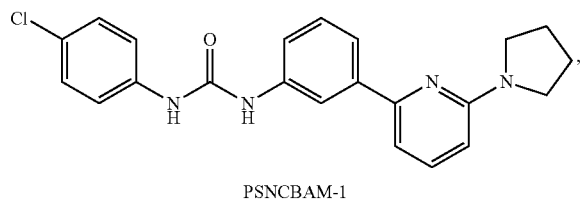 [SMILES: O=C(Nc1ccc(Cl)cc1)Nc1cccc(-c2cccc(N3CCCC3)n2)c1]

PSNCBAM-1 cannabidiol (C):

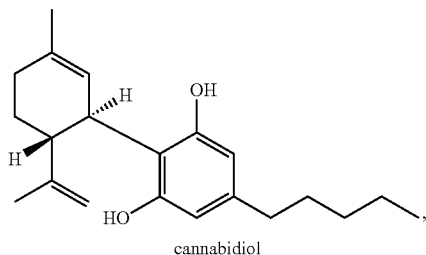 [SMILES: C=C(C)[C@@H]1CCC(C)=C[C@H]1c1c(O)cc(CCCCC)cc1O]

cannabidiol fenofibrate (D):

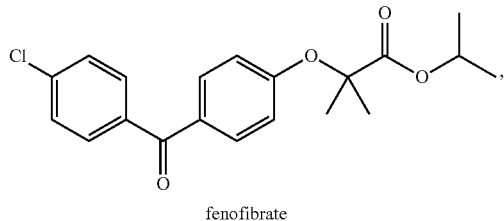 [SMILES: CC(C)OC(=O)C(C)(C)Oc1ccc(C(=O)c2ccc(Cl)cc2)cc1]

fenofibrate and PAMs such as ZCZ011 (E):

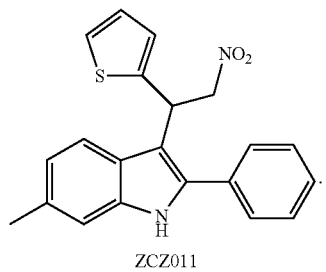 [SMILES: Cc1ccc2c(C(C[N+](=O)[O-])c3cccs3)c(-c3ccccc3)[nH]c2c1]

ZCZ011

A and B are two small molecule CB1 NAMs that have been more extensively characterized among them. Both were reported to enhance radioligand binding levels but decrease responses stimulated by orthosteric agonists in assays such as intracellular calcium mobilization, [$^{35}$S]GTP-γ-S binding, cAMP, and 3-arrestin recruitment. Unlike A, which displays agonist activities in some assays such as ERK, B showed little or no activity in the absence of an orthosteric agonist in the many assays investigated thus far. See, Horswill, J.; Bali, U.; Shaaban, S.; Keily, J.; Jeevaratnam, P.; Babbs, A.; Reynet, C.; In, P. W. K. PSNCBAM-1, a novel allosteric antagonist at cannabinoid CB1 receptors with hypophagic effects in rats. *Br J Pharmacol* 2007, 152, 805-814; Laprairie, R. B.; Bagher, A. M.; Kelly, M. E.; Denovan-Wright, E. M. Cannabidiol is a negative allosteric modulator of the type 1 cannabinoid receptor. *Br J Pharmacol* 2015, 172, 4790-4805; Priestley, R. S. N., Sarah A.; Alexander, Stephen P. H.; Kendall, David A. A potential role for cannabinoid receptors in the therapeutic action of fenofibrate. *FASEB J* 2015, 29, 1446-1455; Ignatowska-Jankowska, B. M.; Baillie, G. L.; Kinsey, S.; Crowe, M.; Ghosh, S.; Owens, R. A.; Damaj, I. M.; Poklis, J.; Wiley, J. L.; Zanda, M.; Zanato, C.; Greig, I. R.; Lichtman, A. H.; Ross, R. A. A Cannabinoid CB1 Receptor-Positive Allosteric Modulator Reduces Neuropathic Pain in the Mouse with No Psychoactive Effects. *Neuropsychopharmacol* 2015, 40, 2948-2959; Baillie, G. L.; Horswill, J. G.; Anavi-Goffer, S.; Reggio, P. H.; Bolognini, D.; Abood, M. E.; McAllister, S.; Strange, P. G.; Stephens, G. J.; Pertwee, R. G.; Ross, R. A. CB1 Receptor Allosteric Modulators Display Both Agonist and Signaling Pathway Specificity. *Mol Pharmacol* 2013, 83, 322-338; and Khajehali, E.; Malone, D. T.; Glass, M.; Sexton, P. M.; Christopoulos, A.; Leach, K. Biased agonism and biased allosteric modulation at the CB1 cannabinoid receptor. *Mol Pharmacol* 2015, 88, 368-379; each incorporated herein with regard to such background teaching. For recent review on this topic, see, Nguyen, T.; Li, J. X.; Thomas, B. F.; Wiley, J. L.; Kenakin, T. P.; Zhang, Y. Allosteric Modulation: An Alternate Approach Targeting the Cannabinoid CB1 Receptor. *Med Res Rev* 2017, 37, 441-474;

The cannabinoid CB 1 receptor has been implicated to have important roles in many conditions such as drug addiction, pain, obesity, inflammation, anxiety and depression. Albeit demonstrating clinical effects in obesity treatment and smoke cessation in humans, the CB1 selective antagonist/inverse agonist known as SR141716A, Rimonabant, Acomplia, and Zilmulti:

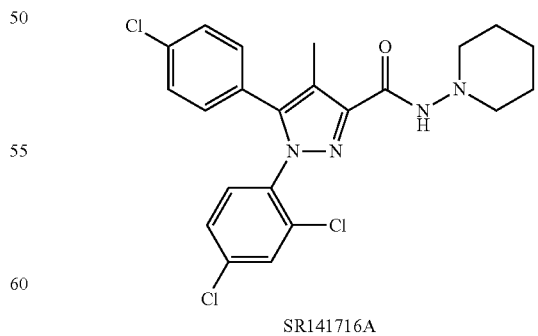

SR141716A was withdrawn from the European market due to an associated risk of suicidal ideation. Therefore, an alternate approach to target CB1 pathway by an allosteric modulator has emerged as a promising strategy to modulate the therapeutically valued CB1 receptor while avoiding side effects of orthosteric antagonists/inverse agonists.

A recent examination of national trend data has raised an alarm in rising cocaine-related overdose death in association with concurrent opioid abuse. Currently, there are no FDA approved medications for the treatment of cocaine addiction, the relapse rate of which remains as high as 40 to 60%. With the in vivo efficacy to attenuate reinstatement of cocaine craving, these CB1 allosteric modulators may represent promising candidates for the development of therapeutics for relapse prevention of cocaine addiction and abuse, an urgent need that is currently unfilled. See, for example, McCall Jones, C.; Baldwin, G. T.; Compton, W. M. Recent Increases in Cocaine-Related Overdose Deaths and the Role of Opioids. *Am J Public Health* 2017, 107, 430-432; and McLellan, A. T.; Lewis, D. C.; O'Brien, C. P.; Kleber, H. D. Drug dependence, a chronic medical illness: implications for treatment, insurance, and outcomes evaluation. *JAMA* 2000, 284, 1689-95; each incorporated herein by reference with regard to such background teaching.

BRIEF SUMMARY OF THE INVENTION

The present invention describes the development of diarylureas as CB1 negative allosteric modulators. Compared to PSNCBAM-1, (B) illustrated herein above, the present compounds show good pharmacokinetic properties, similar in vitro potency, and greater potency in attenuating drug-induced reinstatement of extinguished cocaine seeking behavior of rats, which have been previously trained to self-administer this drug. The compounds of the present invention demonstrate efficacy in an in vivo model of drug addiction.

The compounds of the present invention act on the same biological target as the afore-mentioned compounds. Antagonism of the CB1 receptor signaling has been clinically demonstrated to be effective for obesity treatment as exemplified by Rimonabant. Furthermore, Rimonabant also reduced resumption of cocaine-seeking response and smoking habit, as well as inhibited the atrophic and psychoactive effects of marijuana. By allosterically modulating the CB1 receptor, the present compounds have the potential therapeutic value of Rimonabant, while avoiding its untoward effects. The present compounds could also be of great value to obese patients with addiction problems.

One embodiment of the present invention includes a compound of Formula (I)

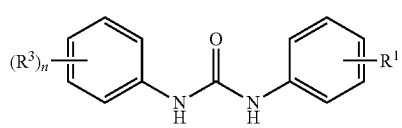

(I)

wherein:
$R^1$ is O—($C_{1-6}$ alkyl), O-(5- to 13-membered cycloalkyl), $N(R^2)_2$, $(C_{1-8} alkyl)_x$-(5- to 13-membered aryl), $(C_{1-8} alkyl)_x$-(5- to 13-membered heteroaryl), or $(C_{1-8} alkyl)_x$-(4- to 13-membered heterocyclyl), wherein each of aryl, heteroaryl, and heterocyclyl is optionally substituted with one or more of:
$R^2$,
$OR^2$,
$C(O)R^2$,
$C(O)OR^2$,
$NO_2$,
halogen, or
$C_{1-6}$ haloalkyl;
$R^2$ is H, $C_{1-6}$ alkyl, $C_{1-6}$ alkenyl, $C_{1-6}$ alkynyl, or 5- to 13-membered aryl;
$R^3$ is H, $C_{1-6}$ alkyl, $C_{1-6}$ alkenyl, $C_{1-6}$ alkynyl, halogen, $C_{1-6}$ haloalkyl, $NO_2$, or CN;
each x independently is 0 or 1; and
n is 1, 2, or 3;
or a pharmaceutically acceptable salt or solvate thereof.

One embodiment of the present invention provides a compound wherein n is 1. One aspect of the embodiment provides $R^3$ is halogen or cyano. One aspect of the embodiment provides $R^3$ is Cl.

One embodiment of the present invention provides $R^1$ is 5- to 13-membered aryl, optionally substituted with one or more $R^2$. One aspect of the embodiment provides wherein $R^1$ is phenyl, optionally substituted with one or more $R^2$. One aspect of the embodiment provides $R^1$ is unsubstituted phenyl. Another aspect of the embodiment provides $R^1$ is phenyl substituted with one $R^2$. One aspect of the embodiment provides $R^1$ is phenyl substituted with two $R^2$. One aspect of the embodiment provides $R^2$ is halogen.

One embodiment of the present invention provides $R^1$ is 5- to 13-membered heteroaryl, optionally substituted with one or more $R^2$. One aspect of the embodiment provides $R^1$ is furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzoxazole, benzothiophene, indole, indazole, benzimidazole, imidazopyridine, pyrazolopyridine, and pyrazolopyrimidine, each optionally substituted with one or more $R^2$. One aspect of the embodiment provides $R^1$ is pyridine, optionally substituted with one or more $R^2$. One aspect of the embodiment provides $R^1$ is thiophene, optionally substituted with one or more $R^2$. One aspect of the embodiment provides $R^1$ is azetidine, optionally substituted with one or more $R^2$.

One embodiment of the present invention provides x is 0.

One embodiment of the present invention provides a method for the treatment of a disease in a mammal susceptible to blockade of the CB1 receptor which comprises administration of an effective amount of a compound of the present invention. One aspect of the embodiment provides wherein the disease is withdrawal, drug dependence, smoking cessation, addiction, opioid addiction, cocaine addiction, relapse of cocaine addiction, tobacco addiction, alcohol addiction, inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, pain, chronic pain, acute pain, somatic pain, visceral pain, neuropathic pain, inflammatory pain, infertility, memory loss, cognitive dysfunction, Alzheimer's Disease, Tourette's Syndrome, dyskinesia, tardive dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss.

One embodiment of the present invention is a pharmaceutical composition comprising a compound of the present invention and one or more pharmaceutically acceptable carrier.

One embodiment of the present invention is the use of a compound of the present invention for the preparation of a medicament for the treatment of a disease in a mammal susceptible to blockade of CB1 which comprises administration of an effective amount of the compound. One aspect of the embodiment provides wherein the disease is withdrawal, drug dependence, smoking cessation, addiction, opioid addiction, cocaine addiction, relapse of cocaine addiction, tobacco addiction, alcohol addiction, inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, pain, chronic pain, acute pain, somatic pain, visceral pain, neuropathic pain, inflammatory pain, infertility, memory loss, cognitive dysfunction, Alzheimer's Disease, Tourette's Syndrome, dyskinesia, tardive dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss.

One embodiment of the present invention provides a compound of the present invention for use as an active therapeutic substance.

One embodiment of the present invention provides a compound of the present invention for use in the treatment of a disease mediated by CB1. One aspect of the embodiment provides wherein the disease is withdrawal, drug dependence, smoking cessation, addiction, opioid addiction, cocaine addiction, relapse of cocaine addiction, tobacco addiction, alcohol addiction, inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, pain, chronic pain, acute pain, somatic pain, visceral pain, neuropathic pain, inflammatory pain, infertility, memory loss, cognitive dysfunction, Alzheimer's Disease, Tourette's Syndrome, dyskinesia, tardive dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss.

One embodiment of the present invention provides a method for treating one or more of withdrawal, drug dependence, smoking cessation, addiction, opioid addiction, cocaine addiction, relapse of cocaine addiction, tobacco addiction, alcohol addiction, inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, pain, chronic pain, acute pain, somatic pain, visceral pain, neuropathic pain, inflammatory pain, infertility, memory loss, cognitive dysfunction, Alzheimer's Disease, Tourette's Syndrome, dyskinesia, tardive dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss comprising administering an effective amount of a compound of the present invention.

One embodiment of the present invention provides the use of a compound of the present invention for the preparation of a medicament for the treatment of one or more of withdrawal, drug dependence, smoking cessation, addiction, opioid addiction, cocaine addiction, relapse of cocaine addiction, tobacco addiction, alcohol addiction, inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, pain, chronic pain, acute pain, somatic pain, visceral pain, neuropathic pain, inflammatory pain, infertility, memory loss, cognitive dysfunction, Alzheimer's Disease, Tourette's Syndrome, dyskinesia, tardive dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss, which comprises administration of an effective amount of the compound.

One embodiment of the present invention provides a compound of the present invention for use in the treatment of one or more of withdrawal, drug dependence, smoking cessation, addiction, opioid addiction, cocaine addiction, relapse of cocaine addiction, tobacco addiction, alcohol addiction, inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, pain, chronic pain, acute pain, somatic pain, visceral pain, neuropathic pain, inflammatory pain, infertility, memory loss, cognitive dysfunction, Alzheimer's Disease, Tourette's Syndrome, dyskinesia, tardive dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss.

Preferably, the compounds of the present invention may be used where CB1 receptor agents may exhibit greater potency and experience reduced side effects, resulting in improved efficacy, pharmacokinetics, and safety.

The compounds are believed useful for the treatment of diseases and conditions caused by modulation of the CB1 receptor, but the invention should not be thereto limited.

The scope of the present invention includes all combinations of aspects, embodiments, and preferences herein described.

DETAILED DESCRIPTION OF THE INVENTION

Figure 1:
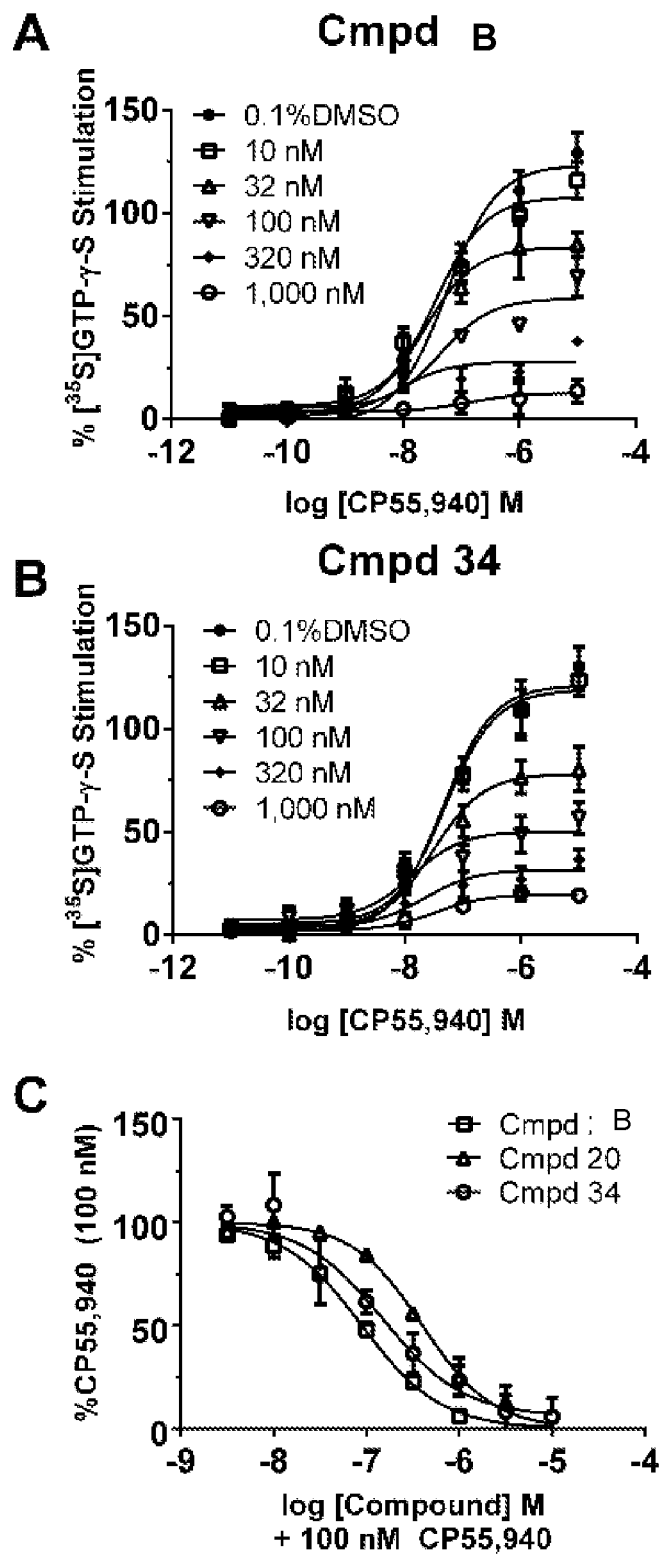
FIG. 1 is an illustration of the effects of compounds of the present invention as compared to the known Compound B, illustrating effectiveness in reducing the binding level of [$^{35}$S] GTP-γ-S activated by CP55,940. The binding levels in the presence of allosteric modulators were expressed as percentage compared to the binding level in the absence of allosteric modulators. Symbols represent mean values±S.E.M. from at least three independent experiments carried out in duplicates.

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_{x-y}$ alkyl," which refers to an alkyl group, as herein defined, containing the specified number of carbon atoms. Similar terminology will apply for other preferred terms and ranges as well. Thus, for example, $C_{1-4}$ alkyl represents a straight or branched chain hydrocarbon containing one to four carbon atoms.

As used herein the term "alkyl" alone or in combination with any other term, refers to a straight or branched chain hydrocarbon. Examples of "alkyl" as used herein include, but are not limited to, methyl, ethyl, propyl, isopropyl, isobutyl, n-butyl, tert-butyl, sec-butyl, iso-pentyl, n-pentyl, n-hexyl, and the like.

As used herein the term "alkenyl" refers to a straight or branched chain aliphatic hydrocarbon containing one or more carbon-to-carbon double bonds, which may be optionally substituted, with multiple degrees of substitution being allowed. Examples of "alkenyl" as used herein include, but are not limited to, vinyl, and allyl.

As used herein, the term "alkylene" refers to an optionally substituted straight divalent hydrocarbon radical. Examples of "alkylene" as used herein include, but are not limited to, methylene, ethylene, n-propylene, n-butylene, and the like.

As used herein the term "alkynyl" refers to a straight or branched chain aliphatic hydrocarbon containing one or more carbon-to-carbon triple bonds, which may be optionally substituted, with multiple degrees of substitution being allowed. An example of "alkynyl" as used herein includes, but is not limited to, ethynyl.

As used herein, the term "cycloalkyl" refers to a fully saturated optionally substituted monocyclic, bicyclic, bridged, or spirocyclic hydrocarbon ring, with multiple degrees of substitution being allowed. Exemplary "cycloalkyl" groups as used herein include, but are not limited to, cyclopropyl, cyclobutyl, cyclopentyl, cyclohexyl, and cycloheptyl.

As used herein, the term "heterocyclyl" refers to a fully saturated optionally substituted monocyclic, bicyclic, bridged, or spirocyclic hydrocarbon ring, with multiple degrees of substitution being allowed, which contains one or more heteroatom selected from nitrogen, sulfur, and/or oxygen atoms, where N-oxides, sulfur oxides, and dioxides are permissible. Exemplary "heterocyclyl" groups as used herein include, but are not limited to, azetidine, pyrrolidinyl, piperidinyl, piperazinyl, hexahydroazepine, and morpholinyl.

As used herein, the term "aryl" refers to a single benzene ring, fused, bridged, or spirocyclic benzene ring system which may be optionally substituted, with multiple degrees of substitution being allowed. Examples of "aryl" groups as used include, but are not limited to, phenyl, 2-naphthyl, 1-naphthyl, anthracene, and phenanthrene. Preferable aryl rings have five- to ten-members.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthalenyl, and also includes such groups as, for non-limiting examples, dihydronaphthalene and tetrahydronaphthalene.

As used herein, the term "heteroaryl" refers to a monocyclic five to seven membered aromatic ring, or to a fused, bridged, or spirocyclic aromatic ring system comprising two or more of such rings, which may be optionally substituted, with multiple degrees of substitution being allowed. Preferably, such rings contain five- to ten-members. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzoxazole, benzothiophene, indole, indazole, benzimidazole, imidazopyridine, pyrazolopyridine, and pyrazolopyrimidine.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

Typically, but not absolutely, the salts of the present invention are pharmaceutically acceptable salts. Salts encompassed within the term "pharmaceutically acceptable salts" refer to non-toxic salts of the compounds of this invention. Salts of the compound of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

The compounds of formula (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts or solvates thereof, may be administered as the raw chemical. Additionally, the active ingredient may be presented as a pharmaceutical composition.

Accordingly, the invention further provides pharmaceutical compositions that include effective amounts of one or more compounds of the formula (I), or a salt or solvate thereof, and one or more pharmaceutically acceptable carriers, diluents, or excipients. The compound of formula (I) or a salt or solvate thereof, are as herein described. The carrier(s), diluent(s), or excipient(s) must be acceptable, in the sense of being compatible with the other ingredients of the formulation and not deleterious to the recipient of the pharmaceutical composition.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1999) *Protecting Groups in Organic Synthesis, 3rd Edition*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds of formula (I) and novel compounds useful as synthetic intermediates in the preparation of compounds of the present invention.

The compounds can be prepared according to the methods described below using readily available starting materials and reagents. In these reactions, variants may be employed which are themselves known to those of ordinary skill in this art, but are not mentioned in greater detail.

Unless otherwise stated, structures depicted herein are also meant to include compounds which differ only in the presence of one or more isotopically enriched atoms. Compounds having the present structure except for the replacement of a hydrogen atom by a deuterium or tritium, or the replacement of a carbon atom by a $^{13}C$- or $^{14}C$-enriched carbon are within the scope of the invention. For example, deuterium has been widely used to examine the pharmacokinetics and metabolism of biologically active compounds. Although deuterium behaves similarly to hydrogen from a chemical perspective, there are significant differences in bond energies and bond lengths between a deuterium-carbon bond and a hydrogen-carbon bond. Consequently, replacement of hydrogen by deuterium in a biologically active compound may result in a compound that generally retains its biochemical potency and selectivity but manifests significantly different absorption, distribution, metabolism, and/or excretion (ADME) properties compared to its isotope-free counterpart. Thus, deuterium substitution may result in improved drug efficacy, safety, and/or tolerability for some biologically active compounds.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

The therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 0.1 to 20 mg/kg body weight per day. Thus, for a 70 kg adult mammal one example of an actual amount per day would usually be from 10 to 2000 mg. This amount may be given in a single dose per day or in a number (such as two, three, four, five, or more) of sub-doses per day such that the total daily dose is the same. An effective amount of a salt or solvate thereof, may be determined as a proportion of the effective amount of the compound of formula (I) per se. Similar dosages should be appropriate for treatment of the other conditions referred to herein. Pharmaceutical formulations may be presented in unit dose forms containing a predetermined amount of active ingredient per unit dose.

Such a unit may contain, as a non-limiting example, 1 mg to 2 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others. In addition, pharmaceutical formulations may be used to allow delayed or extended exposure to compound of formula (I) under circumstances where delayed or extended exposure would improve therapy.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

Pharmaceutical formulations adapted for topical administration in the mouth include lozenges, pastilles, and mouthwashes.

A compound of the present invention or a salt or solvate thereof, may be employed alone or in combination with other therapeutic agents. The compound of formula (I) and the other pharmaceutically active agent(s) may be administered together or separately and, when administered separately, administration may occur simultaneously or sequentially, in any order. The amounts of the compound of formula (I) and the other pharmaceutically active agent(s) and the relative timings of administration will be selected in order to achieve the desired combined therapeutic effect. The administration in combination of a compound of formula (I) or a salt or solvate thereof with other treatment agents may be in combination by administration concomitantly in: (1) a unitary pharmaceutical composition including a combination of compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Those skilled in the art of organic synthesis will appreciate that there exist multiple means of producing compounds of the present invention which are labeled with a radioisotope appropriate to various uses.

EXPERIMENTAL SECTION

Abbreviations:

As used herein the symbols and conventions used in these processes, schemes and examples are consistent with those used in the contemporary scientific literature, for example, the Journal of the American Chemical Society or the Journal of Biological Chemistry. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| Hz (Hertz); | MHz (megahertz); |
| mol (moles); | mmol (millimoles); |
| RT or rt (room temperature); | hr (hours); |
| min (minutes); | TLC (thin layer chromatography); |
| mp (melting point); | RP (reverse phase); |
| $T_r$ (retention time); | TFA (trifluoroacetic acid); |
| TEA (triethylamine); | THF (tetrahydrofuran); |
| TFAA (trifluoroacetic anhydride); | $CD_3OD$ (deuterated methanol); |
| $CDCl_3$ (deuterated chloroform); | DMSO (dimethylsulfoxide); |
| $SiO_2$ (silica gel); | atm (atmosphere); |
| EtOAc (ethyl acetate); | $CHCl_3$ (chloroform); |
| HCl (hydrochloric acid); | Ac (acetyl); |
| DMF (N,N-dimethylformamide); | Me (methyl); |
| $Cs_2CO_3$ (cesium carbonate); | EtOH (ethanol); |
| Et (ethyl); | t-Bu (tert-butyl); |
| MeOH (methanol) | p-TsOH (p-toluenesulfonic acid); |
| DCM (dichloromethane) | DCE (dichloroethane) |
| $Et_2O$ (diethyl ether) | $K_2CO_3$ (potassium carbonate); |
| $Na_2CO_3$ (sodium carbonate); | i-PrOH (isopropyl alcohol) |
| $NaHCO_3$ (sodium bicarbonate); | ACN (acetonitrile); |
| Pr (propyl); | i-Pr (isopropyl); |
| PE (petroleum ether); | Hex (hexanes); |
| $H_2SO_4$ (sulfuric acid); | HCl (hydrochloric acid); |
| $Et_3N$ (triethylamine); | $Na_2SO_4$ (sodium sulfate); |
| MTBE (methyl tert-butyl ether); | Boc (tert-butoxycarbonyl); |
| DIPEA (diisopropylethylamine); | IPA (isopropanol); |
| HMDS (hexamethyldisilazane) | $NH_4Cl$ (ammonium chloride) |

-continued

| NH₄CO₃ (ammonium carbonate) | MgSO₄ (magnesium sulfate) |
| --- | --- |
| NH₄OH (ammonium hydroxide) | |

All solvents and chemicals were reagent grade. Unless otherwise mentioned, all reagents and solvents were purchased from commercial vendors and used as received. Flash column chromatography was carried out on a Teledyne ISCO CombiFlash Rf system using prepacked columns. Solvents used include hexane, ethyl acetate (EtOAc), dichloromethane, methanol, and chloroform/methanol/ammonium hydroxide (80:18:2) (CMA-80). Purity and characterization of compounds were established by a combination of HPLC, TLC, mass spectrometry, and NMR analyses. $^1$H and $^{13}$C NMR spectra were recorded on a Bruker Avance DPX-300 (300 MHz) spectrometer and were determined in chloroform-d, DMSO-d6, or methanol-d4 with tetramethylsilane (TMS) (0.00 ppm) or solvent peaks as the internal reference. Chemical shifts are reported in ppm relative to the reference signal, and coupling constant (J) values are reported in hertz (Hz). Thin layer chromatography (TLC) was performed on EMD precoated silica gel 60 F254 plates, and spots were visualized with UV light or iodine staining. Low resolution mass spectra were obtained using a Waters Alliance HT/Micromass ZQ system (ESI). All test compounds were greater than 95% pure as determined by HPLC on an Agilent 1100 system using an Agilent Zorbax SB-Phenyl, 2.1 mm×150 mm, 5 μm column with gradient elution using the mobile phases (A) H2O containing 0.1% CF₃COOH and (B) MeCN, with a flow rate of 1.0 mL/min.

A compound of formula (I), can generally be prepared according to Scheme 1 following procedures described previously in German, N. D., Ann M.; Gilmour, Brian P.; Gay, Elaine A.; Wiley, Jenny L.; Thomas, Brian F.; Zhang, Yanan. Diarylureas as Allosteric Modulators of the Cannabinoid CB1 Receptor: Structure-Activity Relationship Studies on 1-(4-Chlorophenyl)-3-{3-[6-(pyrrolidin-1-yl)pyridin-2-yl]phenyl}urea (PSNCBAM-1). *J Med Chem* 2014, 57, 7758-7769; incorporated herein by reference with regard to such synthetic teaching. Other compounds can be prepared according to schemes 2 and 3.

Briefly, commercially available 3-nitrophenyl boronic acid (10) underwent Suzuki coupling with the corresponding aryl bromides under basic conditions catalyzed by Pd(PPh₃)₄ to afford intermediates 11. Reduction of the nitro group in 11 by transfer hydrogenation with hydrazine hydrate and Raney nickel in ethanol provided 3-substituted anilines 12 in good yields. Subsequent reaction between these anilines with 4-chlorophenyl isocyanate afforded the final diarylureas. Alternatively, the anilines 14a-g could be prepared by Suzuki coupling between 3-bromoaniline (13) and the corresponding aryl boronic acids, which was then converted to the final products (15-53) via reaction with 4-chlorophenyl isocyanate. The same 3 step synthetic route (Suzuki coupling, transfer hydrogenation, and coupling with 4-chlorophenyl isocyante) described early was used to prepare compound 57 starting from 4-nitrophenylboronic acid (54). Compound 59 was prepared by coupling between 4-biphenylamine (58) and 4-chloro isocyanate.

Scheme 1.

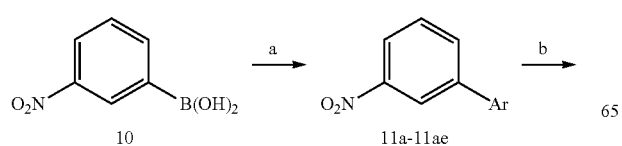

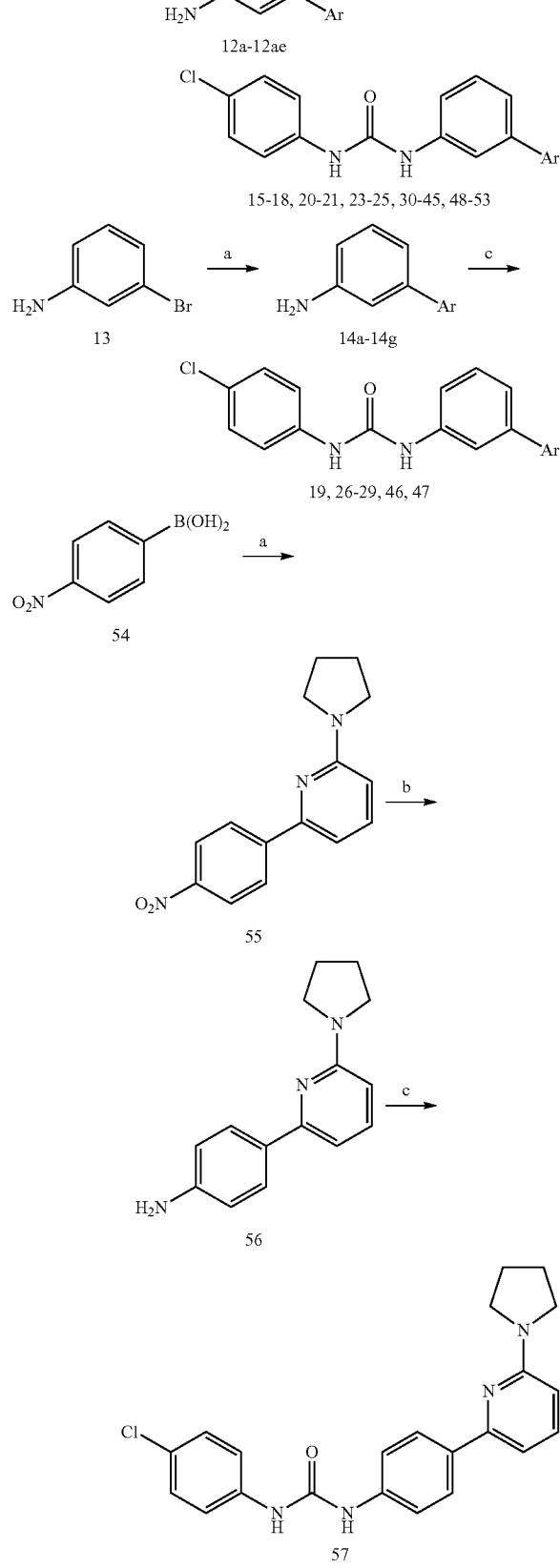

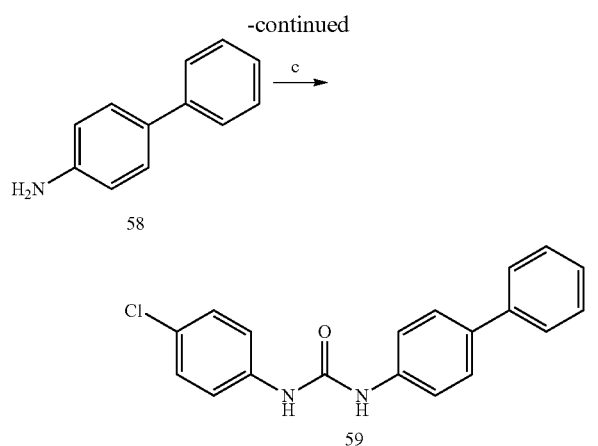

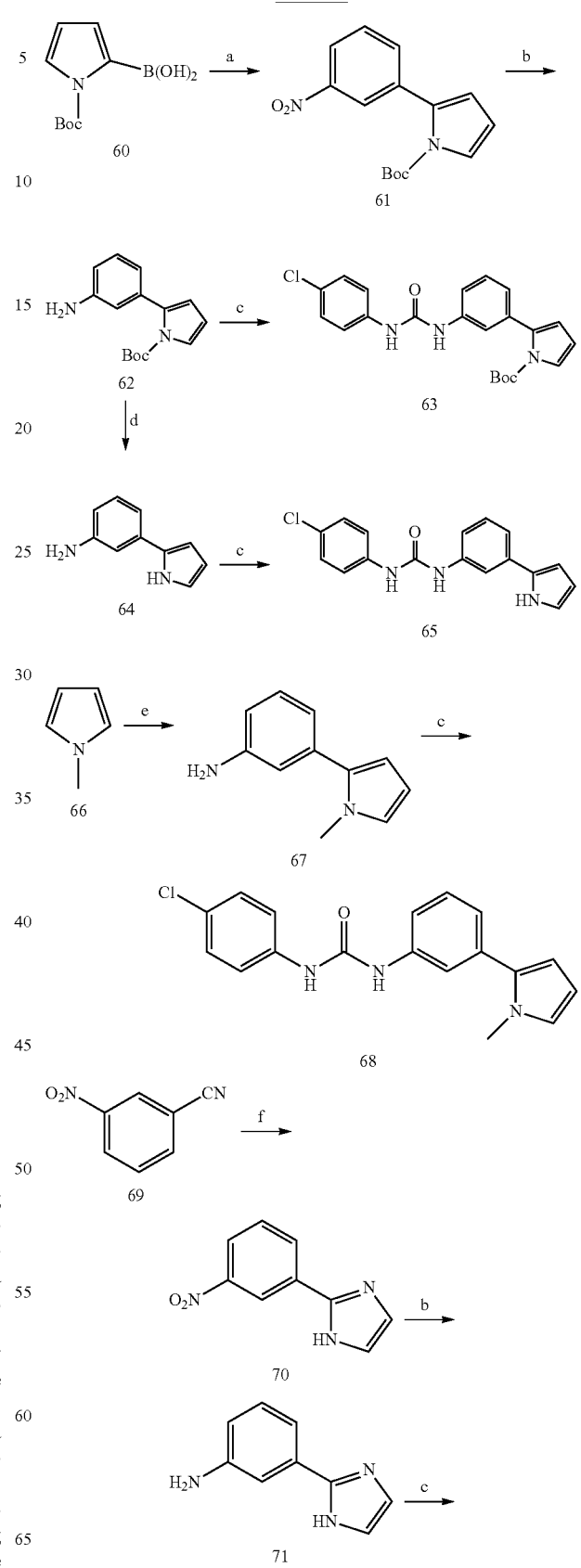

Scheme 2.

11a, 12a, 15: Ar = 6-methoxypyridin-2-yl
11b, 12b, 16: Ar = 4-methylpyridin-2-yl
11c, 12c, 17: Ar = 2-methoxypyridin-4-yl
11d, 12d, 18: Ar = pyridin-2-yl
11e, 12e, 20: Ar = pyridin-4-yl
11f, 12f, 21: Ar = pyrimidin-5-yl
11g, 12g, 23: Ar = 3-OMePh
11h, 12h, 24: Ar = 3-OHPh
11i, 12i, 25: Ar = 3-OiPrPh
11j, 12n, 30: Ar = 4-ClPh
11k, 12k, 31: Ar = 3,5-diClPh
11l, 12l, 32: Ar = 3,4-diClPh
11m, 12m, 33: Ar = 2,6-diClPh
11n, 12n, 34: Ar = 4-FPh
11o, 12o, 35: Ar = 2,4-diFPh
11p, 12p, 36: Ar = 4-tBuPh
11q, 12q, 37: Ar = 3,5-di-tBuPh
11r, 12r, 38: Ar = 3-PhPh
11s, 12s, 39: Ar = 4-PhPh
11t, 12t, 40: Ar = 4-PhCOPh
11u, 12u, 41: Ar = benzofuran-5-yl
11v, 12v, 42: Ar = naphthalen-2-yl
11w, 12w, 43: Ar = quinolin-2-yl
11x, 12x, 44: Ar = quinolin-3-yl
11y, 12y, 45: Ar = 9H-fluoren-2-yl
11z, 12z, 48: Ar = thiophen-2-yl
11aa, 12aa, 49: Ar = 5-methylthiophen-3-yl
11ab, 12ab, 50: Ar = 5-methyl-thiophen-2-yl
11ac, 12ac, 51: Ar = 1,3-thiazol-5-yl
11ad, 12ad, 52: Ar = 1,3-thiazol-4-yl
11ae, 12ae, 53: Ar = 1,3-thiazol-2-yl 14a, 19: Ar = pyridin-3-yl
14b, 26: Ar = 2H-1,3-benzodioxol-5-yl
14c, 27: Ar = 3-MePh
14d, 28: Ar = 2-MePh
14e, 29: Ar = 3-NO$_2$Ph
14f, 46: Ar = furan-3-yl
14g, 47: Ar = thiophen-3-yl Reagents and conditions: (a) 3-nitrophenylboronic acid, Pd(PPh$_3$)$_4$, DME, aq. NaHCO$_3$, reflux, 16 h (b) hydrazine hydrate, Raney Ni, ethanol, 50° C., 2 h (c) 4-chlorophenyl isocyanate, chloroform, 50° C., 16 h.

Compounds 63, 65, 68, and 72 was prepared following scheme 2. Suzuki coupling between N-Noc-pyrrole-2-boronic acid and 1-bromo-3-nitrobenzene to give the intermediate 61. Reduction of the nitro group by Raney-nickel and hydrazine gave the aniline 62. The Boc group of 62 was removed under basic conditions (Marzaro et al, JMC, 2014, 57, 4598-4605) to give aniline 64. 67 was prepared by palladium-catalyzed direct arylation between 3-iodoaniline and N-methylpyrrole (Beladhria et al, Synthesis-Stuttgar, 2012, 44, 2264-2276). The imidazole ring in 70 was formed by reaction between 3-nitrobenzonitrile and aminoacetaldehyde dimethyl acetal (Hah et al, 2011, WO 2011049274 A1). Reduction of nitro group by the typical transfer hydrogenation by Raney-Nickel gave the aniline 71. The final coupling of these aniline intermediates with 4-chlorophenyl isocynate provided the final compounds 63, 65, 68, and 72.

-continued

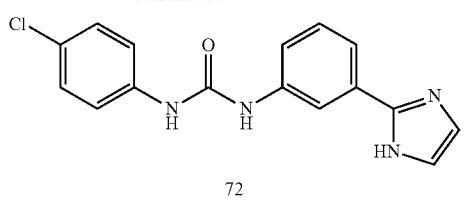

Reagents and conditions: (a) 1-Bromo-3-nitrobenzene, Pd(PPh$_3$)$_4$, DME, NaHCO$_3$, reflux, 16 h (b) hydrazine hydrate, Raney Ni, ethanol, 50° C., 2 h (c) 4-chlorophenyl isocyanate, chloroform, 50° C., 16 h (d) aq. 5% KOH, reflux 4 h (e) 3-iodoaniline, AcOK, Pd(OAc)$_2$, AcNMe$_2$, sealed tube, 150° C., 20 h (f) (i) NaOMe, MeOH, rt, 5 h (ii) (MeO)$_2$CHCH$_2$NH$_2$, AcOH, 70° C., 1 h (iii) aq. 6N HCl, MeOH, 70° C., 3 h.

Compounds 76-86, 90, 91, and 95 were prepared according to Scheme 3. 1-Bromo-3-nitrobenzene (73) underwent Buchwald-Hartwig coupling with the corresponding amine to afford intermediates 74a-j. Reduction of the nitro group by transfer hydrogenation with hydrazine hydrate and Raney nickel in ethanol provided 3-substituted anilines 75a-j in good yields. 3-Nitrobenzyl bromide (87) underwent S$_N$2 substitution with pyrrolidine to give the intermediate 88 which was reduced to the corresponding aniline 89 by hydrogenation. 3-Nitrophenol (92) underwent Mitsunobu reaction to give the intermediate 93 which was reduced to aniline 94 by transfer hydrogenation catalyzed by Raney-Nickel. Subsequent reaction between these anilines (75a-j, 89, and 94) with 4-chlorophenyl isocyanate afforded the final diarylureas 76-86, 90, 91, and 95.

Scheme 3

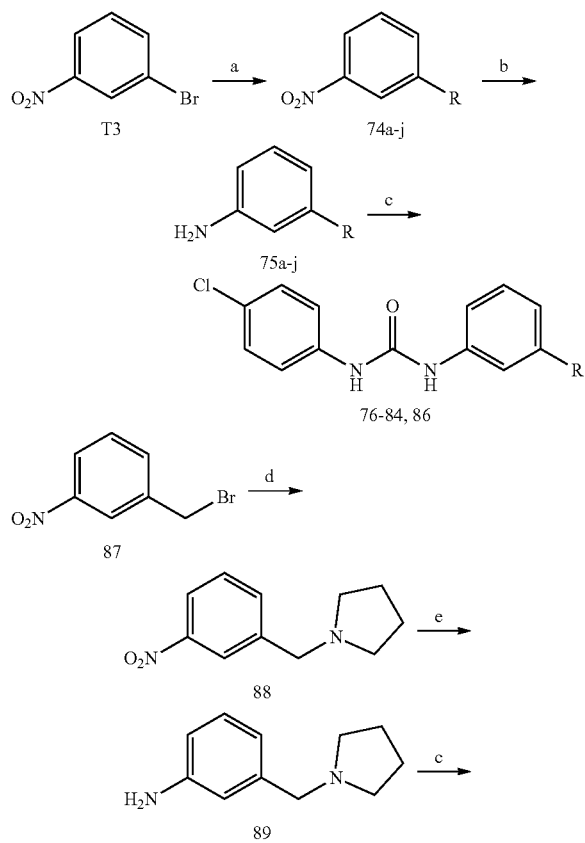

-continued

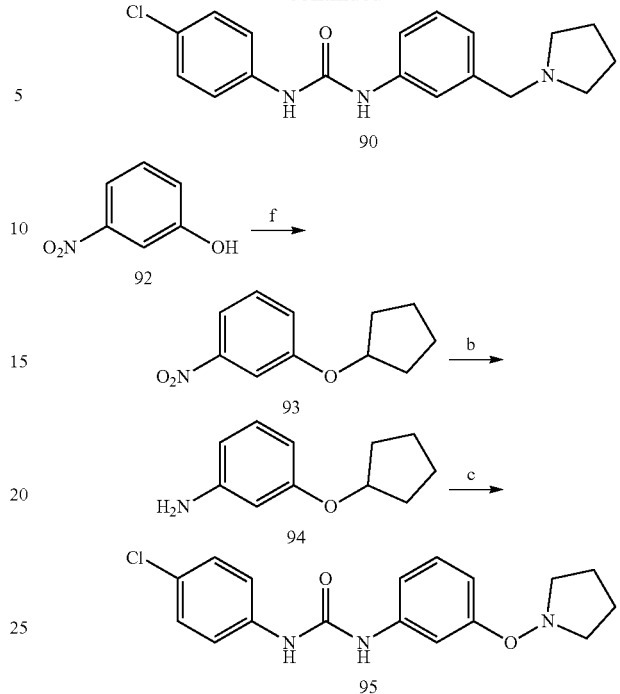

Reagents and conditions:
(a) amine, Pd(OAc)$_2$, Cs$_2$CO$_3$, XantPhos, 1,4-dioxane, 110° C, 16 h
(b) hydrazine hydrate, Raney Ni, ethanol, 50° C., 2 h
(c) 4-chlorophenyl isocyanate, chloroform, 50° C., 16 h
(d) pyrrolidine, Et$_3$N, THF, 60° C., 2 h
(f) cyclopentanol, DIAD, PPh$_3$, THF, 0° C. to rt, 14 h

EXAMPLES

General Procedure A.

To a mixture of aryl bromide or aryl iodide (1 eq), boronic acid (1.1 eq) in dimethoxyethane (0.1 M) was added 1M aqueous NaHCO$_3$ solution (3 eq) followed by Pd(Ph$_3$)$_4$ (0.075 eq). The reaction mixture was refluxed overnight under nitrogen atmosphere. The reaction mixture was diluted with ethyl acetate, washed with a saturated NaHCO$_3$ solution and brine. The combined organic layers were dried over anhydrous MgSO$_4$ and filtered. The filtrate was concentrated in vacuo and the residue was purified by column chromatography (SiO$_2$, ethyl acetate/hexanes) to give the desired product.

2-Methoxy-6-(3-nitrophenyl)pyridine (11a) was prepared from 2-bromo-6-methoxypyridine (0.12 ml, 1.00 mmol) and 3-nitrophenylboronic acid (0.18 g, 1.10 mmol) following the general procedure A as white solid (0.12 g, 50%). $^1$H NMR (300 MHz, CDCl$_3$) δ 8.89 (t, J=1.98 Hz, 1H), 8.01 (dd, J=0.57, 7.35 Hz, 1H), 7.64-7.74 (m, 2H), 7.41 (d, J=7.35 Hz, 1H), 6.72-6.80 (m, 2H), 4.04 (s, 3H). MS (ESI) m/z for C$_{12}$H$_{10}$N$_2$O$_3$ [M+H]+: calcd: 231.1; found: 231.4.

4-Methyl-2-(3-nitrophenyl)pyridine (1 b) was prepared from 2-bromo-4-methylpyridine (0.11 ml, 1.00 mmol) and 3-nitrophenylboronic acid (0.18 g, 1.10 mmol) following the general procedure A as white solid (0.16 g, 73%). $^1$H NMR (300 MHz, CDCl$_3$) δ 8.84 (t, J=1.98 Hz, 1H), 8.58 (d, J=4.90 Hz, 1H), 8.34-8.39 (m, 1H), 8.23-8.27 (m, 1H), 7.60-7.67 (m, 2H), 7.15 (dd, J=0.66, 4.99 Hz, 1H), 2.46 (s, 3H). MS (ESI) m/z for C$_{12}$H$_{10}$N$_2$O$_2$ [M+H]+: calcd: 214.1; found: 214.4.

2-Methoxy-4-(3-nitrophenyl)pyridine (11c) was prepared from 2-methoxy-5-bromopyridine (0.21 ml, 1.60 mmol) and 3-nitrophenylboronic acid (0.29 g, 1.76 mmol) following the general procedure A as white solid (0.34 g, 85%). $^1$H NMR (300 MHz, CDCl$_3$) δ 8.36-8.46 (m, 2H), 8.17-8.25 (m, 1H), 7.79-7.88 (m, 2H), 7.58-7.66 (m, 1H), 6.88 (d, J=8.48 Hz, 1H), 4.00 (s, 3H). MS (ESI) m/z for C$_{12}$H$_{10}$N$_2$O$_3$ [M+H]$^+$: calcd: 231.1; found: 231.5.

2-(3-Nitrophenyl)pyridine (11d) was prepared from 2-bromopyridine (1.00 g, 6.33 mmol) and 3-nitrophenylboronic acid (1.16 g, 6.96 mmol) following the general procedure A as orange solid (0.85 g, 67%). $^1$H NMR (300 MHz, CDCl$_3$) δ 8.86 (t, J=1.88 Hz, 1H), 8.75 (td, J=1.20, 4.94 Hz, 1H), 8.37 (td, J=1.39, 7.77 Hz, 1H), 8.27 (ddd, J=0.94, 2.21, 8.15 Hz, 1H), 7.85 (d, J=1.70 Hz, 2H), 7.66 (t, J=8.01 Hz, 10H), 7.62-7.70 (m, 1H), 7.34 (ddd, J=2.45, 4.76, 6.17 Hz, 1H). MS (ESI) m/z for C$_{11}$H$_8$N$_2$O$_2$[M+H]$^+$: calcd: 201.1; found: 201.4.

4-(3-Nitrophenyl)pyridine (11e) was prepared from 4-bromopyridine hydrochloride (0.19 g, 1.0 mmol) and 3-nitrophenylboronic acid (0.18 g, 1.1 mmol) following the general procedure A as brown solid (0.13 g, 67%). $^1$H NMR (300 MHz, CDCl$_3$) δ 8.73-8.78 (m, 1H), 7.62-7.74 (m, 3H), 7.51-7.59 (m, 2H), 7.43-7.50 (m, 2H). MS (ESI) m/z for C$_{11}$H$_8$N$_2$O$_2$[M+H]$^+$: calcd: 201.1; found: 201.4.

5-(3-Nitrophenyl)pyrimidine (11f) was prepared from 5-bromopyrimidine (0.16 g, 1.0 mmol) and 3-nitrophenylboronic acid (0.18 g, 1.1 mmol) following the general procedure A as light yellow solid (0.10 g, 52%). $^1$H NMR (300 MHz, CDCl$_3$) δ 9.29-9.32 (m, 1H), 9.03 (s, 2H), 8.48 (t, J=1.98 Hz, 1H), 8.33-8.38 (m, 1H), 7.94 (qd, J=0.93, 7.75 Hz, 1H), 7.71-7.79 (m, 1H). MS (ESI) m/z for C$_{10}$H$_7$N$_3$O$_2$ [M+H]$^+$: calcd: 202.1; found: 202.4.

1-(3-Methoxyphenyl)-3-nitrobenzene (11g) was prepared from 2-bromo-3-methoxybenzene (0.30 g, 1.6 mmol) and 3-nitrophenylboronic acid (0.29 g, 1.8 mmol) following the general procedure A as white solid (0.24 g, 65%). $^1$H NMR (300 MHz, CDCl$_3$) δ 8.33-8.40 (m, 1H), 8.13 (td, J=1.06, 8.24 Hz, 1H), 7.80-7.88 (m, 1H), 7.54 (t, J=8.01 Hz, 1H), 7.29-7.41 (m, 1H), 7.13 (dd, J=0.85, 7.63 Hz, 1H), 7.04-7.09 (m, 1H), 6.86-6.94 (m, 1H), 3.82 (s, 3H).

1-(3-Hydroxyphenyl)-3-nitrobenzene (11h) was prepared from 2-bromo-3-hydroxybenzene (0.30 g, 1.7 mmol) and 3-nitrophenylboronic acid (0.32 g, 1.9 mmol) following the general procedure A as white solid (0.24 g, 64%). $^1$H NMR (300 MHz, CDCl$_3$) δ 8.44 (d, J=1.70 Hz, 1H), 8.16-8.25 (m, 1H), 7.85-7.95 (m, 1H), 7.56-7.65 (m, 1H), 7.33-7.40 (m, 1H), 7.20 (br. s., 1H), 7.13 (br. s., 1H), 6.88-7.00 (m, 1H), 5.42 (br. s., 1H).

1-(3-Nitrophenyl)-3-(propan-2-yloxy)benzene (11i) was prepared from 1-bromo-3-(propan-2-yloxy)benzene (0.30 g, 1.7 mmol) and 3-nitrophenylboronic acid (0.28 g, 1.7 mmol) following the general procedure A as yellow liquid (0.30 g, 84%). $^1$H NMR (300 MHz, CDCl$_3$) δ 8.44 (t, J=1.98 Hz, 1H), 8.15-8.24 (m, 1H), 7.90 (td, J=1.25, 7.86 Hz, 1H), 7.54-7.65 (m, 1H), 7.33-7.44 (m, 1H), 7.10-7.20 (m, 2H), 6.95 (dd, J=1.88, 8.10 Hz, 1H), 4.64 (spt, J=6.06 Hz, 1H), 1.34-1.43 (m, 6H).

1-(4-Chlorophenyl)-3-nitrobenzene (11j) was prepared from 1-iodo-4-chlorobenzene (0.30 g, 1.25 mmol) and 3-nitrophenylboronic acid (0.23 g, 1.38 mmol) following the general procedure A as white solid (0.24 g, 82%). $^1$H NMR (300 MHz, CDCl$_3$) δ 8.37-8.43 (m, 1H), 8.21 (ddd, J=1.04, 2.26, 8.19 Hz, 1H), 7.88 (ddd, J=1.04, 1.74, 7.77 Hz, 1H), 7.62 (t, J=8.01 Hz, 1H), 7.51-7.58 (m, 2H), 7.41-7.50 (m, 2H).

1,3-Dichloro-4-(3-nitrophenyl)benzene (11k) was prepared from 1-bromo-3,5-dichlorobenzene (0.30 g, 1.32 mmol) and 3-nitrophenylboronic acid (0.24 g, 1.46 mmol) following the general procedure A as white solid (0.29 g, 82%). $^1$H NMR (300 MHz, CDCl$_3$) δ 8.41 (t, J=1.79 Hz, 1H), 8.27 (dd, J=1.22, 8.19 Hz, 1H), 7.87 (d, J=7.72 Hz, 1H), 7.62-7.70 (m, 1H), 7.50 (d, J=1.70 Hz, 2H), 7.43 (t, J=1.70 Hz, 1H).

1,2-Dichloro-4-(3-nitrophenyl)benzene (11l) was prepared from 1-iodo-3,4-dichlorobenzene (0.30 g, 1.10 mmol) and 3-nitrophenylboronic acid (0.20 g, 1.21 mmol) following the general procedure A as white solid (0.19 g, 65%). $^1$H NMR (300 MHz, CDCl$_3$) δ 8.40 (t, J=1.98 Hz, 1H), 8.21-8.27 (m, 1H), 7.87 (td, J=1.25, 7.68 Hz, 1H), 7.71 (d, J=2.07 Hz, 1H), 7.64 (t, J=8.01 Hz, 1H), 7.55-7.59 (m, 1H), 7.46 (dd, J=2.17, 8.38 Hz, 1H).

1,3-Dichloro-2-(3-nitrophenyl)benzene (11m) was prepared from 2-bromo-1,3-dichlorobenzene (0.30 g, 1.32 mmol) and 3-nitrophenylboronic acid (0.18 g, 1.10 mmol) following the general procedure A as yellow solid (0.23 g, 65%). $^1$H NMR (300 MHz, CDCl$_3$) δ 8.26-8.34 (m, 1H), 8.18 (d, J=1.70 Hz, 1H), 7.59-7.68 (m, 2H), 7.41-7.49 (m, 2H), 7.29-7.35 (m, 1H).

1-(4-Fluorophenyl)-3-nitrobenzene (11n) was prepared from 1-bromo-4-fluorobenzene (0.30 g, 1.71 mmol) and 3-nitrophenylboronic acid (0.31 g, 1.88 mmol) following the general procedure A as white solid (0.35 g, 93%). $^1$H NMR (300 MHz, CDCl$_3$) δ 8.39 (s, 1H), 8.19 (d, J=7.54 Hz, 1H), 7.86 (d, J=7.72 Hz, 1H), 7.57-7.62 (m, 2H), 7.18 (t, J=8.57 Hz, 2H).

1-(2,4-Difluorophenyl)-3-nitrobenzene (11O) was prepared from 1-bromo-2,4-difluorobenzene (0.19 g, 1.00 mmol) and 3-nitrophenylboronic acid (0.18 g, 1.10 mmol) following the general procedure A as white solid (0.17 g, 71%). $^1$H NMR (300 MHz, CDCl$_3$) δ 8.37 (s, 1H), 8.23 (td, J=1.08, 8.19 Hz, 1H), 7.85 (dd, J=1.13, 7.72 Hz, 1H), 7.59-7.67 (m, 1H), 7.46 (dt, J=6.31, 8.62 Hz, 1H), 6.92-7.06 (m, 2H).

1-(4-tert-Butylphenyl)-3-nitrobenzene (11p) was prepared from 1-bromo-4-tert-butylbenzene (0.30 g, 1.41 mmol) and 3-nitrophenylboronic acid (0.26 g, 1.55 mmol) following the general procedure A as colorless liquid (0.15 g, 42%). $^1$H NMR (300 MHz, CDCl$_3$) δ 8.43 (t, J=1.88 Hz, 1H), 8.12-8.18 (m, 1H), 7.87-7.92 (m, 1H), 7.48-7.60 (m, 5H), 1.37 (s, 9H).

1,3-Di-tert-butyl-5-(3-nitrophenyl)benzene (11q) was prepared from 1-bromo-3,5-di-tert-butylbenzene (0.30 g, 1.1 mmol) and 3-nitrophenylboronic acid (0.20 g, 1.2 mmol) following the general procedure A as colorless liquid (0.22 g, 63%). $^1$H NMR (300 MHz, CDCl$_3$) δ 8.41-8.44 (m, 1H), 8.19 (td, J=1.08, 8.19 Hz, 1H), 7.91 (dd, J=0.47, 7.82 Hz, 1H), 7.59-7.63 (m, 1H), 7.52 (t, J=1.51 Hz, 1H), 7.42 (d, J=1.70 Hz, 2H), 1.40 (s, 21H).

1-(3-Nitrophenyl)-3-phenylbenzene (11r) was prepared from 1-bromo-3-phenylbenzene (0.17 ml, 1.0 mmol) and 3-nitrophenylboronic acid (0.18 g, 1.1 mmol) following the general procedure A as colorless liquid (0.27 g, 98%). $^1$H NMR (300 MHz, CDCl$_3$) δ 8.52 (t, J=1.98 Hz, 1H), 8.21-8.26 (m, 1H), 7.98 (td, J=1.27, 7.82 Hz, 1H), 7.81-7.84 (m, 1H), 7.63-7.69 (m, 4H), 7.59-7.63 (m, 2H), 7.45-7.50 (m, 2H), 7.39-7.43 (m, 1H).

1-(4-Phenylphenyl)-3-nitrobenzene (11s) was prepared from 1-bromo-4-phenylbenzene (0.30 g, 1.29 mmol) and 3-nitrophenylboronic acid (0.24 g, 1.42 mmol) following the general procedure A as white solid (0.21 g, 58%). $^1$H NMR (300 MHz, CDCl$_3$) δ 8.50 (t, J=1.98 Hz, 1H), 8.20 (ddd, J=0.75, 2.12, 8.24 Hz, 1H), 7.95 (td, J=1.18, 7.82 Hz, 1H), 7.71 (d, J=0.94 Hz, 4H), 7.62-7.66 (m, 3H), 7.44-7.51 (m, 2H), 7.37-7.42 (m, 1H).

[4-(3-Nitrophenyl)phenyl](phenyl)methanone (11t) was prepared from (4-iodophenyl)(phenyl)methanone (0.31 g, 1.00 mmol) and 3-nitrophenylboronic acid (0.18 g, 1.10 mmol) following the general procedure A as brown solid (0.18 g, 60%). $^1$H NMR (300 MHz, CDCl$_3$) δ 8.49-8.55 (m, 1H), 8.28 (dd, J=1.79, 7.63 Hz, 1H), 7.91-8.01 (m, 3H), 7.81-7.87 (m, 2H), 7.73-7.78 (m, 2H), 7.60-7.71 (m, 2H), 7.49-7.56 (m, 2H).

5-(3-Nitrophenyl)-1-benzofuran (11u) was prepared from 5-bromo-1-benzofuran (0.13 ml, 1.00 mmol) and 3-nitrophenylboronic acid (0.18 g, 1.10 mmol) following the general procedure A as white solid (0.20 g, 84%). $^1$H NMR (300 MHz, CDCl$_3$) δ 8.47 (t, J=1.98 Hz, 1H), 8.18 (ddd, J=1.04, 2.21, 8.24 Hz, 1H), 7.90-7.96 (m, 1H), 7.81-7.85 (m, 1H), 7.68-7.71 (m, 1H), 7.58-7.64 (m, 2H), 7.51-7.56 (m, 1H), 6.85 (dd, J=0.85, 2.17 Hz, 1H).

2-(3-Nitrophenyl)naphthalene (11v) was prepared from 2-bromonaphthalene (0.41 g, 2.00 mmol) and 3-nitrophenylboronic acid (0.37 g, 2.20 mmol) following the general procedure A as white solid (0.37 g, 74%). $^1$H NMR (300 MHz, CDCl$_3$) δ 8.57 (t, J=1.98 Hz, 1H), 8.22 (ddd, J=0.94, 2.17, 8.19 Hz, 1H), 8.08 (d, J=1.51 Hz, 1H), 8.01-8.06 (m, 1H), 7.96 (d, J=8.48 Hz, 1H), 7.86-7.93 (m, 2H), 7.74 (dd, J=1.88, 8.48 Hz, 1H), 7.64 (t, J=8.01 Hz, 1H), 7.52-7.57 (m, 2H).

2-(3-Nitrophenyl)quinoline (11w) was prepared from 2-bromoquinoline (0.18 g, 0.84 mmol) and 3-nitrophenylboronic acid (0.15 g, 0.93 mmol) following the general procedure A as white solid (0.02 g, 11%). $^1$H NMR (300 MHz, CDCl$_3$) δ 9.05 (t, J=1.88 Hz, 1H), 8.53-8.58 (m, 1H), 8.28-8.34 (m, 2H), 8.20 (d, J=8.48 Hz, 1H), 7.94 (d, J=8.67 Hz, 1H), 7.88 (d, J=8.10 Hz, 1H), 7.75-7.82 (m, 1H), 7.70 (t, J=8.01 Hz, 1H), 7.55-7.63 (m, 1H).

3-(3-Nitrophenyl)quinoline (11x) was prepared from 3-bromoquinoline (0.14 ml, 1.00 mmol) and 3-nitrophenylboronic acid (0.18 g, 1.10 mmol) following the general procedure A as white solid (0.08 g, 33%). $^1$H NMR (300 MHz, CDCl$_3$) δ 9.19 (d, J=2.26 Hz, 1H), 8.55-8.60 (m, 1H), 8.38 (d, J=2.26 Hz, 1H), 8.29 (dd, J=1.41, 8.19 Hz, 1H), 8.17 (d, J=8.48 Hz, 1H), 8.05 (d, J=7.91 Hz, 1H), 7.93 (d, J=8.10 Hz, 1H), 7.79 (dt, J=1.32, 7.72 Hz, 1H), 7.72 (t, J=8.01 Hz, 1H), 7.60-7.67 (m, 1H).

2-(3-Nitrophenyl)-9H-fluorene (11y) was prepared from 2-bromo-9H-fluorene (0.25 ml, 1.00 mmol) and 3-nitrophenylboronic acid (0.18 g, 1.10 mmol) following the general procedure A as yellow solid (0.07 g, 26%). $^1$H NMR (300 MHz, CDCl$_3$) δ 8.51 (t, J=1.98 Hz, 1H), 8.19 (ddd, J=0.94, 2.26, 8.10 Hz, 1H), 7.97 (qd, J=0.94, 7.72 Hz, 1H), 7.84-7.91 (m, 2H), 7.81 (d, J=4.71 Hz, 2H), 7.62-7.67 (m, 1H), 7.56-7.60 (m, 1H), 7.40 (d, J=6.97 Hz, 1H), 7.36 (dd, J=1.32, 7.35 Hz, 1H), 3.99 (s, 2H).

2-(3-Nitrophenyl)thiophene (11z) was prepared from 2-bromothiophene (0.10 ml, 1.00 mmol) and 3-nitrophenylboronic acid (0.18 g, 1.10 mmol) following the general procedure A as yellow solid (0.18 g, 92%). $^1$H NMR (300 MHz, CDCl$_3$) δ 8.42 (t, J=1.88 Hz, 1H), 8.06-8.13 (m, 1H), 7.89 (d, J=7.72 Hz, 1H), 7.53 (t, J=8.01 Hz, 1H), 7.42 (dd, J=0.85, 3.67 Hz, 1H), 7.37 (dd, J=0.75, 5.09 Hz, 1H), 7.12 (dd, J=3.77, 5.09 Hz, 1H).

2-Methyl-4-(3-nitrophenyl)thiophene (11aa) was prepared from 4-bromo-2-methylthiophene (0.10 ml, 1.00 mmol) and 3-nitrophenylboronic acid (0.18 g, 1.10 mmol) following the general procedure A as yellow solid (0.09 g, 42%). $^1$H NMR (300 MHz, CDCl$_3$) δ 8.37 (t, J=1.88 Hz, 1H), 8.09 (td, J=1.06, 8.24 Hz, 1H), 7.85 (d, J=7.72 Hz, 1H), 7.52 (t, J=8.01 Hz, 1H), 7.32 (d, J=1.51 Hz, 1H), 7.08 (s, 1H), 2.54 (s, 1H).

2-Methyl-5-(3-nitrophenyl)thiophene (11ab) was prepared from 4-bromo-2-methylthiophene (0.10 ml, 1.00 mmol) and 3-nitrophenylboronic acid (0.18 g, 1.10 mmol) following the general procedure A as yellow solid (0.09 g, 42%). $^1$H NMR (300 MHz, CDCl$_3$) δ 8.36 (t, J=1.98 Hz, 1H), 8.05 (ddd, J=0.94, 2.12, 8.24 Hz, 1H), 7.79-7.84 (m, 1H), 7.50 (t, J=8.01 Hz, 1H), 7.22 (d, J=3.58 Hz, 1H), 6.75-6.79 (m, 1H), 2.50-2.56 (m, 3H).

5-(3-Nitrophenyl)-1,3-thiazole (11ac) was prepared from 5-bromo-1,3-thiazole (0.09 ml, 1.00 mmol) and 3-nitrophenylboronic acid (0.18 g, 1.10 mmol) following the general procedure A as yellow solid (0.10 g, 46%). $^1$H NMR (300 MHz, CDCl$_3$) δ 8.86 (s, 1H), 8.43 (t, J=1.88 Hz, 1H), 8.17-8.24 (m, 2H), 7.88-7.94 (m, 1H), 7.58-7.66 (m, 1H).

4-(3-Nitrophenyl)-1,3-thiazole (1 ad) was prepared from 4-bromo-1,3-thiazole (0.09 ml, 1.00 mmol) and 3-nitrophenylboronic acid (0.18 g, 1.10 mmol) following the general procedure A as yellow solid (0.12 g, 58%). $^1$H NMR (300 MHz, CDCl$_3$) δ 8.93 (d, J=1.88 Hz, 1H), 8.78 (t, J=1.98 Hz, 1H), 8.26-8.31 (m, 1H), 8.17-8.22 (m, 1H), 7.72 (d, J=2.07 Hz, 1H), 7.62 (t, J=8.01 Hz, 1H).

2-(3-Nitrophenyl)-1,3-thiazole (11ae) was prepared from 4-bromo-1,3-thiazole (0.09 ml, 1.00 mmol) and 3-nitrophenylboronic acid (0.18 g, 1.10 mmol) following the general procedure A as yellow solid (0.08 g, 37%). $^1$H NMR (300 MHz, CDCl$_3$) δ 8.80 (t, J=1.88 Hz, 1H), 8.24-8.32 (m, 1H), 7.87-7.96 (m, 2H), 7.43-7.47 (m, 2H).

3-(Pyridin-3-yl)aniline (14a) was prepared from 3-bromoaniline (0.11 ml, 1.00 mmol) and 3-pyridinylboronic acid (0.18 g, 1.10 mmol) following the general procedure A as white solid (0.10 g, 59%). $^1$H NMR (300 MHz, CDCl$_3$) δ 8.81 (d, J=1.70 Hz, 1H), 8.56 (dd, J=1.41, 4.80 Hz, 1H), 7.77-7.85 (m, 1H), 7.31 (dd, J=4.71, 7.91 Hz, 1H), 7.24 (t, J=7.72 Hz, 1H), 6.91-6.98 (m, 1H), 6.83-6.88 (m, 1H), 6.71 (td, J=1.11, 7.96 Hz, 1H), 3.83 (br. s., 2H). MS (ESI) m/z for C$_{11}$H$_{10}$N$_2$ [M+H]$^+$: calcd: 171.1; found: 171.0.

3-(2H-1,3-Benzodioxol-5-yl)aniline (14b) was prepared from 3-bromoaniline (0.19 ml, 1.74 mmol) and (2H-1,3-benzodioxol-5-yl)boronic acid (0.32 g, 2.08 mmol) following the general procedure A as yellow liquid (0.08 g, 60%). $^1$H NMR (300 MHz, CDCl$_3$) δ 6.95-7.04 (m, 2H), 6.81-6.90 (m, 4H), 6.61-6.66 (m, 1H), 6.55-6.61 (m, 2H), 6.41 (d, J=2.64 Hz, 1H), 6.24 (d, J=2.54, 8.38 Hz, 1H), 5.89 (s, 2H), 3.73 (br. s., 2H). MS (ESI) m/z for C$_{13}$H$_{11}$NO$_2$ [M+H]$^+$: calcd: 213.1; found: 213.2.

3-(3-Methylphenyl)aniline (14c) was prepared from 3-bromoaniline (0.11 ml, 1.00 mmol) and 3-methylphenylboronic acid (0.16 g, 1.10 mmol) following the general procedure A as yellow liquid (0.12 g, 66%). $^1$H NMR (300 MHz, CDCl$_3$) δ 7.29-7.39 (m, 3H), 7.12-7.22 (m, 2H), 6.96-7.00 (m, 1H), 6.90 (t, J=1.98 Hz, 1H), 6.67 (ddd, J=0.94, 2.26, 7.91 Hz, 1H), 3.73 (br. s., 2H), 2.41 (s, 3H).

3-(2-Methylphenyl)aniline (14d) was prepared from 3-bromoaniline (0.11 ml, 1.00 mmol) and 2-mnethylphenylboronic acid (0.15 g, 1.10 mmol) following the general procedure A as yellow liquid (0.15 g, 82%). $^1$H NMR (300 MHz, CDCl$_3$) δ 7.20-7.29 (m, 5H), 6.61-6.74 (m, 3H), 3.69 (br. s., 2H), 2.28 (s, 3H). MS (ESI) m/z for C$_{13}$H$_{13}$N [M+H]$^+$: calcd: 184.1; found: 184.2.

3-(3-Nitrophenyl)aniline (14e) was prepared from 3-bromoaniline (0.19 ml, 1.74 mmol) and 3-nitrophenylboronic acid (0.32 g, 1.91 mmol) following the general procedure A as white solid (0.08 g, 21%). $^1$H NMR (300 MHz, CDCl$_3$) δ 8.37-8.45 (m, 1H), 8.17 (ddd, J=0.94, 2.26, 8.10 Hz, 1H), 7.83-7.92 (m, 1H), 7.57 (t, J=7.91 Hz, 1H), 7.21-7.28 (m, 1H), 6.96-7.03 (m, 1H), 6.92 (t, J=1.88 Hz, 1H), 6.72-6.78

(m, 1H), 3.82 (br. s., 2H). MS (ESI) m/z for $C_{12}H_{10}N_2O_2$ [M+H]$^+$: calcd: 215.1; found: 215.0.

3-(Furan-3-yl)aniline (14f) was prepared from 3-bromoaniline (0.19 ml, 1.74 mmol) and (furan-3-yl)boronic acid (0.21 g, 1.91 mmol) following the general procedure A as white solid (0.09 g, 32%). $^1$H NMR (300 MHz, CDCl$_3$) δ 7.66-7.71 (m, 1H), 7.45 (t, J=1.70 Hz, 1H), 7.12-7.20 (m, 1H), 6.90 (td, J=1.30, 7.58 Hz, 1H), 6.81 (t, J=1.88 Hz, 1H), 6.66 (d, J=1.13 Hz, 1H), 6.60 (ddd, J=0.94, 2.45, 7.91 Hz, 1H), 3.69 (br. s., 2H). MS (ESI) m/z for $C_{10}H_9NO$ [M+H]$^+$: calcd: 160.1; found: 160.1.

3-(Thiophen-3-yl)aniline (14g) was prepared from 3-bromoaniline (0.19 ml, 1.74 mmol) and (thiophen-3-yl)boronic acid (0.25 g, 1.91 mmol) following the general procedure A as white solid (0.03 g, 10%). $^1$H NMR (300 MHz, CDCl$_3$) δ 7.38-7.42 (m, 1H), 7.32-7.37 (m, 2H), 7.15-7.22 (m, 1H), 7.00 (td, J=1.25, 7.68 Hz, 1H), 6.92 (t, J=1.88 Hz, 1H), 6.63 (ddd, J=0.94, 2.26, 7.91 Hz, 1H), 3.71 (br. s., 2H). MS (ESI) m/z for $C_{10}H_9NS$ [M+H]$^+$: calcd: 176.1; found: 176.3.

2-(4-Nitrophenyl)-6-(pyrrolidin-1-yl)pyridine (55) was prepared from 2-bromo-6-(pyrrolidin-1-yl)pyridine (0.30 g, 1.32 mmol) and 4-nitrophenylboronic acid (0.24 g, 1.45 mmol) following the general procedure A as orange solid (0.28 g, 80%). MS (ESI) m/z for $C_{15}H_{15}N_3O_2$ [M+H]$^+$: calcd: 270.1; found: 270.3.

tert-Butyl 2-(3-nitrophenyl)-1H-pyrrole-1-carboxylate (61) was prepared from 1-bromo-3-nitrobenzene (0.20 g, 1 mmol) and N-Boc-2-pyrroleboronic acid (0.23 g, 1.1 mmol) following the general procedure A as yellow solid (0.15 g, 51%). $^1$H NMR (300 MHz, CDCl$_3$) δ 8.12-8.28 (m, 2H), 7.69 (d, J=6.22 Hz, 1H), 7.47-7.58 (m, 1H), 7.36-7.44 (m, 1H), 6.22-6.35 (m, 2H), 1.40 (s, 9H).

General Procedure D.

To a solution of 1-bromo-3-nitrobenzene (1 eq.) in 1,4-dioxane (0.45 M) was added corresponding amine (1.4 eq.), palladium (II) acetate (0.12 eq.), cesium carbonate (2 eq.) and XantPhos (0.12 eq.). The reaction mixture was heated at 80° C. under nitrogen for 8 h. After cooling to room temperature, the reaction mixture was diluted with ethyl acetate, washed with water twice and then with brine. The organic fraction was dried over anhydrous magnesium sulfate, filtered, and concentrated in vacuo. The residue was purified by column chromatography (SiO$_2$, ethyl acetate/hexanes) to give the desired product.

1-(3-Nitrophenyl)piperidine (74a) was prepared from 1-bromo-3-nitrobenzene (0.40 g, 2 mmol) and piperidine (0.28 ml, 2.8 mmol) following the general procedure D as red liquid (0.24 g, 58%). $^1$H NMR (300 MHz, CDCl$_3$) δ 7.71 (t, J=2.26 Hz, 1H), 7.60 (dd, J=1.32, 8.10 Hz, 1H), 7.34 (t, J=8.19 Hz, 1H), 7.18 (dd, J=1.98, 8.38 Hz, 1H), 3.23-3.31 (m, 4H), 1.67-1.77 (m, 4H), 1.59-1.67 (m, 2H). MS (ESI) m/z for $C_{11}H_{14}N_2O_2$ [M+H]$^+$: calcd: 207.3; found: 207.5.

4-(3-Nitrophenyl)morpholine (74b) was prepared from 1-bromo-3-nitrobenzene (0.20 g, 1 mmol) and piperidine (0.09 ml, 1.4 mmol) following the general procedure D as yellow solid (0.05 g, 22%). $^1$H NMR (300 MHz, CDCl$_3$) δ 7.65-7.73 (m, 2H), 7.40 (t, J=8.10 Hz, 1H), 7.18 (dd, J=1.70, 8.29 Hz, 1H), 3.88 (t, J=4.90 Hz, 4H), 3.25 (t, J=4.90 Hz, 4H). MS (ESI) m/z for $C_{10}H_{12}N_2O_3$ [M+H]$^+$: calcd: 208.1; found: 208.3.

4-(3-Nitrophenyl)pyrrolidine (74c) was prepared from 1-bromo-3-nitrobenzene (0.20 g, 1 mmol) and piperidine (0.08 ml, 1.4 mmol) following the general procedure D as orange solid (0.13 g, 69%). $^1$H NMR (300 MHz, CDCl$_3$) δ 7.45 (dd, J=1.51, 7.91 Hz, 1H), 7.29-7.34 (m, 2H), 6.79 (dd, J=1.98, 8.19 Hz, 1H), 3.33 (t, J=6.59 Hz, 4H), 2.05 (td, J=3.46, 6.45 Hz, 4H). MS (ESI) m/z for $C_{10}H_{12}N_2O_2$ [M+H]$^+$: calcd: 193.1; found: 193.3.

1-Methyl-4-(3-nitrophenyl)piperazine (74d) was prepared from 1-bromo-3-nitrobenzene (0.20 g, 1 mmol) and 1-methylpiperazine (0.11 ml, 1.4 mmol) following the general procedure D as yellow liquid (0.18 g, 82%). $^1$H NMR (300 MHz, CDCl$_3$) δ 7.71 (t, J=2.26 Hz, 1H), 7.64 (dd, J=1.32, 8.10 Hz, 1H), 7.37 (t, J=8.19 Hz, 1H), 7.19 (dd, J=1.88, 8.29 Hz, 1H), 3.30 (t, J=5.10 Hz, 4H), 2.58 (t, J=5.30 Hz, 4H), 2.36 (s, 3H). MS (ESI) m/z for $C_{11}H_{15}N_3O_2$ [M+H]$^+$: calcd: 222.1; found: 222.4.

1-(3-Nitrophenyl)azetidine (74e) was prepared from 1-bromo-3-nitrobenzene (0.20 g, 1 mmol) and azetidine (0.14 ml, 2 mmol) following the general procedure D as red solid (0.16 g, 87%). $^1$H NMR (300 MHz, CDCl$_3$) δ 7.52 (ddd, J=0.75, 2.07, 8.10 Hz, 1H), 7.30 (t, J=8.10 Hz, 1H), 7.19 (t, J=2.26 Hz, 1H), 6.67 (ddd, J=0.75, 2.26, 8.10 Hz, 1H), 3.96 (t, J=7.35 Hz, 4H), 2.43 (quin, J=7.30 Hz, 2H). MS (ESI) m/z for $C_9H_{10}N_2O_2$ [M+H]$^+$: calcd: 179.1; found: 179.4.

4,4-Difluoro-1-(3-nitrophenyl)piperidine (74f) was prepared from 1-bromo-3-nitrobenzene (0.10 g, 0.5 mmol) and 4,4-difluoropiperidine (0.17 g, 0.7 mmol) following the general procedure D as yellow solid (0.16 g, 87%). $^1$H NMR (300 MHz, CDCl$_3$) δ 7.74 (t, J=2.35 Hz, 1H), 7.66-7.72 (m, 1H), 7.40 (t, J=8.19 Hz, 1H), 7.18-7.24 (m, 1H), 3.46 (t, J=5.70 Hz, 4H), 2.04-2.20 (m, 4H). MS (ESI) m/z for $C_{11}H_{12}F_2N_2O_2$ [M+H]$^+$: calcd: 242.1; found: 242.2.

(1S,4S)-7-(3-Nitrophenyl)-7-azabicyclo[2.2.1]heptane (74g) was prepared from 1-bromo-3-nitrobenzene (0.10 g, 0.5 mmol) and 7-azabicyclo[2.2.1]heptane (0.14 g, 0.7 mmol) following the general procedure D as yellow liquid (0.16 g, 87%). $^1$H NMR (300 MHz, CDCl$_3$) δ 7.67 (t, J=2.26 Hz, 1H), 7.60 (dd, J=1.41, 8.01 Hz, 1H), 7.31 (t, J=8.10 Hz, 1H), 7.14 (dd, J=1.98, 8.19 Hz, 1H), 4.24 (td, J=2.52, 4.57 Hz, 2H), 1.75-1.85 (m, 4H), 1.45-1.54 (m, 4H). MS (ESI) m/z for $C_{12}H_{14}N_2O_2$ [M+H]$^+$: calcd: 219.1; found: 219.2.

1-(3-Nitrophenyl)azepane (74h) was prepared from 1-bromo-3-nitrobenzene (0.20 g, 1 mmol) and hexamethyleneimine (0.16 ml, 1.4 mmol) following the general procedure D as orange liquid (0.11 g, 48%). $^1$H NMR (300 MHz, CDCl$_3$) δ 7.40-7.48 (m, 2H), 7.25-7.29 (m, 1H), 6.90-6.95 (m, 1H), 3.49 (t, J=5.80 Hz, 4H), 1.81 (dd, J=4.05, 5.18 Hz, 4H), 1.52-1.58 (m, 4H). MS (ESI) m/z for $C_{12}H_{16}N_2O_2$ [M+H]$^+$: calcd: 221.1; found: 221.2.

6-(3-Nitrophenyl)-2-oxa-6-azaspiro[3.3]heptane (74i) was prepared from 1-bromo-3-nitrobenzene (0.20 g, 1 mmol) and 2-oxa-6-azaspiro[3.3]heptane hemioxalate (0.40 g, 1.4 mmol) following the general procedure D as yellow solid (0.07 g, 33%). $^1$H NMR (300 MHz, CDCl$_3$) δ 7.57 (ddd, J=0.75, 2.07, 8.10 Hz, 1H), 7.32 (t, J=8.19 Hz, 1H), 7.21 (t, J=2.26 Hz, 1H), 6.69 (ddd, J=0.75, 2.26, 8.10 Hz, 1H), 4.86 (s, 4H), 4.11 (s, 4H). MS (ESI) m/z for $C_{11}H_{12}N_2O_3$ [M+H]$^+$: calcd: 221.1; found: 221.2.

N,N-Diethyl-3-nitroaniline (74j) was prepared from 1-bromo-3-nitrobenzene (0.20 g, 1 mmol) and diethylamine (0.2 ml, 2 mmol) following the general procedure D as red liquid (0.14 g, 74%). $^1$H NMR (300 MHz, CDCl$_3$) δ 7.42-7.46 (m, 2H), 7.29 (s, 1H), 6.92 (s, 1H), 3.41 (q, J=7.16 Hz, 4H), 1.20 (t, J=7.06 Hz, 6H). MS (ESI) m/z for $C_{10}H_{14}N_2O_2$ [M+H]$^+$: calcd: 195.1; found: 195.4.

1-(Cyclopentyloxy)-3-nitrobenzene (93). To a solution of 3-nitrophenol (0.14 g, 1 mmol) in THF (5 ml) was added triphenylphosphine (0.29 g, 1.1 mmol), cyclopentanol 0.1 ml, 1.1 mmol) under nitrogen. The reaction was cooled in an ice-water bath and diisopropyl azodicarboxylate (0.22 ml, 1.1 ml) was added slowly over 10 min. The reaction was raised to room temperature and stirred for 4 h. After removal of solvent. The reaction mixture was concentrated under reduced pressure and purified by column chromatography (SiO$_2$, ethyl acetate/hexanes) to provide the desired product as white solid (0.14 g, 70%). 1H NMR (300 MHz, CDCl$_3$) δ 7.77 (ddd, J=0.94, 2.07, 8.10 Hz, 1H), 7.69 (t, J=2.35 Hz, 1H), 7.40 (t, J=8.19 Hz, 1H), 7.18 (ddd, J=0.75, 2.45, 8.29 Hz, 1H), 4.83 (tt, J=2.61, 5.58 Hz, 1H), 1.76-2.03 (m, 6H), 1.61-1.72 (m, 2H). MS (ESI) m/z for C$_{11}$H$_{13}$NO$_3$ [M+H]$^+$: calcd: 208.1; found: 208.2.

2-(3-Nitrophenyl)-1H-imidazole (70). To a solution of 3-nitrobenzonitrile (0.50 g, 3.37 mmol) in anhydrous methanol (17 ml) was added sodium methoxide (0.18 g, 3.37 mmol). The reaction mixture was stirred at room temperature for 5 h. Acid acetic (0.39 ml, 6.82 mmol) and aminoacetaldehyde dimethylacetal (0.37 ml, 3.37 mmol) were then added and the reaction mixture was heated at 70° C. with stirring for 1 h. After cooling to room temperature, methanol (2.25 ml) and 6N aqueous HCl (1.7 ml) solution were added to the reaction mixture. The reaction temperature was subsequently raised to 70° C. for 1 h. After cooling to room temperature, the solvent was removed under reduced pressure. Saturated aqueous potassium carbonate was added slowly until pH 8-10. The desired product precipitated and was collected by filtration as white solid (0.39 g, 61%). $^1$H NMR (300 MHz, CD$_3$OD) δ 7.21-7.27 (m, 1H), 6.66-6.77 (m, 2H), 6.13-6.24 (m, 1H), 5.64-5.73 (m, 2H). MS (ESI) m/z for C$_9$H$_7$N$_3$O$_2$[M+H]$^+$: calcd: 190.1; found: 190.3.

General Procedure B.

To a solution of nitrobenzene derivative (1 eq) in ethanol (0.1 M) was added hydrazine hydrate (15 eq). The reaction was stirred at 50° C. for 15 min and an excess of Raney nickel slurry in water (1.2 eq) was added slowly. After 1 h, the bubbling ceased, the mixture was cooled to room temperature and filtered through Celite. The filtrate was condensed under reduced pressured and the residue was either used for the next step without purification or purified by column chromatography (SiO$_2$, ethyl acetate/hexanes) to afford the desired product.

3-(6-Methoxypyridin-2-yl)aniline (12a) was prepared from 11a (0.23 g, 1.00 mmol) following the general procedure B as colorless liquid (0.20 g, quant. yield). $^1$H NMR (300 MHz, CDCl$_3$) δ 7.54 (dd, J=7.54, 8.10 Hz, 1H), 7.36-7.41 (m, 2H), 7.17-7.27 (m, 2H), 6.62-6.70 (m, 2H), 4.00 (s, 3H), 3.65-3.81 (m, 2H). MS (ESI) m/z for C$_{12}$H$_{12}$N$_2$O [M+H]$^+$: calcd: 201.1; found: 201.1.

3-(4-Methylpyridin-2-yl)aniline (12b) was prepared from 11 b (0.16 g, 0.73 mmol) following the general procedure B as yellow solid (0.10 g, 76%). $^1$H NMR (300 MHz, CDCl$_3$) δ 8.52 (d, J=3.96 Hz, 1H), 7.51 (s, 1H), 7.27 (d, J=5.09 Hz, 3H), 7.04 (d, J=3.58 Hz, 1H), 6.65 (br. s., 1H), 3.63 (br. s, 2H), 2.39 (s, 3H). MS (ESI) m/z for C$_{12}$H$_{12}$N$_2$[M+H]$^+$: calcd: 184.1; found: 184.4.

3-(2-Methoxypyridin-4-yl)aniline (12c) was prepared from 11c (0.30 g, 1.30 mmol) following the general procedure B as colorless liquid (0.17 g, 65%). $^1$H NMR (300 MHz, CDCl$_3$) δ 8.35 (d, J=2.07 Hz, 1H), 7.71-7.78 (m, 1H), 7.18-7.28 (m, 1H), 6.91 (td, J=1.25, 7.68 Hz, 1H), 6.76-6.85 (m, 2H), 6.67 (ddd, J=0.75, 2.26, 7.91 Hz, 1H), 3.97 (s, 3H), 3.34 (br. s., 2H). MS (ESI) m/z for C$_{12}$H$_{12}$N$_2$O [M+H]$^+$: calcd: 201.1; found: 201.2.

3-(Pyridin-2-yl)aniline (12d) was prepared from 11d (0.85 g, 4.24 mmol) following the general procedure B and the crude product was used for the next step without purification.

3-(Pyridin-4-yl)aniline (12e) was prepared from 11e (0.13 g, 0.65 mmol) following the general procedure B as white solid (0.07 g, 65%). $^1$H NMR (300 MHz, CDCl$_3$) δ 8.61-8.66 (m, 1H), 7.63-7.72 (m, 3H), 7.52-7.56 (m, 1H), 7.45-7.50 (m, 3H). MS (ESI) m/z for C$_{11}$H$_{10}$N$_2$ [M+H]$^+$: calcd: 171.1; found: 171.0.

3-(Pyrimidin-5-yl)aniline (12f) was prepared from 11f (0.10 g, 0.52 mmol) following the general procedure B as white solid (0.09 g, quant.). $^1$H NMR (300 MHz, CDCl$_3$) δ 9.19 (s, 1H), 8.90-8.94 (m, 2H), 7.26-7.33 (m, 1H), 6.95 (dd, J=0.85, 7.63 Hz, 1H), 6.86 (t, J=1.88 Hz, 1H), 6.78 (td, J=1.13, 8.10 Hz, 1H), 3.85 (br. s., 2H). MS (ESI) m/z for C$_{10}$H$_9$N$_3$ [M+H]$^+$: calcd: 172.1; found: 172.5.

3-(3-Methoxyphenyl)aniline (12g) was prepared from 11g (0.21 g, 0.92 mmol) following the general procedure B as colorless liquid (0.15 g, 82%). $^1$H NMR (300 MHz, CDCl$_3$) δ 7.28-7.35 (m, 1H), 7.17-7.23 (m, 1H), 7.14 (d, J=7.72 Hz, 1H), 7.09 (d, J=2.26 Hz, 1H), 6.97 (d, J=7.54 Hz, 1H), 6.84-6.90 (m, 2H), 6.65 (dd, J=1.51, 7.91 Hz, 1H), 3.83 (s, 3H), 3.70 (br. s., 2H). MS (ESI) m/z for C$_{13}$H$_{13}$NO [M+H]$^+$: calcd: 200.1; found: 200.2.

3-(3-Hydroxyphenyl)aniline (12h) was prepared from 11h (0.24 g, 1.12 mmol) following the general procedure B as white solid (0.11 g, 54%). $^1$H NMR (300 MHz, CDCl$_3$) δ 7.21-7.29 (m, 1H), 7.13-7.19 (m, 1H), 7.07 (d, J=7.16 Hz, 1H), 7.02 (s, 1H), 6.91 (d, J=6.78 Hz, 1H), 6.82 (d, J=1.51 Hz, 2H), 6.60 (d, J=5.46 Hz, 1H), 3.65 (br. s., 2H). MS (ESI) m/z for C$_{12}$H$_{11}$NO [M+H]$^+$: calcd: 185.1; found: 185.9.

3-[3-(Propan-2-yloxy)phenyl]aniline (12i) was prepared from 11i (0.30 g, 1.16 mmol) following the general procedure B. The crude was used for the next step without purification.

3-(4-Chlorophenyl)aniline (12j) was prepared from 1 j (0.22 g, 0.94 mmol) following the general procedure B as yellow solid (0.18 g, 94%). $^1$H NMR (300 MHz, CDCl$_3$) δ 7.41 (d, J=8.29 Hz, 2H), 7.24-7.35 (m, 3H), 7.14 (d, J=7.91 Hz, 1H), 6.85-6.94 (m, 1H), 6.62 (dd, J=1.41, 8.01 Hz, 1H), 3.66 (br. s, 2H). MS (ESI) m/z for C$_{12}$H$_{10}$ClN [M+H]$^+$: calcd: 204.1; found: 204.4.

3-(3,5-Dichlorophenyl)aniline (12k) was prepared from 11k (0.29 g, 1.09 mmol) following the general procedure B as colorless liquid (0.21 g, 82%). $^1$H NMR (300 MHz, CDCl$_3$) δ 7.42 (d, J=1.88 Hz, 2H), 7.31 (t, J=1.88 Hz, 1H), 7.19-7.23 (m, 1H), 6.89-6.94 (m, 1H), 6.81-6.84 (m, 1H), 6.68-6.74 (m, 1H), 3.76 (br. s., 2H). MS (ESI) m/z for C$_{12}$H$_9$Cl$_2$N [M+H]$^+$: calcd: 238.0; found: 238.3.

3-(3,4-Dichlorophenyl)aniline (12l) was prepared from 11l (0.18 g, 0.67 mmol) following the general procedure B as colorless liquid (0.14 g, 88%). $^1$H NMR (300 MHz, CDCl$_3$) δ 7.63 (d, J=1.70 Hz, 1H), 7.44-7.50 (m, 1H), 7.34-7.40 (m, 1H), 7.18-7.24 (m, 1H), 6.92 (d, J=7.72 Hz, 1H), 6.83 (s, 1H), 6.70 (dd, J=1.22, 7.82 Hz, 1H), 3.76 (br. s., 2H). MS (ESI) m/z for C$_{12}$H$_9$Cl$_2$N [M+H]$^+$: calcd: 238.0; found: 238.3.

3-(2,6-Dichlorophenyl)aniline (12m) was prepared from 11 m (0.26 g, 0.97 mmol) following the general procedure B as yellow solid (0.23 g, quant.). $^1$H NMR (300 MHz, CDCl$_3$) δ 7.38 (d, J=8.10 Hz, 2H), 7.24 (d, J=7.91 Hz, 2H), 6.69-6.78 (m, 1H), 6.64 (d, J=6.97 Hz, 1H), 6.57 (s, 1H), 3.72 (br. s., 2H). MS (ESI) m/z for C$_{12}$H$_9$Cl$_2$N [M+H]$^+$: calcd: 238.0; found: 238.1.

3-(4-Fluorophenyl)aniline (12n) was prepared from 11n (0.32 g, 1.47 mmol) following the general procedure B as yellow liquid (0.22 g, 80%). $^1$H NMR (300 MHz, CDCl$_3$) δ 7.21-7.54 (m, 3H), 7.09 (d, J=7.35 Hz, 1H), 6.99 (t, J=7.91 Hz, 1H), 6.82 (d, J=7.35 Hz, 1H), 6.72 (s, 1H), 6.55 (d, J=6.40 Hz, 1H), 3.60 (br. s., 2H). MS (ESI) m/z for C$_{12}$H$_{10}$FN [M+H]$^+$: calcd: 188.1; found: 188.1.

3-(2,4-Difluorophenyl)aniline (12o) was prepared from 11o (0.17 g, 0.71 mmol) following the general procedure B as colorless liquid (0.15 g, quant.). $^1$H NMR (300 MHz, CDCl$_3$) δ 7.30-7.41 (m, 1H), 7.16-7.25 (m, 1H), 6.75-6.95 (m, 4H), 6.67 (d, J=7.72 Hz, 1H), 3.69 (br. s., 2H). MS (ESI) m/z for C$_{12}$H$_9$F$_2$N [M+H]$^+$: calcd: 206.1; found: 206.2.

3-(4-tert-Butylphenyl)aniline (12p) was prepared from 11p (0.15 g, 0.53 mmol) following the general procedure B as yellow liquid (0.14 g, quant.). $^1$H NMR (300 MHz, CDCl$_3$) δ 7.40-7.46 (m, 2H), 7.33-7.39 (m, 2H), 7.14 (t, J=7.82 Hz, 1H), 6.92 (d, J=7.72 Hz, 1H), 6.83 (s, 1H), 6.59 (dd, J=1.41, 7.82 Hz, 1H), 3.64 (br. s., 2H), 1.28 (s, 10H). MS (ESI) m/z for C$_{16}$H$_{19}$N [M+H]$^+$: calcd: 226.2; found: 226.2.

3-(3,5-Di-tert-butylphenyl)aniline (12q) was prepared from 11q (0.22 g, 0.71 mmol) following the general procedure B as yellow oil (0.18 g, 91%). $^1$H NMR (300 MHz, CDCl$_3$) δ 7.35-7.43 (m, 3H), 7.18-7.23 (m, 1H), 6.99 (d, J=7.72 Hz, 1H), 6.90 (s, 1H), 6.67 (dd, J=1.32, 7.91 Hz, 1H), 3.26-4.11 (m, 2H), 1.37 (s, 18H). MS (ESI) m/z for C$_{20}$H$_{27}$N [M+H]$^+$: calcd: 282.2; found: 282.4.

3-(3-Phenylphenyl)aniline (12r) was prepared from 11r (0.27 g, 0.98 mmol) following the general procedure B as colorless liquid (0.18 g, 73%). MS (ESI) m/z for C$_{18}$H$_{15}$N [M+H]$^+$: calcd: 246.1; found: 246.3.

3-(4-Phenylphenyl)aniline (12s) was prepared from 11s (0.20 g, 0.73 mmol) following the general procedure B as yellow solid (0.18 g, quant.). $^1$H NMR (300 MHz, CDCl$_3$) δ 7.61-7.68 (m, 6H), 7.45 (t, J=7.44 Hz, 2H), 7.36 (d, J=7.16 Hz, 1H), 7.21-7.28 (m, 1H), 7.04 (d, J=7.72 Hz, 1H), 6.95 (d, J=1.88 Hz, 1H), 6.68 (dd, J=1.32, 7.91 Hz, 1H), 3.72 (br. s., 2H). MS (ESI) m/z for C$_{18}$H$_{15}$N [M+H]$^+$: calcd: 246.1; found: 246.2.

3-(4-Benzoylphenyl)aniline (12t) was prepared from 11t (0.18 g, 0.59 mmol) following the general procedure B as yellow solid (0.14 g, quant.). $^1$H NMR (300 MHz, CDCl$_3$) δ 7.72-7.83 (m, 4H), 7.59 (d, J=8.29 Hz, 2H), 7.51 (d, J=7.35 Hz, 1H), 7.43 (d, J=7.54 Hz, 1H), 7.14-7.20 (m, 1H), 6.96 (d, J=7.72 Hz, 1H), 6.85-6.89 (m, 1H), 6.62-6.69 (m, 1H), 3.65 (br. s., 2H). MS (ESI) m/z for C$_{19}$H$_{15}$NO [M+H]: calcd: 274.1; found: 274.2.

3-(1-Benzofuran-5-yl)aniline (12u) was prepared from 11u (0.20 g, 0.84 mmol) following the general procedure B as white solid (0.12 g, 66%). $^1$H NMR (300 MHz, CDCl$_3$) δ 7.75 (d, J=1.32 Hz, 1H), 7.63 (d, J=2.07 Hz, 1H), 7.45-7.55 (m, 2H), 7.18-7.26 (m, 1H), 6.98-7.03 (m, 1H), 6.91 (t, J=1.98 Hz, 1H), 6.78 (dd, J=0.66, 2.17 Hz, 1H), 6.66 (ddd, J=0.94, 2.31, 7.86 Hz, 1H), 3.71 (br. s., 2H). MS (ESI) m/z for C$_{14}$H$_{11}$NO [M+H]$^+$: calcd: 210.1; found: 210.2.

3-(Naphthalen-2-yl)aniline (12v) was prepared from 11v (0.26 g, 1.05 mmol) following the general procedure B as white solid (0.11 g, 46%). $^1$H NMR (300 MHz, CDCl$_3$) δ 8.00 (s, 1H), 7.84-7.91 (m, 3H), 7.71 (dd, J=1.60, 8.57 Hz, 1H), 7.44-7.50 (m, 2H), 7.26 (d, J=2.83 Hz, 1H), 7.12 (d, J=7.16 Hz, 1H), 7.04 (s, 1H), 6.71 (d, J=7.16 Hz, 1H). MS (ESI) m/z for C$_{16}$H$_{13}$N [M+H]$^+$: calcd: 220.1; found: 220.2.

3-(Quinolin-2-yl)aniline (12w) was prepared from 11w (0.02 g, 0.10 mmol) following the general procedure B as yellow solid (0.02 g, quant.). $^1$H NMR (300 MHz, CDCl$_3$) δ 8.21 (dd, J=5.84, 8.48 Hz, 2H), 7.80-7.87 (m, 2H), 7.73 (ddd, J=1.41, 6.97, 8.38 Hz, 1H), 7.58 (t, J=1.98 Hz, 1H), 7.52-7.56 (m, 1H), 7.45-7.51 (m, 1H), 7.31 (t, J=7.82 Hz, 1H), 6.77-6.82 (m, 1H), 3.46 (br. s., 2H). MS (ESI) m/z for C$_{15}$H$_{12}$N$_2$ [M+H]$^+$: calcd: 221.1; found: 221.2.

3-(Quinolin-3-yl)aniline (12x) was prepared from 11x (0.08 g, 0.33 mmol) following the general procedure B as yellow solid (0.07 g, quant.). $^1$H NMR (300 MHz, CDCl$_3$) δ 9.15 (d, J=2.26 Hz, 1H), 8.25 (d, J=2.07 Hz, 1H), 8.13 (d, J=8.29 Hz, 1H), 7.85 (d, J=8.10 Hz, 1H), 7.70 (ddd, J=1.41, 6.92, 8.43 Hz, 1H), 7.52-7.59 (m, 1H), 7.26-7.33 (m, 1H), 7.09 (dd, J=0.94, 7.72 Hz, 1H), 7.00 (t, J=1.98 Hz, 1H), 6.75 (ddd, J=0.75, 2.26, 7.91 Hz, 1H), 3.86 (br. s., 2H). MS (ESI) m/z for C$_{15}$H$_{12}$N$_2$ [M+H]$^+$: calcd: 221.1; found: 221.2.

3-(9H-Fluoren-2-yl)aniline (12y) was prepared from 11y (0.07 g, 0.26 mmol) following the general procedure B as white solid (0.05 g, 71%). $^1$H NMR (300 MHz, CDCl$_3$) δ 7.77-7.83 (m, 2H), 7.74 (d, J=0.75 Hz, 1H), 7.52-7.60 (m, 2H), 7.35-7.42 (m, 1H), 7.31 (dd, J=1.22, 7.44 Hz, 1H), 7.20-7.28 (m, 2H), 7.03-7.07 (m, 1H), 6.97 (t, J=1.98 Hz, 1H), 6.68 (ddd, J=0.75, 2.31, 7.86 Hz, 1H), 3.94 (s, 2H), 3.73 (br. s., 2H). MS (ESI) m/z for C$_{19}$H$_{15}$N [M+H]$^+$: calcd: 258.1; found: 258.2.

3-(Thiophen-2-yl)aniline (12z) was prepared from 11z (0.18 g, 0.89 mmol) following the general procedure B as yellow solid (0.10 g, 64%). $^1$H NMR (300 MHz, CDCl$_3$) δ 7.20-7.29 (m, 2H), 7.10-7.18 (m, 1H), 6.98-7.08 (m, 2H), 6.92 (s, 1H), 6.59 (dd, J=2.07, 7.91 Hz, 1H), 3.69 (br. s., 2H). MS (ESI) m/z for C$_{12}$H$_9$Cl$_2$N [M+H]$^+$: calcd: 238.0; found: 238.1.

3-(5-Methylthiophen-3-yl)aniline (12aa) was prepared from 11aa (0.09 g, 0.42 mmol) following the general procedure B as white solid (0.08 g, quant.). $^1$H NMR (300 MHz, CDCl$_3$) δ 7.12-7.17 (m, 2H), 6.93-7.02 (m, 2H), 6.87 (d, J=1.88 Hz, 1H), 6.59 (dd, J=1.51, 7.91 Hz, 1H), 3.68 (br. s., 2H), 2.50 (s, 3H). MS (ESI) m/z for C$_{11}$H$_{11}$NS [M+H]$^+$: calcd: 190.1; found: 190.2.

3-(5-Methylthiophen-2-yl)aniline (12ab) was prepared from 11ab (0.09 g, 0.42 mmol) following the general procedure B as colorless liquid (0.08 g, quant.). $^1$H NMR (300 MHz, CDCl$_3$) δ 7.09-7.16 (m, 1H), 7.05 (d, J=3.39 Hz, 1H), 6.93-6.99 (m, 1H), 6.86 (t, J=1.88 Hz, 1H), 6.67-6.72 (m, 1H), 6.56 (ddd, J=0.94, 2.26, 7.91 Hz, 1H), 3.65 (br. s., 2H), 2.48 (s, 2H). MS (ESI) m/z for C$_{11}$H$_{11}$NS [M+H]$^+$: calcd: 190.1; found: 190.3.

3-(1,3-Thiazol-5-yl)aniline (12ac) was prepared from 11ac (0.09 g, 0.46 mmol) following the general procedure B as colorless liquid (0.06 g, 73%). $^1$H NMR (300 MHz, CDCl$_3$) δ 8.72 (s, 1H), 8.03 (s, 1H), 7.13-7.23 (m, 1H), 6.97 (dd, J=0.94, 7.72 Hz, 1H), 6.88 (d, J=3.77 Hz, 1H), 6.66 (td, J=1.06, 8.05 Hz, 1H), 3.80 (br. s., 2H). MS (ESI) m/z for C$_9$H$_8$N$_2$S [M+H]$^+$: calcd: 177.1; found: 177.4.

3-(1,3-Thiazol-4-yl)aniline (12ad) was prepared from 11ad (0.12 g, 0.58 mmol) following the general procedure B as colorless liquid (0.06 g, 61%). $^1$H NMR (300 MHz, CDCl$_3$) δ 8.86 (d, J=1.88 Hz, 1H), 7.48 (d, J=1.88 Hz, 1H), 7.26-7.35 (m, 2H), 6.69 (dd, J=1.22, 2.35 Hz, 1H), 6.23 (dd, J=2.26, 7.91 Hz, 1H), 3.71 (br. s., 2H). MS (ESI) m/z for C$_9$H$_8$N$_2$S [M+H]$^+$: calcd: 177.1; found: 177.5.

3-(1,3-Thiazol-2-yl)aniline (12ae) was prepared from 11ae (0.08 g, 0.37 mmol) following the general procedure B as colorless liquid (0.03 g, 46%). $^1$H NMR (300 MHz, CDCl$_3$) δ 7.84 (d, J=3.39 Hz, 1H), 7.29-7.35 (m, 3H), 7.22 (t, J=8.01 Hz, 1H), 6.72-6.77 (m, 1H), 3.80 (br. s., 2H). MS (ESI) m/z for C$_9$H$_8$N$_2$S [M+H]$^+$: calcd: 177.1; found: 177.3.

4-[6-(Pyrrolidin-1-yl)pyridin-2-yl]aniline (56) was prepared from 55 (0.29 g, 1.06 mmol) following the general procedure B as colorless liquid (0.18 g, 71%). $^1$H NMR (300 MHz, CDCl$_3$) δ 7.84-7.95 (m, 2H), 7.44 (t, J=7.91 Hz, 1H), 6.91 (d, J=7.35 Hz, 1H), 6.68-6.78 (m, 2H), 6.22 (d, J=8.29 Hz, 1H), 3.75 (br. s., 2H), 3.53 (t, J=6.50 Hz, 4H), 1.96-2.04 (m, 4H). MS (ESI) m/z for C$_{15}$H$_{17}$N$_3$ [M+H]$^+$: calcd: 240.1; found: 240.3.

tert-Butyl 2-(3-aminophenyl)-1H-pyrrole-1-carboxylate (62) was prepared from 61 (0.147 g, 0.51 mmol) following the general procedure B as white solid (0.09 g, 65%). $^1$H NMR (300 MHz, CDCl$_3$) δ 7.21-7.37 (m, 1H), 7.06-7.18 (m, 1H), 6.70-6.78 (m, 1H), 6.57-6.68 (m, 2H), 6.18 (d, J=10.74 Hz, 2H), 3.63 (br. s., 2H), 1.37 (s, 9H). MS (ESI) m/z for C$_{15}$H$_{18}$N$_2$O$_2$ [M+H]$^+$: calcd: 259.1; found: 259.5.

3-(1H-Imidazol-2-yl)aniline (71) was prepared from 70 (0.30 g, 1.58 mmol) following the general procedure B as white solid (0.25 g, quant.). $^1$H NMR (300 MHz, CDCl$_3$) δ 7.05-7.23 (m, 5H), 6.69 (d, J=8.10 Hz, 1H), 3.74 (br. s., 2H). MS (ESI) m/z for C$_9$H$_9$N$_3$ [M+H]$^+$: calcd: 160.1; found: 160.2.

3-(Piperidin-1-yl)aniline (75a) was prepared from 74a (0.24 g, 1.16 mmol) following the general procedure B as colorless liquid (0.18 g, 88%). $^1$H NMR (300 MHz, CDCl$_3$) δ 7.00 (t, J=8.01 Hz, 1H), 6.35 (dd, J=1.79, 8.19 Hz, 1H), 6.22 (t, J=2.17 Hz, 1H), 6.11-6.16 (m, 1H), 3.55 (br. s., 2H), 3.09 (t, J=1.00 Hz, 4H), 1.66 (quin, J=5.51 Hz, 4H), 1.50-1.58 (m, 2H). MS (ESI) m/z for C$_{11}$H$_{16}$N$_2$[M+H]$^+$: calcd: 177.1; found: 177.5.

3-(Morpholin-4-yl)aniline (75b) was prepared from 74b (0.05 g, 0.22 mmol) following the general procedure B as white solid (0.04 g, 90%). MS (ESI) m/z for C$_{11}$H$_{16}$N$_2$[M+H]$^+$: calcd: 179.1; found: 179.5. $^1$H NMR (300 MHz, CDCl$_3$) δ 7.06 (t, J=8.29 Hz, 1H), 6.35 (dd, J=1.41, 8.19 Hz, 1H), 6.20-6.28 (m, 2H), 3.84 (t, J=4.90 Hz, 4H), 3.62 (br. s., 2H), 3.12 (t, J=4.90 Hz, 4H). MS (ESI) m/z for C$_{10}$H$_{14}$N$_2$O [M+H]$^+$: calcd: 178.1; found: 178.5.

3-(Pyrrolin-1-yl)aniline (75c) was prepared from 74c (0.13 g, 0.68 mmol) following the general procedure B as colorless liquid (0.10 g, 86%). $^1$H NMR (300 MHz, CDCl$_3$) δ 7.00 (t, J=8.01 Hz, 1H), 6.03 (dd, J=2.17, 8.01 Hz, 2H), 5.90 (t, J=1.98 Hz, 1H), 3.55 (br. s., 2H), 3.23 (t, J=6.59 Hz, 4H), 1.96 (td, J=3.34, 6.50 Hz, 4H). MS (ESI) m/z for C$_{10}$H$_{14}$N$_2$[M+H]$^+$: calcd: 163.1; found: 163.5.

3-(4-Methylpiperazin-1-yl)aniline (75d) was prepared from 74d (0.18 g, 0.82 mmol) following the general procedure B as white solid (0.12 g, 75%). $^1$H NMR (300 MHz, CDCl$_3$) δ 7.04 (t, J=8.01 Hz, 1H), 6.37 (dd, J=1.88, 8.10 Hz, 1H), 6.25 (t, J=2.07 Hz, 1H), 6.21 (dd, J=1.98, 7.82 Hz, 1H), 3.60 (br. s., 2H), 3.18 (t, J=4.90 Hz, 4H), 2.55 (t, J=5.10 Hz, 4H), 2.34 (s, 3H). MS (ESI) m/z for C$_{11}$H$_{17}$N$_3$[M+H]$^+$: calcd: 192.1; found: 192.4.

3-(Azetidin-1-yl)aniline (75e) was prepared from 74e (0.16 g, 0.87 mmol) following the general procedure B as colorless liquid (0.10 g, 80%). $^1$H NMR (300 MHz, CDCl$_3$) δ 6.98 (t, J=7.91 Hz, 7H), 6.07 (ddd, J=0.75, 2.07, 7.91 Hz, 7H), 5.89 (ddd, J=0.66, 2.07, 8.01 Hz, 7H), 5.76 (t, J=2.17 Hz, 7H), 3.82 (t, J=7.25 Hz, 30H), 3.52 (br. s., 8H), 2.30 (quin, J=7.21 Hz, 15H). MS (ESI) m/z for C$_9$H$_{12}$N$_2$ [M+H]$^+$: calcd: 149.1; found: 149.2.

N1,N1-Diethylbenzene-1,3-diamine (75j) was prepared from 74j (0.16 g, 0.87 mmol) following the general procedure B as colorless liquid (0.10 g, 80%). $^1$H NMR (300 MHz, CDCl$_3$) δ 6.99 (t, J=8.29 Hz, 1H), 6.11-6.16 (m, 1H), 6.00-6.04 (m, 2H), 3.53 (br. s., 1H), 3.30 (q, J=6.97 Hz, 4H), 1.14 (t, J=7.06 Hz, 6H). MS (ESI) m/z for C$_{10}$H$_{16}$N$_2$[M+H]$^+$: calcd: 165.1; found: 165.2.

3-(4,4-Difluoropiperidin-1-yl)aniline (75f) was prepared from 74f (0.07 g, 0.30 mmol) following the general procedure B as colorless liquid (0.07 g, quant.). $^1$H NMR (300 MHz, CDCl$_3$) δ 7.05 (t, J=7.91 Hz, 1H), 6.36 (td, J=1.13, 8.29 Hz, 1H), 6.20-6.28 (m, 2H), 3.62 (br. s., 2H), 3.64 (br. s, 2H), 3.32 (t, J=5.50 Hz, 4H), 2.06 (tt, J=5.91, 13.78 Hz, 4H). MS (ESI) m/z for C$_{11}$H$_{16}$N$_2$[M+H]$^+$: calcd: 177.1; found: 177.2.

3-[(1S,4S)-7-Azabicyclo[2.2.1]heptan-7-yl]aniline (75g) was prepared from 74g (0.02 g, 0.11 mmol) following the general procedure B as colorless liquid (0.03 g, quant.). $^1$H NMR (300 MHz, CDCl$_3$) δ 6.97 (t, J=8.01 Hz, 1H), 6.31 (td, J=1.11, 8.15 Hz, 1H), 6.23 (t, J=2.17 Hz, 1H), 6.15 (ddd, J=0.66, 2.12, 7.77 Hz, 1H), 4.12 (td, J=2.59, 4.62 Hz, 2H), 3.55 (br. s., 2H), 1.75-1.83 (m, 4H), 1.36-1.44 (m, 4H). MS (ESI) m/z for C$_{12}$H$_{16}$N$_2$[M+H]$^+$: calcd: 188.1; found: 188.2.

3-(Azepan-1-yl)aniline (75h) was prepared from 74h (0.11 g, 0.46 mmol) following the general procedure B as colorless liquid (0.06 g, 68%). $^1$H NMR (300 MHz, CDCl$_3$) δ 6.95-7.02 (m, 1H), 6.12-6.18 (m, 1H), 5.99-6.05 (m, 2H), 3.54 (br. s., 2H), 3.36-3.44 (m, 4H), 1.76 (dd, J=3.96, 5.09 Hz, 4H), 1.50-1.56 (m, 4H). MS (ESI) m/z for C$_{12}$H$_{18}$N$_2$ [M+H]$^+$: calcd: 191.1; found: 191.2.

3-{2-Oxa-6-azaspiro[3.3]heptan-6-yl}aniline (75i) was prepared from 74i (0.04 g, 0.16 mmol) following the general procedure B as white solid (0.04 g, quant.). $^1$H NMR (300 MHz, CDCl$_3$) 6.99 (t, J=7.91 Hz, 1H), 6.12 (ddd, J=0.75, 2.17, 7.82 Hz, 1H), 5.89 (ddd, J=0.75, 2.17, 8.01 Hz, 1H), 5.77 (t, J=2.17 Hz, 1H), 4.81 (s, 4H), 3.97 (s, 4H), 3.61 (br. s., 2H). MS (ESI) m/z for C$_{11}$H$_{14}$N$_2$O [M+H]$^+$: calcd: 191.1; found: 191.2.

1-[(3-Nitrophenyl)methyl]pyrrolidine (88). To a solution of 3-nitrobenzyl bromide (0.22 g, 1 mmol) in THF (7.5 ml) was added triethylamine (0.15 ml, 1 mmol) and pyrrolidine (0.17 ml, 2.05 mmol). The reaction mixture was refluxed for 2 h. The solvent was removed under reduced pressure and the residue was diluted with ethyl acetate, washed with water and brine. The organic layer was dried over anhydrous magnesium sulfate, filtered, and concentrated in vacuo to give the desired product as yellow liquid (0.21 g, quant.). $^1$H NMR (300 MHz, CDCl$_3$) δ 8.21 (s, 1H), 8.06-8.12 (m, 1H), 7.69 (d, J=7.54 Hz, 1H), 7.44-7.52 (m, 1H), 3.71 (s, 2H), 2.48-2.57 (m, 4H), 1.80 (td, J=3.23, 6.92 Hz, 4H). MS (ESI) m/z for C$_{11}$H$_{14}$N$_2$O$_2$ [M+H]$^+$: calcd: 207.1; found: 207.2.

3-(Pyrrolidin-1-ylmethyl)aniline (89). To a solution of 88 (0.19 g, 0.93 mmol) in ethanol was added 10% w/w Pd/C (0.012 g). The reaction mixture underwent hydrogenation in a Parr hydrogenator at 50 psi at room temperature for 1 h. The reaction mixture was then filtered through a Celite pad and concentrated in vacuo to provide the desired product as white solid (0.14 g, 88%). $^1$H NMR (300 MHz, CDCl$_3$) δ 7.07 (t, J=6.88 Hz, 1H), 6.63-6.79 (m, 2H), 6.42-6.60 (m, J=6.78 Hz, 1H), 4.81 (br. s., 2H), 3.58 (s, 2H), 2.40-2.74 (m, 4H), 1.66-1.94 (m, 4H). $^{13}$C NMR (75 MHz, CDCl$_3$) δ 146.6, 139.4, 129.1, 119.2, 115.7, 114.0, 60.3, 53.8, 23.4. MS (ESI) m/z for C$_{11}$H$_{16}$N$_2$[M+H]$^+$: calcd: 177.1; found: 177.2.

3-(Cyclopentyloxy)aniline (94) was prepared from 93 (0.10 g, 0.5 mmol) following the general procedure B as white solid (0.05 g, 58%). $^1$H NMR (300 MHz, CDCl$_3$) δ 7.03 (t, J=8.01 Hz, 1H), 6.23-6.32 (m, 2H), 6.20-6.23 (m, 1H), 4.67-4.74 (m, 1H), 3.62 (br. s., 2H), 1.74-1.91 (m, 6H), 1.55-1.64 (m, 2H). MS (ESI) m/z for C$_{11}$H$_{15}$NO [M+H]$^+$: calcd: 178.1; found: 178.2.

3-(1H-Pyrrol-2-yl)aniline (64). A solution of 62 (0.06 g, 0.23 mmol) in 5% aqueous potassium hydroxide (23 ml) was refluxed for 4 h. After cooling to room temperature, the mixture was poured into water and extracted with dichloromethane. The organic phase was dried with anhydrous magnesium sulfate, filtered, concentrated in vacuo to the desired product as white solid (0.03 g, 78%). $^1$H NMR (300 MHz, CDCl$_3$) δ 8.41 (br. s., 1H), 7.05-7.22 (m, 1H), 6.73-6.94 (m, 3H), 6.40-6.60 (m, 2H), 6.28 (s, 1H), 3.67 (br. s., 2H). MS (ESI) m/z for C$_{10}$H$_{10}$N$_2$[M+H]$^+$: calcd: 159.1; found: 159.

0.3-(1-Methyl-1H-pyrrol-2-yl)aniline (67). To a solution of 3-iodoaniline (0.24 ml, 2 mmol) in N,N-dimethylacetamide (8 ml) in a sealed tube was added N-methylpyrrole (0.36 ml, 8 mmol), potassium acetate (0.39 g, 8 mmol), and palladium (II) acetate (0.005 g, 0.02 mmol). The reaction mixture was stirred at 150° C. for 20 h. The reaction mixture was then diluted with ethyl acetate, washed three times with water and once with brine. The organic layer was dried with anhydrous magnesium sulfate, filtered, and concentrated under reduced pressure. The residue was purified by column chromatography (SiO$_2$, ethyl acetate/hexanes) to give the desired product was yellow liquid (0.08 g, 22%). $^1$H NMR (300 MHz, CDCl$_3$) δ 7.17 (t, J=7.82 Hz, 1H), 6.76-6.81 (m, 1H), 6.69 (td, J=2.10, 8.24 Hz, 2H), 6.61 (ddd, J=0.75, 2.31, 8.05 Hz, 1H), 6.16-6.21 (m, 2H), 3.68 (br. s., 2H), 3.64 (s, 3H). MS (ESI) m/z for C$_{11}$H$_{12}$N$_2$[M+H]$^+$: calcd: 173.1; found: 173.5.

General Procedure C.

To a solution of aryl amine (1 eq) in anhydrous chloroform (0.04 M) was added 4-chlorophenyl isocyanate (1 eq) at room temperature. The reaction mixture was then heated at 60° C. for 16 h. The precipitated product was filtered and thoroughly washed with dichloromethane.

3-(4-Chlorophenyl)-1-[3-(6-methoxypyridin-2-yl)phenyl]urea (15) was prepared from 12a (0.08 g, 0.5 mmol) following the general procedure C as white solid (0.14 g, 82%). $^1$H NMR (300 MHz, DMSO-d$_6$) δ 8.86 (d, J=3.96 Hz, 2H), 8.14-8.18 (m, 1H), 7.76-7.83 (m, 1H), 7.69 (d, J=8.10 Hz, 1H), 7.56 (d, J=9.42 Hz, 1H), 7.48-7.54 (m, 3H), 7.41 (d, J=7.91 Hz, 1H), 7.32-7.38 (m, 2H), 6.80 (d, J=8.29 Hz, 1H), 3.97 (s, 3H). $^{13}$C NMR (75 MHz, DMSO-d$_6$) δ 163.1, 153.6, 152.5, 140.0, 139.9, 138.9, 138.7, 129.1, 128.6, 125.3, 120.2, 119.8, 119.0, 116.4, 112.9, 109.3, 52.8. MS (ESI) m/z for C$_{19}$H$_{16}$ClN$_3$O$_2$[M+H]$^+$: calcd: 354.1; found: 354.3.

3-(4-Chlorophenyl)-1-[3-(4-methylpyridin-2-yl)phenyl]urea (16) was prepared from 12b (0.09 g, 0.55 mmol) following the general procedure C as white solid (0.12 g, 64%). $^1$H NMR (300 MHz, CDCl$_3$) δ 8.50 (d, J=5.09 Hz, 1H), 7.87 (s, 1H), 7.61 (d, J=7.54 Hz, 1H), 7.51 (s, 1H), 7.39 (td, J=7.91, 15.82 Hz, 2H), 7.20-7.24 (m, 4H), 7.07-7.16 (m, 3H), 2.41 (s, 3H). $^{13}$C NMR (75 MHz, CDCl$_3$) δ 157.0, 153.2, 149.1, 148.5, 140.4, 138.7, 136.9, 129.6, 129.0, 128.7, 123.6, 122.5, 122.1, 121.6, 121.3, 119.4, 21.2. MS (ESI) m/z for C$_{19}$H$_{17}$ClN$_3$O [M+H]$^+$: calcd: 338.1; found: 338.5.

3-(4-Chlorophenyl)-1-[3-(2-methoxypyridin-4-yl)phenyl]urea (17) was prepared from 12c (0.03 g, 0.15 mmol) following the general procedure C as white solid (0.03 g, 57%). $^1$H NMR (300 MHz, DMSO-d$_6$) δ 9.05 (br. s., 1H), 8.96 (br. s., 1H), 8.43 (s, 1H), 7.69-8.04 (m, 2H), 7.20-7.61 (m, 7H), 6.92 (d, J=7.54 Hz, 1H), 3.90 (br. s., 3H). $^{13}$C NMR (75 MHz, DMSO-d$_6$) δ 163.1, 152.5, 144.5, 140.2, 138.7, 137.6, 137.5, 129.4, 128.5, 125.3, 120.0, 119.8, 117.4, 116.2, 110.6, 53.2. MS (ESI) m/z for C$_{19}$H$_{16}$ClN$_3$O$_2$[M+H]$^+$: calcd: 353.1; found: 353.4.

3-(4-Chlorophenyl)-1-[3-(pyridin-2-yl)phenyl]urea (18) was prepared from 12d (0.05 g, 0.29 mmol) following the general procedure C as white solid (0.05 g, 53%). $^1$H NMR (300 MHz, DMSO-d$_6$) δ 8.89-8.96 (m, 2H), 8.67 (d, J=4.71 Hz, 1H), 8.25 (d, J=1.70 Hz, 1H), 7.87-7.91 (m, 1H), 7.67 (d, J=7.72 Hz, 1H), 7.45-7.55 (m, 4H), 7.30-7.38 (m, 4H). $^{13}$C NMR (75 MHz, DMSO-d$_6$) δ 155.9, 152.5, 149.5, 140.0, 139.3, 138.7, 138.5, 137.2, 129.1, 128.6, 125.3, 122.6, 120.2, 119.8, 119.0, 116.5. MS (ESI) m/z for C$_{18}$H$_{14}$ClN$_3$O [M+H]$^+$: calcd: 324.1; found: 324.2.

3-(4-Chlorophenyl)-1-[3-(pyridin-3-yl)phenyl]urea (19) was prepared from 14a (0.05 g, 0.29 mmol) following the general procedure C as white solid (0.05 g, 53%). $^1$H NMR (300 MHz, DMSO-d$_6$) δ 8.91 (br. s., 1H), 8.85 (br. s., 2H), 8.59 (d, J=2.83 Hz, 1H), 8.02 (d, J=7.35 Hz, 1H), 7.82 (br. s., 1H), 7.38-7.55 (m, 5H), 7.33 (d, J=7.35 Hz, 3H). $^{13}$C NMR (75 MHz, DMSO-d$_6$) δ 152.5, 148.5, 147.5, 140.3, 138.6, 137.7, 135.7, 134.1, 129.6, 128.6, 125.4, 123.9, 120.6, 119.8, 118.1, 116.7. MS (ESI) m/z for C$_{18}$H$_{14}$ClN$_3$O [M+H]$^+$: calcd: 324.1; found: 324.3.

3-(4-Chlorophenyl)-1-[3-(pyridin-4-yl)phenyl]urea (20) was prepared from 12e (0.03 g, 0.15 mmol) following the general procedure C as white solid (0.03 g, 33%). $^1$H NMR (300 MHz, DMSO-d$_6$) δ 8.92 (s, 1H), 8.89 (s, 1H), 8.65 (d, J=5.27 Hz, 2H), 7.93 (s, 1H), 7.65 (d, J=5.46 Hz, 2H), 7.46-7.54 (m, 3H), 7.43 (d, J=8.10 Hz, 2H), 7.34 (d, J=8.67 Hz, 2H). $^{13}$C NMR (75 MHz, DMSO-d$_6$) δ 152.5, 150.2, 147.1, 140.4, 138.6, 137.8, 129.7, 128.6, 125.4, 121.2, 120.5, 119.8, 119.1, 116.5. MS (ESI) m/z for C$_{18}$H$_{14}$ClN$_3$O [M+H]$^+$: calcd: 324.1; found: 324.1.

3-(4-Chlorophenyl)-1-[3-(pyrimidin-5-yl)phenyl]urea (21) was prepared from 12f (0.03 g, 0.15 mmol) following the general procedure C as white solid (0.03 g, 33%). $^1$H NMR (300 MHz, DMSO-d$_6$) δ 9.21 (s, 1H), 9.09 (s, 2H), 8.95 (d, J=19.21 Hz, 2H), 7.83 (s, 1H), 7.55 (s, 1H), 7.49-7.53 (m, 2H), 7.47 (s, 1H), 7.42 (s, 1H), 7.34 (d, J=8.85 Hz, 2H). $^{13}$C NMR (75 MHz, DMSO-d$_6$) δ 157.3, 154.6, 152.5, 140.4, 138.6, 134.4, 133.4, 129.8, 128.6, 125.5, 120.7, 119.8, 118.9, 116.7. MS (ESI) m/z for C$_{17}$H$_{13}$ClN$_4$O [M–H]$^-$: calcd: 323.1; found: 323.3.

3-(4-Chlorophenyl)-1-(3-phenylphenyl)urea (22) was prepared from 3-biphenylamine (0.05 g, 0.29 mmol) following the general procedure C as white solid (0.05 g, 53%). $^1$H NMR (300 MHz, DMSO-d$_6$) δ 8.91 (br. s., 1H), 8.86 (br. s., 1H), 7.80 (br. s., 1H), 7.62 (d, J=7.91 Hz, 2H), 7.44-7.54 (m, 4H), 7.29-7.42 (m, 5H), 7.27 (td, J=1.98, 4.33 Hz, 1H). $^{13}$C NMR (75 MHz, DMSO-d$_6$) δ 152.5, 140.8, 140.3, 140.1, 138.7, 129.3, 128.9, 128.6, 127.5, 126.6, 125.3, 120.4, 119.8, 117.4, 116.6. MS (ESI) m/z for C$_{17}$H$_{13}$ClN$_4$O [M–H]$^-$: calcd: 321.1; found: 321.2.

3-(4-Chlorophenyl)-1-[3-(3-methoxyphenyl)phenyl]urea (23) was prepared from 12g (0.02 g, 0.1 mmol) following the general procedure C as white solid (0.02 g, 57%). $^1$H NMR (300 MHz, DMSO-d$_6$) δ 8.88 (s, 1H), 8.82 (s, 1H), 7.76 (br. s., 1H), 7.49 (br. s., 2H), 7.22-7.44 (m, 6H), 7.16 (d, J=13.37 Hz, 2H), 6.95 (br. s., 1H), 3.82 (s, 3H). $^{13}$C NMR (75 MHz, DMSO-d$_6$) δ 159.7, 152.5, 141.8, 140.7, 140.0, 138.7, 130.0, 129.3, 128.6, 125.4, 120.5, 119.8, 119.0, 117.6, 116.7, 113.0, 112.2, 55.1. MS (ESI) m/z for C$_{20}$H$_{17}$ClN$_2$O$_2$ [M–H]$^-$: calcd: 351.1; found: 351.4.

3-(4-Chlorophenyl)-1-[3-(3-hydroxyphenyl)phenyl]urea (24) was prepared from 12h (0.02 g, 0.1 mmol) following the general procedure C as white solid (0.02 g, 44%). $^1$H NMR (300 MHz, DMSO-d$_6$) δ 8.95 (s, 1H), 8.90 (s, 1H), 7.51 (d, J=8.29 Hz, 1H), 7.18-7.38 (m, 4H), 6.98-7.10 (m, 2H), 6.90-6.97 (m, 1H), 6.74 (d, J=18.84 Hz, 2H), 6.54 (d, J=8.67 Hz, 1H), 5.14 (s, 1H). $^{13}$C NMR (75 MHz, DMSO-d$_6$) δ 157.7, 142.5, 141.6, 140.9, 140.0, 138.7, 129.9, 129.2, 128.6, 119.8, 117.2, 116.5, 115.1, 114.0, 113.3, 113.1, 112.1. MS (ESI) m/z for C$_{19}$H$_{15}$ClN$_2$O$_2$ [M–H]$^-$: calcd: 337.1; found: 337.5.

3-(4-Chlorophenyl)-1-[3-(3-isopropylphenyl)phenyl]urea (25) was prepared from 12i (0.03 g, 0.13 mmol) following the general procedure C as white solid (0.03 g, 60%). $^1$H NMR (300 MHz, DMSO-d$_6$) δ 8.90 (br. s., 1H), 8.82 (br. s., 1H), 7.77 (br. s., 1H), 7.46-7.54 (m, 2H), 7.29-7.43 (m, 5H), 7.26 (d, J=7.35 Hz, 1H), 7.15 (d, J=6.78 Hz, 1H), 7.09 (br. s., 1H), 6.93 (d, J=5.27 Hz, 1H), 4.60-4.78 (m, 1H), 1.30 (d, J=5.84 Hz, 6H). $^{13}$C NMR (75 MHz, DMSO-d$_6$) δ 157.9, 152.5, 141.8, 140.7, 140.1, 138.7, 130.0, 129.2, 128.5, 125.3, 120.4, 119.8, 118.8, 117.5, 116.7, 114.5, 114.0, 69.2, 21.8. MS (ESI) m/z for $C_{22}H_{21}ClN_2O_2$[M−H]⁻: calcd: 379.1; found: 379.3.

1-[3-(2H-1,3-Benzodioxol-5-yl)phenyl]-3-(4-chlorophenyl)urea (26) was prepared from 14b (0.09 g, 0.40 mmol) following the general procedure C as white solid (0.09 g, 59%). $^1$H NMR (300 MHz, DMSO-$d_6$) δ 8.73-8.90 (m, 2H), 7.71 (s, 1H), 7.44-7.56 (m, 3H), 7.28-7.39 (m, 4H), 7.07-7.23 (m, 2H), 6.98-7.03 (m, 1H), 6.07 (s, 2H). $^{13}$C NMR (75 MHz, DMSO-$d_6$) δ 152.5, 147.9, 146.8, 140.5, 139.9, 138.6, 134.6, 129.2, 128.6, 125.3, 120.2, 119.8, 117.1, 116.4, 108.6, 107.0, 101.1. MS (ESI) m/z for $C_{20}H_{15}ClN_2O_3$[M+H]: calcd: 367.1; found: 367.4.

3-(4-Chlorophenyl)-1-[3-(3-methylphenyl)phenyl]urea (27) was prepared from 14c (0.13 g, 0.82 mmol) following the general procedure C as white solid (0.11 g, 41%). $^1$H NMR (300 MHz, DMSO-$d_6$) δ 8.86 (s, 1H), 8.81 (s, 1H), 7.79 (s, 1H), 7.48-7.53 (m, 2H), 7.43 (s, 1H), 7.31-7.40 (m, 6H), 7.23-7.27 (m, 1H), 7.19 (d, J=7.16 Hz, 1H), 2.38 (s, 3H). $^{13}$C NMR (75 MHz, DMSO-$d_6$) δ 152.5, 140.9, 140.2, 140.0, 138.6, 138.0, 129.3, 128.8, 128.6, 128.1, 127.2, 125.4, 123.7, 120.4, 119.8, 117.4, 116.6, 21.1. MS (ESI) m/z for $C_{20}H_{17}ClN_2O$ [M+H]⁺: calcd: 337.1; found: 337.5.

3-(4-Chlorophenyl)-1-[3-(2-methylphenyl)phenyl]urea (28) was prepared from 14d (0.15 g, 0.82 mmol) following the general procedure C as white solid (0.11 g, 41%). $^1$H NMR (300 MHz, DMSO-$d_6$) δ 8.85 (s, 1H), 8.78 (s, 1H), 7.45-7.51 (m, 4H), 7.37 (d, J=3.77 Hz, 1H), 7.27-7.36 (m, 5H), 7.20 (d, J=4.71 Hz, 1H), 6.94 (d, J=7.16 Hz, 1H), 2.24 (s, 3H). $^{13}$C NMR (75 MHz, DMSO-$d_6$) δ 152.5, 141.8, 141.3, 139.3, 138.6, 138.5, 134.6, 130.3, 129.3, 128.6, 127.3, 125.9, 125.5, 125.3, 122.6, 119.8, 119.7, 118.9, 116.9, 20.1. MS (ESI) m/z for $C_{20}H_{17}ClN_2O$ [M−H]⁻: calcd: 357.1; found: 335.3.

3-(4-Chlorophenyl)-1-[3-(3-nitrophenyl)phenyl]urea (29) was prepared from 14e (0.04 g, 0.19 mmol) following the general procedure C as white solid (0.06 g, 82%). $^1$H NMR (300 MHz, DMSO-$d_6$) δ 8.88 (d, J=1.88 Hz, 2H), 8.37 (s, 1H), 8.22 (dd, J=1.70, 7.91 Hz, 1H), 8.09 (d, J=7.91 Hz, 1H), 7.88 (s, 1H), 7.77 (t, J=8.01 Hz, 1H), 7.43-7.50 (m, 4H), 7.36-7.42 (m, 1H), 7.33 (d, J=8.85 Hz, 2H). $^{13}$C NMR (75 MHz, DMSO-$d_6$) δ 152.5, 148.4, 141.8, 140.4, 138.6, 138.4, 133.1, 130.5, 129.7, 128.6, 125.5, 122.2, 120.9, 120.6, 119.8, 118.5, 116.7. MS (ESI) m/z for $C_{19}H_{14}ClN_3O_3$ [M−H]⁻: calcd: 366.1; found: 366.5.

3-(4-Chlorophenyl)-1-[3-(4-chlorophenyl)phenyl]urea (30) was prepared from 12j (0.05 g, 0.23 mmol) following the general procedure C as white solid (0.08 g, 94%). $^1$H NMR (300 MHz, DMSO-$d_6$) δ 9.02 (s, 1H), 8.98 (s, 1H), 7.86 (t, J=1.79 Hz, 1H), 7.78 (s, 1H), 7.56-7.69 (m, 2H), 7.53 (d, J=2.64 Hz, 1H), 7.50 (d, J=3.01 Hz, 1H), 7.45-7.48 (m, 1H), 7.41-7.45 (m, 1H), 7.35-7.40 (m, 1H), 7.32-7.35 (m, 1H), 7.31 (d, J=3.39 Hz, 1H), 7.27 (dd, J=1.51, 4.52 Hz, 1H). $^{13}$C NMR (75 MHz, DMSO-$d_6$) δ 152.5, 140.2, 139.5, 139.1, 138.6, 132.4, 129.4, 128.8, 128.6, 128.3, 125.4, 120.3, 119.8, 117.8, 116.5. MS (ESI) m/z for $C_{19}H_{14}Cl_2N_2O$ [M−H]⁻: calcd: 355.1; found: 355.3.

3-(4-Chlorophenyl)-1-[3-(3,5-dichlorophenyl)phenyl]urea (31) was prepared from 12k (0.03 g, 0.19 mmol) following the general procedure C as white solid (0.045 g, 91%). $^1$H NMR (300 MHz, DMSO-$d_6$) δ 8.91 (s, 1H), 8.88 (s, 1H), 7.83 (d, J=2.07 Hz, 1H), 7.79 (s, 1H), 7.68-7.73 (m, 1H), 7.58-7.64 (m, 1H), 7.43-7.52 (m, 3H), 7.38-7.42 (m, 2H), 7.27-7.37 (m, 4H). $^{13}$C NMR (75 MHz, DMSO-$d_6$) δ 152.5, 140.3, 138.6, 137.8, 134.6, 129.6, 128.9, 128.6, 126.9, 126.6, 125.3, 120.6, 119.9, 118.7, 116.8. MS (ESI) m/z for $C_{19}H_{13}Cl_3N_2O$ [M−H]⁻: calcd: 391.0; found: 390.9.

3-(4-Chlorophenyl)-1-[3-(3,4-dichlorophenyl)phenyl]urea (32) was prepared from 12l (0.03 g, 0.13 mmol) following the general procedure C as white solid (0.03 g, 61%). $^1$H NMR (300 MHz, DMSO-$d_6$) δ 8.98 (s, 1H), 8.92 (s, 1H), 7.82-7.90 (m, 2H), 7.69-7.76 (m, 1H), 7.62 (dd, J=1.88, 8.48 Hz, 1H), 7.53 (s, 2H), 7.48-7.56 (m, 2H), 7.38-7.46 (m, 2H), 7.29-7.37 (m, 3H). $^{13}$C NMR (75 MHz, DMSO-$d_6$) δ 152.5, 140.9, 140.3, 138.6, 138.1, 131.7, 131.0, 130.2, 129.5, 128.6, 128.3, 126.8, 125.4, 120.5, 119.8, 118.3, 116.6. MS (ESI) m/z for $C_{19}H_{13}Cl_3N_2O$ [M−H]⁻: calcd: 391.0; found: 390.9.

3-(4-Chlorophenyl)-1-[3-(2,6-dichlorophenyl)phenyl]urea (33) was prepared from 12m (0.02 g, 0.15 mmol) following the general procedure C as white solid (0.04 g, 69%). $^1$H NMR (300 MHz, DMSO-$d_6$) δ 8.86 (br. s., 2H), 7.59 (d, J=2.64 Hz, 2H), 7.37-7.53 (m, 7H), 7.28-7.36 (m, 2H), 6.80-6.92 (m, J=6.97 Hz, 1H). $^{13}$C NMR (75 MHz, DMSO-$d_6$) δ 152.4, 139.6, 138.8, 138.6, 136.9, 133.8, 130.1, 128.9, 128.6, 128.4, 125.4, 122.7, 119.8, 118.7, 118.0. MS (ESI) m/z for $C_{19}H_{13}Cl_3N_2O$ [M−H]⁻: calcd: 391.0; found: 391.1.

3-(4-Chlorophenyl)-1-[3-(4-fluorophenyl)phenyl]urea (34) was prepared from 12n (0.03 g, 0.16 mmol) following the general procedure C as white solid (0.05 g, 92%). $^1$H NMR (300 MHz, DMSO-$d_6$) δ 8.91 (s, 1H), 8.85 (s, 1H), 7.79 (s, 1H), 7.61-7.69 (m, 2H), 7.45-7.54 (m, 3H), 7.36-7.41 (m, 2H), 7.34 (s, 2H), 7.31 (d, J=3.01 Hz, 2H), 7.23-7.28 (m, 2H). $^{13}$C NMR (75 MHz, DMSO-$d_6$) δ 152.5, 140.1, 139.8, 138.7, 129.4, 128.9, 128.6, 128.6, 128.5, 126.6, 125.4, 120.4, 119.8, 117.4, 116.6, 115.8, 115.5. MS (ESI) m/z for $C_{19}H_{14}ClFN_2O$ [M−H]⁻: calcd: 339.1; found: 339.6.

3-(4-Chlorophenyl)-1-[3-(2,4-difluorophenyl)phenyl]urea (35) was prepared from 12o (0.04 g, 0.20 mmol) following the general procedure C as white solid (0.05 g, 66%). $^1$H NMR (300 MHz, DMSO-$d_6$) δ 8.95 (d, J=3.77 Hz, 2H), 7.75 (s, 1H), 7.61-7.69 (m, 1H), 7.52-7.60 (m, 3H), 7.47-7.52 (m, 1H), 7.43-7.47 (m, 1H), 7.37-7.42 (m, 2H), 7.23-7.32 (m, 1H), 7.20 (d, J=6.97 Hz, 1H). $^{13}$C NMR (75 MHz, DMSO-$d_6$) δ 152.4, 139.8, 138.6, 134.7, 131.9, 131.8, 131.7, 131.7, 129.1, 128.6, 125.4, 122.4, 119.8, 118.6, 117.8, 112.2, 112.1, 111.9, 111.8, 104.8, 104.5, 104.1. MS (ESI) m/z for $C_{19}H_{13}ClF_2N_2O$ [M−H]⁻: calcd: 357.1; found: 357.5.

3-(4-Chlorophenyl)-1-[3-(4-tert-butylphenyl)phenyl]urea (36) was prepared from 12p (0.01 g, 0.20 mmol) following the general procedure C as white solid (0.01 g, 48%). $^1$H NMR (300 MHz, DMSO-$d_6$) δ 8.93 (s, 1H), 8.86 (s, 1H), 7.75 (s, 1H), 7.46-7.58 (m, 6H), 7.30-7.43 (m, 4H), 7.25 (d, J=7.35 Hz, 1H), 1.32 (s, 9H). $^{13}$C NMR (75 MHz, DMSO-$d_6$) δ 152.5, 149.9, 140.7, 140.0, 138.7, 137.4, 129.3, 128.6, 126.3, 125.7, 125.3, 120.3, 119.8, 117.2, 116.4, 34.2, 31.1. MS (ESI) m/z for $C_{23}H_{23}ClN_2O$ [M−H]⁻: calcd: 377.2; found: 377.4.

3-(4-Chlorophenyl)-1-[3-(3,5-di-tert-butylphenyl)phenyl]urea (37) was prepared from 12q (0.06 g, 0.21 mmol) following the general procedure C as white solid (0.03 g, 54%). $^1$H NMR (300 MHz, DMSO-$d_6$) δ 8.86 (s, 1H), 8.82 (s, 1H), 7.61 (br. s., 1H), 7.50 (d, J=6.78 Hz, 3H), 7.31-7.44 (m, 6H), 7.22-7.27 (m, 1H), 1.34 (s, 18H). $^{13}$C NMR (75 MHz, DMSO-$d_6$) δ 152.5, 142.0, 140.0, 139.8, 138.7, 129.2, 128.6, 126.6, 125.3, 121.1, 120.9, 120.7, 119.7, 117.1, 116.9, 34.6, 31.3. MS (ESI) m/z for $C_{27}H_{31}ClN_2O$ [M−H]⁻: calcd: 433.2; found: 433.6.

3-(4-Chlorophenyl)-1-[3-(3-phenylphenyl)phenyl]urea (38) was prepared from 12r (0.11 g, 0.72 mmol) following the general procedure C as white solid (0.16 g, 56%). $^1$H NMR (300 MHz, DMSO-$d_6$) δ 8.89 (s, 1H), 8.83 (s, 1H), 7.86 (br. s., 2H), 7.75 (d, J=7.16 Hz, 2H), 7.61-7.69 (m, 2H), 7.58 (d, J=7.35 Hz, 1H), 7.47-7.54 (m, 4H), 7.36-7.46 (m, 4H), 7.33 (d, J=8.85 Hz, 2H). $^{13}$C NMR (75 MHz, DMSO-$d_6$) δ 152.5, 141.0, 140.7, 140.1, 140.1, 138.6, 129.6, 129.4, 128.9, 128.6, 127.6, 126.9, 125.9, 125.8, 125.4, 125.0, 120.7, 119.8, 117.6, 116.8. MS (ESI) m/z for $C_{25}H_{19}ClN_2O$ [M−H]$^-$: calcd: 397.1; found: 397.1.

3-(4-Chlorophenyl)-1-[3-(4-phenylphenyl)phenyl]urea (39) was prepared from 12s (0.01 g, 0.20 mmol) following the general procedure C as white solid (0.01 g, 48%). $^1$H NMR (300 MHz, DMSO-$d_6$) δ 8.93 (br. s., 1H), 8.88 (br. s., 1H), 7.88 (s, 1H), 7.70-7.84 (m, 6H), 7.47-7.58 (m, 4H), 7.40 (d, J=5.09 Hz, 3H), 7.31-7.38 (m, 3H). $^{13}$C NMR (75 MHz, DMSO-$d_6$) δ 152.5, 140.2, 140.2, 139.6, 139.2, 138.7, 129.4, 129.0, 128.6, 127.5, 127.2, 127.1, 126.6, 126.5, 125.4, 120.3, 119.8, 117.6, 116.5. MS (ESI) m/z for $C_{25}H_{19}ClN_2O$ [M−H]$^-$: calcd: 397.1; found: 397.0.

3-(4-Chlorophenyl)-1-[3-(4-benzoylphenyl)phenyl]urea (40) was prepared from 12t (0.03 g, 0.11 mmol) following the general procedure C as white solid (0.04 g, 81%). $^1$H NMR (300 MHz, DMSO-$d_6$) δ 8.87 (d, J=1.88 Hz, 2H), 7.88 (s, 1H), 7.79-7.86 (m, 4H), 7.74-7.78 (m, 2H), 7.66-7.72 (m, 1H), 7.54-7.62 (m, 2H), 7.46-7.51 (m, 2H), 7.43 (d, J=4.52 Hz, 2H), 7.36-7.41 (m, 1H), 7.32 (d, J=8.85 Hz, 2H). $^{13}$C NMR (75 MHz, DMSO-$d_6$) δ 195.3, 152.5, 144.3, 140.3, 139.6, 138.6, 137.2, 135.8, 132.6, 130.4, 129.6, 129.5, 128.6, 128.6, 126.7, 125.4, 120.7, 119.8, 118.3, 116.8. MS (ESI) m/z for $C_{26}H_{19}ClN_2O_2$ [M−H]$^-$: calcd: 425.1; found: 425.3.

1-[3-(1-Benzofuran-5-yl)phenyl]-3-(4-chlorophenyl)urea (41) was prepared from 12u (0.09 g, 0.55 mmol) following the general procedure C as white solid (0.12 g, 60%). $^1$H NMR (300 MHz, DMSO-$d_6$) δ 8.88 (s, 1H), 8.82 (s, 1H), 8.05 (d, J=2.07 Hz, 1H), 7.87 (d, J=5.84 Hz, 2H), 7.66-7.71 (m, 1H), 7.47-7.60 (m, 3H), 7.27-7.40 (m, 5H), 7.04 (d, J=1.32 Hz, 1H). $^{13}$C NMR (75 MHz, DMSO-$d_6$) δ 154.0, 152.5, 146.6, 141.2, 140.0, 138.7, 135.6, 129.3, 128.6, 127.9, 127.2, 125.4, 123.4, 120.7, 119.8, 119.2, 118.7, 117.0, 117.0, 111.5, 107.0. MS (ESI) m/z for $C_{21}H_{15}ClN_2O_2$ [M−H]$^-$: calcd: 361.1; found: 361.4.

3-(4-Chlorophenyl)-1-[3-(naphthalen-2-yl)phenyl]urea (42) was prepared from 12v (0.11 g, 0.68 mmol) following the general procedure C as white solid (0.14 g, 55%). $^1$H NMR (300 MHz, DMSO-$d_6$) δ 9.00 (d, J=6.40 Hz, 2H), 8.15 (s, 1H), 7.97-8.04 (m, 2H), 7.91-7.96 (m, 2H), 7.79 (dd, J=1.51, 8.67 Hz, 1H), 7.46-7.56 (m, 4H), 7.42 (s, 3H), 7.32 (d, J=8.85 Hz, 2H), 7.21 (d, J=8.85 Hz, 2H). $^{13}$C NMR (75 MHz, DMSO-$d_6$) δ 152.6, 140.6, 140.0, 138.5, 137.5, 133.2, 132.2, 129.5, 128.6, 128.5, 128.1, 127.4, 126.5, 126.2, 125.6, 125.1, 125.0, 120.9, 120.0, 117.7, 116.9. MS (ESI) m/z for $C_{23}H_{17}ClN_2O$ [M−H]$^-$: calcd: 371.1; found: 371.3.

3-(4-Chlorophenyl)-1-[3-(quinolin-2-yl)phenyl]urea (43) was prepared from 12w (0.01 g, 0.09 mmol) following the general procedure C as white solid (0.02 g, 59%). $^1$H NMR (300 MHz, DMSO-$d_6$) δ 8.96 (s, 1H), 8.87 (s, 1H), 8.46 (d, J=8.48 Hz, 1H), 8.32 (s, 1H), 8.04-8.09 (m, 1H), 8.00 (d, J=7.72 Hz, 1H), 7.75-7.86 (m, 2H), 7.55-7.64 (m, 2H), 7.46-7.52 (m, 2H), 7.33 (d, J=8.85 Hz, 2H). $^{13}$C NMR (75 MHz, DMSO-$d_6$) δ 156.1, 152.6, 147.4, 139.9, 139.3, 138.4, 137.3, 130.1, 129.4, 128.9, 128.6, 127.8, 126.9, 126.6, 125.6, 121.2, 120.1, 119.7, 118.8, 117.2. MS (ESI) m/z for $C_{22}H_{16}ClN_3O$ [M+H]$^+$: calcd: 374.1; found: 374.0.

3-(4-Chlorophenyl)-1-[3-(quinolin-3-yl)phenyl]urea (44) was prepared from 12x (0.05 g, 0.33 mmol) following the general procedure C as white solid (0.08 g, 63%). $^1$H NMR (300 MHz, DMSO-$d_6$) δ 9.21 (d, J=2.26 Hz, 1H), 8.94 (d, J=7.54 Hz, 2H), 8.60 (d, J=2.07 Hz, 1H), 8.04-8.13 (m, 2H), 7.98 (s, 1H), 7.79 (dt, J=1.51, 7.63 Hz, 1H), 7.63-7.70 (m, 1H), 7.46-7.55 (m, 5H), 7.36 (s, 2H). $^{13}$C NMR (75 MHz, DMSO-$d_6$) δ 152.5, 149.4, 146.9, 140.4, 138.6, 137.7, 132.9, 132.8, 129.7, 129.5, 128.6, 128.6, 128.4, 127.6, 127.0, 125.4, 120.9, 119.8, 118.2, 117.0. MS (ESI) m/z for $C_{22}H_{16}ClN_3O$ [M+H]$^+$: calcd: 374.1; found: 374.3.

3-(4-Chlorophenyl)-1-[3-(9H-fluoren-2-yl)phenyl]urea (45) was prepared from 12y (0.03 g, 0.18 mmol) following the general procedure C as white solid (0.05 g, 67%). $^1$H NMR (300 MHz, DMSO-$d_6$) δ 8.88 (s, 1H), 8.84 (s, 1H), 7.99 (d, J=7.91 Hz, 1H), 7.90-7.96 (m, 2H), 7.85 (s, 1H), 7.60-7.69 (m, 2H), 7.49-7.55 (m, 2H), 7.30-7.43 (m, 7H), 4.01 (s, 2H). $^{13}$C NMR (75 MHz, DMSO-$d_6$) δ 152.5, 143.8, 143.3, 141.1, 140.7, 140.5, 140.1, 138.9, 138.7, 129.3, 128.6, 126.8, 125.5, 125.4, 125.1, 123.3, 120.5, 120.4, 120.1, 119.8, 117.3, 116.6. MS (ESI) m/z for $C_{26}H_{19}ClN_2O$ [M−H]$^-$: calcd: 409.1; found: 409.5.

3-(4-Chlorophenyl)-1-[3-(furan-3-yl)phenyl]urea (46) was prepared from 14f (0.03 g, 0.16 mmol) following the general procedure C as white solid (0.05 g, 95%). $^1$H NMR (300 MHz, DMSO-$d_6$) δ 8.86 (s, 1H), 8.73 (s, 1H), 8.12 (s, 1H), 7.75 (t, J=1.70 Hz, 1H), 7.65 (s, 1H), 7.47-7.52 (m, 2H), 7.29-7.36 (m, 4H), 7.20-7.28 (m, 1H), 6.88 (d, J=0.94 Hz, 1H). $^{13}$C NMR (75 MHz, DMSO-$d_6$) δ 152.4, 144.2, 140.0, 139.2, 138.6, 132.4, 129.2, 128.6, 125.9, 125.4, 119.8, 119.5, 117.1, 115.5, 108.7. MS (ESI) m/z for $C_{17}H_{13}ClN_2O_2$ [M−H]$^-$: calcd: 311.1; found: 311.5.

3-(4-Chlorophenyl)-1-[3-(thiophen-3-yl)phenyl]urea (47) was prepared from 14g (0.03 g, 0.15 mmol) following the general procedure C as white solid (0.03 g, 63%). $^1$H NMR (300 MHz, DMSO-$d_6$) δ 8.85 (s, 1H), 8.76 (s, 1H), 7.75-7.79 (m, 2H), 7.63 (dd, J=2.92, 4.99 Hz, 1H), 7.45-7.51 (m, 3H), 7.30-7.36 (m, 5H). $^{13}$C NMR (75 MHz, DMSO-$d_6$) δ 152.5, 141.5, 140.0, 138.7, 135.7, 129.3, 128.6, 127.1, 126.1, 125.4, 120.9, 120.0, 119.8, 117.3, 116.0. MS (ESI) m/z for $C_{17}H_{13}ClN_2OS$ [M−H]$^-$: calcd: 327.0; found: 327.3.

3-(4-Chlorophenyl)-1-[3-(thiophen-2-yl)phenyl]urea (48) was prepared from 12z (0.10 g, 0.67 mmol) following the general procedure C as white solid (0.13 g, 57%). $^1$H NMR (300 MHz, DMSO-$d_6$) δ 8.84 (s, 2H), 7.82 (s, 1H), 7.55 (d, J=5.09 Hz, 1H), 7.50 (d, J=8.85 Hz, 2H), 7.44-7.47 (m, 1H), 7.28-7.36 (m, 5H), 7.14 (dd, J=3.67, 4.99 Hz, 1H). $^{13}$C NMR (75 MHz, DMSO-$d_6$) δ 152.4, 143.4, 140.2, 138.6, 134.2, 129.5, 128.6, 128.4, 125.6, 125.4, 123.6, 119.8, 119.1, 117.5, 115.1. MS (ESI) m/z for $C_{17}H_{13}ClN_2OS$ [M−H]$^-$: calcd: 327.0; found: 327.4.

3-(4-Chlorophenyl)-1-[3-(5-methylthiophen-3-yl)phenyl]urea (49) was prepared from 12aa (0.03 g, 0.17 mmol) following the general procedure C as white solid (0.04 g, 70%). $^1$H NMR (300 MHz, CD$_3$OD) δ 7.73 (br. s., 1H), 7.61 (d, J=7.54 Hz, 1H), 7.39-7.48 (m, 4H), 7.32-7.38 (m, 2H), 7.24-7.31 (m, 4H), 2.51 (s, 3H). $^{13}$C NMR (75 MHz, DMSO-$d_6$) δ 152.5, 141.1, 140.1, 140.0, 138.7, 135.9, 129.2, 128.6, 126.6, 125.4, 124.4, 119.8, 118.6, 117.1, 115.8, 15.0. MS (ESI) m/z for $C_{18}H_{15}ClN_2OS$ [M−H]$^-$: calcd: 341.1; found: 341.4.

3-(4-Chlorophenyl)-1-[3-(5-methylthiophen-2-yl)phenyl]urea (50) was prepared from 12ab (0.04 g, 0.19 mmol) following the general procedure C as white solid (0.05 g, 77%). $^1$H NMR (300 MHz, CD$_3$OD) δ 7.71 (s, 1H), 7.44 (d, J=8.85 Hz, 2H), 7.21-7.32 (m, 5H), 7.16 (d, J=3.58 Hz, 1H), 6.74 (d, J=2.64 Hz, 1H), 2.49 (s, 3H). $^{13}$C NMR (75 MHz, DMSO-$d_6$) δ 152.4, 141.0, 140.2, 139.0, 138.6, 134.5, 129.4, 128.6, 126.7, 125.4, 123.3, 119.8, 118.6, 117.1, 114.7, 15.0. MS (ESI) m/z for $C_{18}H_{15}ClN_2OS$ [M−H]$^-$: calcd: 341.1; found: 341.4.

3-(4-Chlorophenyl)-1-[3-(1,3-thiazol-5-yl)phenyl]urea (51) was prepared from 12ac (0.03 g, 0.16 mmol) following the general procedure C as white solid (0.04 g, 66%). $^1$H NMR (300 MHz, DMSO-d$_6$) δ 9.09 (s, 1H), 8.88 (s, 2H), 8.26 (s, 1H), 7.83 (s, 1H), 7.50 (d, J=8.85 Hz, 2H), 7.30-7.41 (m, 5H). $^{13}$C NMR (75 MHz, DMSO-d$_6$) δ 153.5, 152.4, 140.4, 139.2, 138.7, 138.5, 131.2, 129.7, 128.6, 125.5, 120.1, 119.9, 118.3, 116.4. MS (ESI) m/z for C$_{16}$H$_{12}$ClN$_3$OS [M−H]$^−$: calcd: 328.0; found: 328.4.

3-(4-Chlorophenyl)-1-[3-(1,3-thiazol-4-yl)phenyl]urea (52) was prepared from 12ad (0.03 g, 0.19 mmol) following the general procedure C as white solid (0.05 g, 74%). $^1$H NMR (300 MHz, DMSO-d$_6$) δ 9.20 (d, J=1.88 Hz, 1H), 8.85 (s, 2H), 8.12-8.15 (m, 1H), 8.11 (d, J=1.88 Hz, 1H), 7.59 (d, J=7.35 Hz, 1H), 7.48-7.53 (m, 2H), 7.31-7.45 (m, 5H). $^{13}$C NMR (75 MHz, DMSO-d$_6$) δ 155.0, 154.4, 152.4, 140.0, 138.7, 134.6, 129.2, 128.6, 125.3, 119.9, 119.8, 118.1, 116.2, 114.2. MS (ESI) m/z for C$_{16}$H$_{12}$ClN$_3$OS [M−H]$^−$: calcd: 328.0; found: 328.3.

3-(4-Chlorophenyl)-1-[3-(1,3-thiazol-2-yl)phenyl]urea (53) was prepared from 12ae (0.03 g, 0.16 mmol) following the general procedure C as white solid (0.04 g, 72%). $^1$H NMR (300 MHz, DMSO-d$_6$) δ 8.96 (s, 1H), 8.87 (s, 1H), 8.22 (s, 1H), 7.93 (d, J=3.20 Hz, 1H), 7.80 (d, J=3.01 Hz, 1H), 7.48-7.59 (m, 3H), 7.40-7.47 (m, 2H), 7.30-7.39 (m, 2H). $^{13}$C NMR (75 MHz, DMSO-d$_6$) δ 167.1, 152.4, 143.8, 140.3, 138.5, 133.6, 129.7, 128.6, 125.5, 120.4, 119.9, 119.8, 119.8, 115.7. MS (ESI) m/z for C$_{16}$H$_{12}$ClN$_3$OS [M−H]$^−$: calcd: 328.0; found: 328.4.

3-(4-Chlorophenyl)-1-{4-[6-(pyrrolidin-1-yl)pyridin-2-yl]phenyl}urea (57) was prepared from 56 (0.18 g, 0.75 mmol) following the general procedure C as light yellow solid (0.18 g, 62%). $^1$H NMR (300 MHz, DMSO-d$_6$) δ 8.98 (br. s., 2H), 8.01 (d, J=7.91 Hz, 2H), 7.44-7.65 (m, 5H), 7.34 (d, J=7.91 Hz, 2H), 7.05 (d, J=6.97 Hz, 1H), 6.31 (d, J=8.10 Hz, 1H), 3.44 (br. s., 4H), 1.80-2.08 (m, 4H). MS (ESI) m/z for C$_{22}$H$_{21}$ClN$_4$O [M−H]$^−$: calcd: 328.1; found: 328.4.

3-(4-Chlorophenyl)-1-(4-phenylphenyl)urea (59) was prepared from 58 (0.08 g, 0.5 mmol) following the general procedure C as white solid (0.08 g, 53%). $^1$H NMR (300 MHz, DMSO-d$_6$) δ 8.85 (br. s., 2H), 7.55-7.69 (m, 3H), 7.47 (d, J=6.03 Hz, 6H), 7.25-7.37 (m, 4H). $^{13}$C NMR (75 MHz, DMSO-d$_6$) δ 152.4, 139.8, 139.0, 138.5, 133.7, 128.8, 128.6, 127.0, 126.1, 125.5, 119.8, 119.7, 118.6. MS (ESI) m/z for C$_{17}$H$_{13}$ClN$_4$O [M−H]$^−$: calcd: 321.1; found: 321.2.

tert-Butyl 2-[3-({1-[(4-chlorophenyl)amino]ethenyl}amino)phenyl]-1H-pyrrole-1-carboxylate (63) was prepared from 62 (0.03 g, 0.10 mmol) following the general procedure C as white solid (0.04 g, 84%). $^1$H NMR (300 MHz, DMSO-d$_6$) δ 8.83 (s, 1H), 8.75 (s, 1H), 7.46-7.51 (m, 2H), 7.31-7.39 (m, 3H), 7.23-7.30 (m, 1H), 6.94 (d, J=7.54 Hz, 1H), 6.26-6.30 (m, 1H), 6.22-6.26 (m, 1H), 1.31 (s, 9H). $^{13}$C NMR (75 MHz, DMSO-d$_6$) δ 152.4, 148.8, 138.9, 138.6, 134.4, 134.2, 128.6, 128.0, 125.3, 122.5, 119.7, 118.6, 117.0, 114.1, 110.7, 83.5, 27.1. HRMS (ESI) m/z for C$_{22}$H$_{22}$ClN$_3$O$_3$[M+H]$^+$: calcd: 412.1422; found: 412.1423.

3-(4-Chlorophenyl)-1-[3-(1H-pyrrol-2-yl)phenyl]urea (65) was prepared from 64 (0.03 g, 0.18 mmol) following the general procedure C as white solid (0.05 g, 81%). $^1$H NMR (300 MHz, DMSO-d$_6$) δ 11.26 (br. s., 1H), 8.87 (br. s., 1H), 8.67 (br. s., 1H), 7.67 (s, 1H), 7.47-7.56 (m, 2H), 7.30-7.39 (m, J=5.70 Hz, 2H), 7.22-7.29 (m, 3H), 6.84 (s, 1H), 6.44 (s, 1H), 6.12 (s, 1H). $^{13}$C NMR (75 MHz, DMSO-d$_6$) δ 152.5, 139.8, 138.7, 133.6, 131.1, 129.0, 128.6, 125.3, 119.7, 119.3, 117.5, 115.9, 113.7, 109.0, 105.5. HRMS (ESI) m/z for C$_{17}$H$_{14}$ClN$_3$O [M+H]$^+$: calcd: 312.0898; found: 312.0894.

3-(4-Chlorophenyl)-1-[3-(1-methyl-1H-pyrrol-2-yl)phenyl]urea (68) was prepared from 67 (0.08 g, 0.45 mmol) following the general procedure C as white solid (0.14 g, 98%). $^1$H NMR (300 MHz, DMSO-d$_6$) δ 8.86 (s, 1H), 8.77 (s, 1H), 7.56 (s, 1H), 7.50 (d, J=8.85 Hz, 2H), 7.30-7.36 (m, 4H), 7.03-7.08 (m, 1H), 6.83 (t, J=2.17 Hz, 1H), 6.15 (dd, J=1.88, 3.58 Hz, 1H), 6.04-6.08 (m, 1H), 3.66 (s, 3H). $^{13}$C NMR (75 MHz, DMSO-d$_6$) δ 152.5, 139.6, 138.6, 133.4, 128.8, 128.6, 125.4, 124.3, 121.6, 119.8, 117.8, 116.6, 108.3, 107.3, 34.9. HRMS (ESI) m/z for C$_{18}$H$_{16}$ClN$_3$O [M+H]$^+$: calcd: 326.1055; found: 326.1049.

3-(4-Chlorophenyl)-1-[3-(1H-imidazol-2-yl)phenyl]urea (72) was prepared from 71 (0.13 g, 0.82 mmol) following the general procedure C as white solid (0.22 g, 86%). $^1$H NMR (300 MHz, DMSO-d$_6$) δ 12.52 (br. s., 1H), 8.84 (d, J=11.30 Hz, 2H), 8.07 (br. s., 1H), 7.52 (br. s., 3H), 7.44 (br. s., 1H), 7.34 (d, J=7.16 Hz, 3H), 7.03-7.20 (m, 2H). $^{13}$C NMR (75 MHz, DMSO-d$_6$) δ 152.4, 145.5, 139.8, 138.7, 131.4, 129.1, 128.6, 125.4, 119.7, 118.6, 118.0, 115.1. HRMS (ESI) m/z for C$_{16}$H$_{13}$ClN$_4$O [M+H]$^+$: calcd: 313.0851; found: 313.0846.

3-(4-Chlorophenyl)-1-[3-(piperidin-1-yl)phenyl]urea (76) was prepared from 75a (0.09 g, 0.6 mmol) following the general procedure C as white solid (0.17 g, 81%). $^1$H NMR (300 MHz, DMSO-d$_6$) δ 8.74 (s, 1H), 8.54 (s, 1H), 7.48 (d, J=8.85 Hz, 2H), 7.31 (d, J=8.85 Hz, 2H), 7.14 (s, 1H), 7.08 (t, J=8.10 Hz, 1H), 6.76 (d, J=7.91 Hz, 1H), 6.55 (dd, J=1.60, 8.19 Hz, 1H), 3.10 (t, J=1.00 Hz, 4H), 1.57-1.68 (m, J=4.10 Hz, 4H), 1.54 (t, J=1.00 Hz, 2H). $^{13}$C NMR (75 MHz, DMSO-d$_6$) δ 152.4, 152.1, 140.1, 138.8, 129.0, 128.5, 125.2, 119.6, 109.9, 108.8, 105.9, 49.6, 25.2, 23.9. MS (ESI) m/z for C$_{18}$H$_{20}$ClN$_3$O [M+H]$^+$: calcd: 330.8; found: 330.3.

1-(4-Chlorophenyl)-3-[3-(morpholin-4-yl)phenyl]urea (77) was prepared from 75b (0.03 g, 0.2 mmol) following the general procedure C as white solid (0.05 g, 72%). $^1$H NMR (300 MHz, DMSO-d$_6$) δ 8.77 (s, 1H), 8.59 (s, 1H), 7.48 (d, J=9.04 Hz, 2H), 7.31 (d, J=8.85 Hz, 2H), 7.15 (s, 1H), 7.08-7.13 (m, 1H), 6.82 (d, J=7.72 Hz, 1H), 6.59 (dd, J=1.60, 8.19 Hz, 1H), 3.74 (t, J=9.20 Hz, 4H), 3.07 (t, J=4.70 Hz, 4H). $^{13}$C NMR (75 MHz, DMSO-d$_6$) δ 152.4, 151.6, 140.2, 138.7, 129.1, 128.5, 125.2, 119.7, 109.5, 109.3, 105.1, 66.1, 48.5. MS (ESI) m/z for C$_{17}$H$_{18}$ClN$_3$O$_2$[M+H]$^+$: calcd: 332.1; found: 332.5.

1-(4-Chlorophenyl)-3-[3-(pyrrolidin-1-yl)phenyl]urea (78) was prepared from 75c (0.09 g, 0.58 mmol) following the general procedure C as white solid (0.16 g, 86%). $^1$H NMR (300 MHz, DMSO-d$_6$) δ 8.71 (s, 1H), 8.51 (s, 1H), 7.47 (d, J=8.85 Hz, 2H), 7.31 (d, J=8.85 Hz, 2H), 7.03 (t, J=8.01 Hz, 1H), 6.74 (s, 1H), 6.64 (d, J=7.91 Hz, 1H), 6.18 (dd, J=1.51, 8.10 Hz, 1H), 3.19 (t, J=6.22 Hz, 4H), 1.94 (t, J=6.31 Hz, 4H). $^{13}$C NMR (75 MHz, DMSO-d$_6$) δ 152.3, 148.2, 140.2, 138.8, 129.1, 128.5, 125.1, 119.6, 106.0, 105.7, 101.6, 47.2, 24.9. MS (ESI) m/z for C$_{17}$H$_{18}$ClN$_3$O [M+H]: calcd: 316.1; found: 316.2.

1-(4-Chlorophenyl)-3-[3-(4-methylpiperazin-1-yl)phenyl]urea (79) was prepared from 75d (0.06 g, 0.36 mmol) following the general procedure C as white solid (0.09 g, 67%). $^1$H NMR (300 MHz, DMSO-d$_6$) δ 8.76 (s, 1H), 8.57 (s, 1H), 7.48 (d, J=8.85 Hz, 2H), 7.31 (d, J=8.85 Hz, 2H), 7.15 (s, 1H), 7.09 (t, J=8.19 Hz, 1H), 6.76-6.81 (m, 1H), 6.57 (dd, J=1.79, 8.19 Hz, 1H), 3.11 (t, J=4.70 Hz, 3H), 2.46 (t, J=4.70 Hz, 3H), 2.22 (s, 3H). $^{13}$C NMR (75 MHz, DMSO-d$_6$) δ 152.4, 151.5, 140.2, 138.7, 129.1, 128.5, 125.2, 119.7, 109.1, 105.4, 54.6, 48.1, 45.7. MS (ESI) m/z for C$_{18}$H$_{21}$ClN$_4$O [M+H]$^+$: calcd: 345.1; found: 345.0.

3-[3-(Azetidin-1-yl)phenyl]-1-(4-chlorophenyl)urea (80) was prepared from 75e (0.10 g, 0.69 mmol) following the general procedure C as white solid (0.09 g, 44%). $^1$H NMR (300 MHz, DMSO-d$_6$) δ 8.71 (s, 1H), 8.55 (s, 1H), 7.47 (d, J=8.85 Hz, 2H), 7.31 (d, J=9.04 Hz, 2H), 7.01-7.07 (m, 1H), 6.65 (d, J=1.88 Hz, 1H), 6.64 (d, J=2.26 Hz, 1H), 3.77 (t, J=7.16 Hz, 4H), 2.29 (quin, J=7.16 Hz, 2H). $^{13}$C NMR (75 MHz, DMSO-d$_6$) δ 152.6, 152.3, 140.1, 138.7, 129.0, 128.5, 125.2, 119.6, 107.2, 105.2, 101.0, 51.8, 16.3. MS (ESI) m/z for C$_{16}$H$_{16}$ClN$_3$O [M+H]$^+$: calcd: 302.1; found: 302.2.

3-(4-Chlorophenyl)-1-[3-(4,4-difluoropiperidin-1-yl)phenyl]urea (81) was prepared from 75f (0.04 g, 0.28 mmol) following the general procedure C as white solid (0.08 g, 78%). $^1$H NMR (300 MHz, DMSO-d$_6$) δ 8.78 (s, 1H), 8.59 (s, 1H), 7.48 (d, J=8.85 Hz, 2H), 7.32 (d, J=8.85 Hz, 2H), 7.21 (s, 1H), 7.12 (t, J=8.10 Hz, 1H), 6.82 (d, J=7.91 Hz, 1H), 6.64 (dd, J=1.88, 8.10 Hz, 1H), 3.26-3.33 (m, J=5.27 Hz, 4H), 1.97-2.14 (m, 4H). $^{13}$C NMR (75 MHz, DMSO-d$_6$) δ 152.4, 150.2, 140.3, 138.7, 129.3, 128.5, 125.2, 119.7, 110.2, 109.7, 106.2, 45.8, 45.8, 45.7, 33.1, 32.8, 32.5. MS (ESI) m/z for C$_{18}$H$_{18}$ClF$_2$N$_3$O [M+H]$^+$: calcd: 366.1; found: 366.2.

3-(4-Chlorophenyl)-1-{3-[(1S,4S)-7-azabicyclo[2.2.1]heptan-7-yl]phenyl}urea (82) was prepared from 75g (0.02 g, 0.1 mmol) following the general procedure C as white solid (0.01 g, 28%). $^1$H NMR (300 MHz, CDCl$_3$) δ 7.21-7.23 (m, 2H), 7.08-7.12 (m, 2H), 6.89-6.93 (m, 2H), 6.59-6.67 (m, 2H), 4.08-4.13 (m, 2H), 1.71-1.79 (m, 4H), 1.40 (d, J=7.16 Hz, 4H). $^{13}$C NMR (75 MHz, CDCl$_3$) δ 153.5, 149.5, 138.4, 136.8, 130.1, 129.0, 128.7, 121.5, 113.0, 112.4, 109.9, 58.0, 28.7. MS (ESI) m/z for C$_{19}$H$_{20}$ClN$_3$O [M+H]$^+$: calcd: 342.1; found: 342.4.

1-[3-(Azepan-1-yl)phenyl]-3-(4-chlorophenyl)urea (83) was prepared from 75h (0.05 g, 0.31 mmol) following the general procedure C as white solid (0.09 g, 82%). $^1$H NMR (300 MHz, DMSO-d$_6$) δ 8.70 (s, 1H), 8.48 (s, 1H), 7.47 (d, J=8.85 Hz, 2H), 7.31 (d, J=8.67 Hz, 2H), 7.01 (t, J=8.10 Hz, 1H), 6.90 (s, 1H), 6.59 (d, J=7.91 Hz, 1H), 6.31 (dd, J=1.79, 8.19 Hz, 1H), 3.41 (t, J=5.84 Hz, 4H), 1.63-1.82 (m, 4H), 1.38-1.52 (m, 4H). $^{13}$C NMR (75 MHz, DMSO-d$_6$) δ 152.4, 148.8, 140.4, 138.8, 129.3, 128.5, 125.1, 119.6, 105.5, 105.3, 101.1, 48.7, 26.9, 26.4. MS (ESI) m/z for C$_{19}$H$_{22}$ClN$_3$O [M+H]$^+$: calcd: 344.1; found: 344.4.

3-(4-Chlorophenyl)-1-(3-{2-oxa-6-azaspiro[3.3]heptan-6-yl}phenyl)urea (84) was prepared from 75i (0.03 g, 0.16 mmol) following the general procedure C as white solid (0.04 g, 68%). $^1$H NMR (300 MHz, DMSO-d$_6$) δ 8.72 (s, 1H), 8.58 (s, 1H), 7.47 (d, J=8.85 Hz, 2H), 7.31 (d, J=8.85 Hz, 2H), 7.05 (t, J=8.29 Hz, 1H), 6.64-6.70 (m, 2H), 6.03-6.09 (m, 1H), 4.72 (s, 4H), 3.94 (s, 4H). $^{13}$C NMR (75 MHz, DMSO-d$_6$) δ 152.3, 151.9, 140.1, 138.7, 129.0, 128.5, 125.2, 119.6, 107.6, 105.6, 101.4, 79.9, 60.9, 38.4. MS (ESI) m/z for C$_{18}$H$_{18}$ClN$_3$O$_2$[M+H]$^+$: calcd: 344.1; found: 344.2.

1-(4-Chlorophenyl)-3-[3-(dimethylamino)phenyl]urea (85) was prepared from 3-(N,N-dimethylamino)aniline hydrochloride (0.11 g, 0.5 mmol) following the general procedure C as white solid (0.13 g, 92%). $^1$H NMR (300 MHz, CDCl$_3$) δ 7.28-7.34 (m, 2H), 7.18-7.24 (m, 2H), 6.76 (s, 1H), 6.70 (t, J=2.26 Hz, 1H), 6.53-6.60 (m, 2H), 6.43 (s, 1H), 2.96 (s, 6H). MS (ESI) m/z for C$_{15}$H$_{16}$ClN$_3$O [M+H]$^+$: calcd: 290.1; found: 290.2.

3-(4-Chlorophenyl)-1-[3-(diethylamino)phenyl]urea (86) was prepared from 75j (0.03 g, 0.18 mmol) following the general procedure C as white solid (0.04 g, 69%). $^1$H NMR (300 MHz, DMSO-d$_6$) δ 8.70 (s, 1H), 8.49 (s, 1H), 7.47 (d, J=9.04 Hz, 2H), 7.31 (d, J=8.85 Hz, 2H), 7.02 (t, J=8.10 Hz, 1H), 6.86 (t, J=2.07 Hz, 1H), 6.60 (d, J=7.91 Hz, 1H), 6.30 (dd, J=2.26, 8.10 Hz, 1H), 3.25-3.32 (m, 4H), 1.09 (t, J=6.97 Hz, 6H). MS (ESI) m/z for C$_{17}$H$_{20}$ClN$_3$O [M+H]$^+$: calcd: 318.1; found: 318.4.

3-(4-Chlorophenyl)-1-[3-(pyrrolidin-1-ylmethyl)phenyl]urea (90) was prepared from 89 (0.06 g, 0.33 mmol) following the general procedure C as white solid (0.08 g, 73%). $^1$H NMR (300 MHz, CDCl$_3$) δ 9.16 (s, 1H), 9.01 (s, 1H), 7.67 (s, 1H), 7.48 (d, J=8.85 Hz, 2H), 7.35 (d, J=7.91 Hz, 1H), 7.20 (d, J=8.67 Hz, 2H), 6.99-7.12 (m, 2H), 4.00 (s, 2H), 3.10-3.27 (m, 4H), 2.02-2.09 (m, 4H). $^{13}$C NMR (75 MHz, CDCl$_3$) δ 153.4, 140.6, 137.9, 129.8, 129.6, 128.7, 127.4, 123.7, 120.2, 120.0, 58.8, 53.5, 23.1). MS (ESI) m/z for C$_{18}$H$_{20}$ClN$_3$O [M+H]$^+$: calcd: 330.1; found: 330.4.

3-(4-Chlorophenyl)-1-(3-methoxyphenyl)urea (91) was prepared from 3-methoxyaniline (0.16 g, 1 mmol) following the general procedure C as white solid (0.25 g, 91%). $^1$H NMR (300 MHz, DMSO-d$_6$) δ 8.79 (s, 1H), 8.71 (s, 1H), 7.48 (d, J=8.85 Hz, 2H), 7.32 (d, J=8.85 Hz, 1H), 7.14-7.22 (m, 2H), 6.93 (dd, J=1.13, 8.10 Hz, 1H), 6.56 (dd, J=1.88, 8.10 Hz, 1H), 3.73 (s, 3H). $^{13}$C NMR (75 MHz, DMSO-d$_6$) δ 159.7, 152.3, 140.7, 138.6, 129.5, 128.6, 125.3, 119.7, 110.6, 107.4, 104.1, 54.9. MS (ESI) m/z for C$_{14}$H$_{13}$ClN$_2$O$_2$ [M+H]$^+$: calcd: 277.1; found: 277.2.

3-(4-Chlorophenyl)-1-[3-(cyclopentyloxy)phenyl]urea (95) was prepared from 94 (14200-122) (0.05 g, 0.29 mmol) following the general procedure C as white solid (0.08 g, 84%). $^1$H NMR (300 MHz, DMSO-d$_6$) δ 8.79 (s, 1H), 8.67 (s, 1H), 7.48 (d, J=8.85 Hz, 2H), 7.32 (d, J=8.85 Hz, 2H), 7.16 (dd, J=2.92, 4.99 Hz, 2H), 6.87 (dd, J=1.13, 8.10 Hz, 1H), 6.51 (dd, J=2.07, 8.10 Hz, 1H), 4.75 (t, J=5.65 Hz, 1H), 1.83-1.97 (m, 2H), 1.66-1.76 (m, 4H), 1.51-1.62 (m, 2H). $^{13}$C NMR (75 MHz, DMSO-d$_6$) δ 158.0, 152.3, 140.6, 138.6, 129.4, 128.6, 125.3, 119.7, 110.3, 108.9, 105.6, 78.5, 32.3, 23.5. MS (ESI) m/z for C$_{18}$H$_{19}$ClN$_2$O$_2$[M+H]$^+$: calcd: 331.1; found: 331.2

BIOLOGICAL DATA

CB1 Calcium Mobilization Assay.

CHO-RD-HGA16 cells (Molecular Devices, CA) stably expressing the human CB1 receptor were plated into 96-well black-walled assay plates at 25,000 cells/well in 100 μL of Ham's F12 (supplemented with 10% fetal bovine serum, 100 units of penicillin/streptomycin, and 100 μg/mL Normocin) and incubated overnight at 37° C., 5% CO$_2$. Calcium 5 dye (Molecular Devices, CA) was reconstituted according to the manufacturer's instructions. The reconstituted dye was diluted 1:40 in prewarmed (37° C.) assay buffer (1×HBSS, 20 mM HEPES, 2.5 mM probenecid, pH 7.4 at 37° C.). Growth medium was removed, and the cells were gently washed with 100 μL of prewarmed (37° C.) assay buffer. The cells were incubated for 45 min at 37° C., 5% CO$_2$ in 200 μL of the diluted Calcium 5 dye solution. For antagonist assays to determine IC$_{50}$ values, the EC$_{80}$ concentration of CP55,940 was prepared at 10× the desired final concentration in 0.25% BSA/0.5% DMSO/0.5% EtOH/assay buffer, aliquoted into 96-well polypropylene plates, and warmed to 37° C. Serial dilutions of the test compounds were prepared at 10× the desired final concentration in 2.25% BSA/4.5% DMSO/4.5% EtOH/assay buffer. After the dye loading incubation period, the cells were pretreated with 25 μL of the test compound serial dilutions and incubated for 15 min at 37° C. After the pretreatment incubation period, the plate was read with a FLIPR Tetra (Molecular Devices, CA). Calcium-mediated changes in fluorescence were monitored every 1 s over a 90 s time period, with the Tetra adding 25 μL of the CP55,940 EC$_{80}$ concentration at the 10s time point (excitation/emission: 485/525 nm). Relative fluorescence units (RFU) were plotted against the log of compound concentrations. Data were fit to a three-parameter logistic curve to generate $IC_{50}$ values (GraphPad Prism 6.0, CA). For the modulation experiments, the above procedure was followed except that cells were pretreated with a single concentration of test compound (prepared at 10× the desired concentration in 2.25% BSA/4.5% DMSO/4.5% EtOH/assay buffer) and the Tetra added serial dilutions of CP55,940 (prepared at 10× the desired concentration in 0.25% BSA/ 0.5% DMSO/0.5% EtOH/assay buffer). For agonist screens, the above procedure was followed except that cells were pretreated with 2.25% BSA/4.5% DMSO/4.5% EtOH/assay buffer and the Tetra added single concentration dilutions of the test compounds prepared at 10× the desired final concentration in 0.25% BSA/0.5% DMSO/0.5% EtOH/assay buffer. Test compound RFUs were compared to the CP55, 940 $E_{max}$ RFUs to generate % $E_{max}$ values.

CB2 Calcium Mobilization Assay.

This assay was performed in a similar manner to the CB1 calcium mobilization assay described above except that the cells used were CHO-RD-HGA16 (Molecular Devices, CA) cells stably expressing the human CB2 receptor which were seeded into at 30,000 cells/well in 96-well plates. Preincubation with Calcium 5 dye and treatment with CP55,940 and test compounds were carried out as described in the CB1 assay. Calcium-mediated fluorescence changes were monitored every 1.52 s over a 60 s time period, with the Tetra adding 25 µL of the CP55,940 $EC_{80}$ concentration at the 19 s time point (excitation/emission: 485/525 nm). The collected data was processed as described above for the CB1 assay.

[$^{35}$S]GTP-γ-S Binding Assay.

Cerebella from adult male CD-1 mice were dissected on ice, snap frozen, and stored at −80° C. until the day of the experiment. Cerebella were homogenized by polytron in membrane buffer (50 mM Tris, 3 mM $MgCl_2$, 0.2 mM EGTA, 100 mM NaCl, pH 7.4) on ice, centrifuged for 10 min at 40,000×g at 4° C. The supernatant was discarded and the pellet was suspended in membrane buffer, homogenized, and centrifuged again for 10 min at 40,000×g. The pellet was resuspended in membrane buffer and protein quantified by Bradford method. Membranes were preincubated in assay buffer (membrane buffer containing 1 mg/ml bovine serum albumin; BSA) for 10 min with 3 units/ml adenosine deaminase then incubated for 60 min at 30° C. with 30 µM GDP and 0.1 nM [$^{35}$S]GTP-γ-S. Non-specific binding was determined by adding 30 µM unlabeled GTP-γ-S. Serial dilutions of test compounds were done in 100% DMSO with final assay DMSO concentration of 0.1%. Inhibition curves for test compounds were normalized to CP55,940 (100 nM) stimulation in the absence of test compound (i.e. vehicle=100%) and were fit to 3 parameter non-linear regression, with bottom and top constrained to >0 and =100 respectively. $pIC_{50}$ values were considered significantly different when 95% confidence intervals did not overlap.

Metabolic stability assessment was performed by Paraza Pharma Inc. (Montreal, Canada).

Compounds were incubated with rat liver microsomes at 37° C. for a total of 45 minutes. The reaction was performed at pH 7.4 in 100 mM potassium phosphate buffer containing 0.5 mg/mL of rat liver microsomal protein. Phase I metabolism was assessed by adding NADPH to a final concentration of 1 mM and collecting samples at time points 0, 5, 15, 30 and 45 minutes. All collected samples were quenched 1:1 with ice-cold stop solution (1 µM labetalol and 1 µM glyburide in acetonitrile), and centrifuged to remove precipitated protein. Resulting supernatants were further diluted 1:4 with acetonitrile:water (1:1). Samples were analyzed by LC/MS/MS and calculations for half-life, and in-vitro clearance were accomplished using Microsoft Excel (2007).

Reinstatement of Extinguished Cocaine-Seeking Behavior.

Animals: Adult male Sprague-Dawley rats (Harlan, Indianapolis, Ind.) weighing 280-300 g were used in the study. Animals were housed individually on a 12/12 hr light/dark cycle (behavioral experiments were conducted during the light period) with free access to water and food except during experimental sessions. Animals were maintained and experiments conducted in accordance with the Institutional Animal Care and Use Committee, University at Buffalo, and with the 2011 Guide for the Care and Use of Laboratory Animals (Institute of Laboratory Animal Resources on Life Sciences, National Research Council, National Academy of Sciences, Washington D.C.).

Drug self-administration, extinction and reinstatement: The reinstatement procedure was described in detail elsewhere[37, 38]. Briefly, rats were surgically implanted with a chronic indwelling jugular catheter. After one-week recovery, rats were trained to press the active lever (left lever) for infusion of cocaine (0.75 mg/kg/inf) under a fixed ratio [FR] schedule (starting FR=1, which was increased to FR 5 within 5 training sessions) schedule during daily 2-hr sessions for 14 days. Reinforcer deliveries were accompanied by the presentation of a stimulus light over the active lever followed by a 30-s time-out period during which lever presses had no programmed consequence. Following acquisition of cocaine self-administration, extinction of drug-seeking behavior took place during 2-hr daily sessions in which lever pressing produced no consequence. All other conditions remained unchanged. After 7 days of extinction, all rats reached the extinction criteria (total responses less than 20% of the training sessions).

Drug-induced reinstatement test was conducted on the day following the last extinction session. Rats were pretreated with vehicle, compounds 2 (15, 30 mg/kg) or 34 (10 mg/kg) 10 min prior to a priming injection of cocaine (10 mg/kg, i.p.) administered immediately before the start of the reinstatement session.

Data analyses: Data are expressed as mean±S.E.M. Differences in active lever responding between the last extinction session and reinstatement session were determined with paired t tests (within subjects comparison). The effects of compounds 2 on reinstatement were analyzed by a one-way analysis of variance (ANOVA) followed by post hoc Bonferroni's test (between subjects comparison). The effects of compounds 34 on reinstatement was analyzed by Student's t test. $P<0.05$ was considered statistically significant.

Biological Evaluations in Calcium Mobilization Assays.

The FLIPR-based calcium mobilization assays were used as the primary screen to assess the potency of the synthesized diarylureas at CB1 and CB2 receptors as described previously.

In these assays, CHO cells that overexpress the promiscuous Gα16 protein were engineered to stably express the CB1 or CB2 receptor. Compounds were evaluated for their ability to decrease the mobilization of intracellular calcium levels stimulated by CP55,940. The $IC_{50}$ values of the synthesized compounds against the $EC_{80}$ of CP55,940 (100 nM) were determined (Tables 1 and 2).

TABLE 1
Allosteric modulatory activities of diarylureas 15-53, 63, 65, 68, 72, 76-86, 90-91, and 95 in the CB1 calcium mobilization assay and [$^{35}$S]GTP-γ-S binding assay.
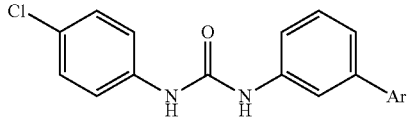
|  |  | CB1 calcium assay | | [$^{35}$S]GTP-γ-S binding assay IC$_{50}$ (nM)$^c$ |
|---|---|---|---|---|
| Compound | Ar | IC$_{50}$ (nM)$^a$ | Agonist screen $^b$ (% CP55, 940 E$_{max}$) |  |
| B | 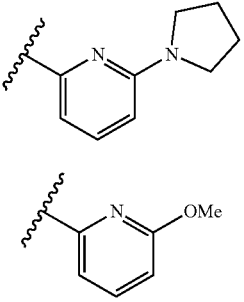 | 33 ± 8 | 28.2 ± 4.8 | 102 (79-135) |
| 15 | 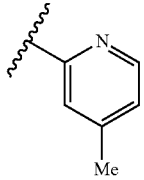 [SMILES: *c1cc(C)ccn1] | 231 ± 14 | 2.4 ± 0.2 | ND$^d$ |
| 16 | 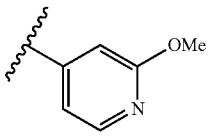 [SMILES: *c1ccnc(OC)c1] | 1310 ± 80 | 2.9 ± 0.1 | ND$^d$ |
| 17 | 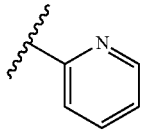 [SMILES: *c1ccccn1] | 133 ± 6 | 23.4 ± 1.9 | 1320 (871-1,990) |
| 18 | 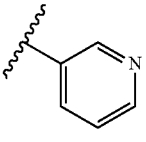 | 47 ± 13 | 8.8 ± 3.1 | 2648 (1584-4425) |
| 19 | 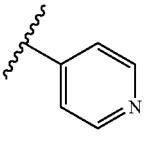 | 244 ± 45 | 34.2 ± 9.3 | ND$^d$ |
| 20 | 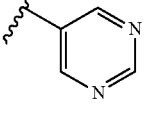 | 178 ± 38 | 14.5 ± 2.5 | 407 (295-562) |
| 21 |  | 290 ± 24 | 2.5 ± 6.2 | ND$^d$ |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

[Structure: 4-chlorophenyl-NH-C(=O)-NH-phenyl-Ar (3-substituted)]

| Compound | Ar | CB1 calcium assay IC$_{50}$ (nM)[a] | Agonist screen[b] (% CP55,940 E$_{max}$) | [$^{35}$S]GTP-γ-S binding assay IC$_{50}$ (nM)[c] |
|---|---|---|---|---|
| 22 | phenyl | 32 ± 7 | 5.1 ± 0.8 | 437 (214-912) |
| 23 | 3-OMe-phenyl | 81 ± 10 | 12.5 ± 1.9 | 827 (590-1,160) |
| 24 | 3-OH-phenyl | 840 ± 130 | 9.8 ± 1.6 | ND[d] |
| 25 | 3-OiPr-phenyl | 141 ± 24 | 25.2 ± 5.3 | ND[d] |
| 26 | 3,4-methylenedioxyphenyl | 70 ± 14 | 9.8 ± 3.5 | 619 (497-771) |
| 27 | 3-Me-phenyl | 74 ± 6 | 8.1 ± 2.3 | 456 (310-671) |
| 28 | 2-Me-phenyl | 190 ± 45 | 4.4 ± 2.7 | ND[d] |
| 29 | 3-NO$_2$-phenyl | 27 ± 2 | 17.0 ± 3.3 | 452 (321-635) |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

[Structure: 4-chlorophenyl-NH-C(=O)-NH-3-substituted-phenyl-Ar]

| Compound | Ar | CB1 calcium assay IC$_{50}$ (nM)[a] | Agonist screen[b] (% CP55,940 E$_{max}$) | [$^{35}$S]GTP-γ-S binding assay IC$_{50}$ (nM)[c] |
|---|---|---|---|---|
| 30 | 4-Cl-phenyl | 95 ± 9 | 21.3 ± 3.7 | ND[d] |
| 31 | 3,5-diCl-phenyl | 22 ± 2 | 15.5 ± 2.4 | 299 (151-592) |
| 32 | 3,4-diCl-phenyl | 30 ± 4 | 10.4 ± 2.1 | 464 (259-830) |
| 33 | 2,6-diCl-phenyl | 338 ± 19 | 17.2 ± 3.1 | ND[d] |
| 34 | 4-F-phenyl | 23 ± 2 | 8.8 ± 1.1 | 151 (65-355) |
| 35 | 2,4-diF-phenyl | 18 ± 1 | 2.4 ± 6.2 | 353 (236-528) |
| 36 | 4-tBu-phenyl | 591 ± 48 | 4.0 ± 1.0 | ND[d] |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

| Compound | Ar | CB1 calcium assay IC$_{50}$ (nM)[a] | Agonist screen [b] (% CP55,940 E$_{max}$) | [$^{35}$S]GTP-γ-S binding assay IC$_{50}$ (nM)[c] |
|---|---|---|---|---|
| 37 | 3,5-di-tBu-phenyl | 460 ± 39 | 10.4 ± 2.1 | ND[d] |
| 38 | 3-biphenyl | 195 ± 40 | 0.5 ± 0.2 | 559 (383-817) |
| 39 | 4-biphenyl | 1340 ± 370 | −0.7 ± 2.4 | ND[d] |
| 40 | 4-benzoylphenyl | 1570 ± 60 | 12.9 ± 1.7 | ND[d] |
| 41 | benzofuran-5-yl | 134 ± 13 | 0.2 ± 1.0 | 265 (216-326) |
| 42 | naphthalen-2-yl | 132 ± 28 | 6.9 ± 0.5 | 1520 (1,120-2,070) |
| 43 | quinolin-2-yl | 334 ± 80 | 4.5 ± 0.7 | 1890 (1,360-2,640) |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

| Compound | Ar | CB1 calcium assay IC$_{50}$ (nM)[a] | Agonist screen[b] (% CP55, 940 E$_{max}$) | [$^{35}$S]GTP-γ-S binding assay IC$_{50}$ (nM)[c] |
|---|---|---|---|---|
| 44 | 3-quinolinyl | 516 ± 70 | 2.6 ± 1.2 | 651 (476-891) |
| 45 | 2-fluorenyl | 1260 ± 160 | −0.1 ± 0.1 | ND[d] |
| 46 | 3-furyl | 41 ± 9 | 18.6 ± 1.0 | 440 (339-574) |
| 47 | 3-thienyl | 36 ± 1 | 28.9 ± 0.6 | 164 (113-239) |
| 48 | 2-thienyl | 67 ± 6 | 12.8 ± 1.8 | 573 (272-1205) |
| 49 | 5-methyl-3-thienyl | 40 ± 4 | 3.7 ± 1.7 | 776 (324-1858) |
| 50 | 5-methyl-2-thienyl | 42 ± 6 | 4.6 ± 1.4 | 372 (182-759) |
| 51 | 5-thiazolyl | 94 ± 9 | 8.1 ± 3.1 | 331 (215-509) |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

| Compound | Ar | CB1 calcium assay IC$_{50}$ (nM)$^a$ | Agonist screen$^b$ (% CP55, 940 E$_{max}$) | [$^{35}$S]GTP-γ-S binding assay IC$_{50}$ (nM)$^c$ |
|---|---|---|---|---|
| 52 | thiazol-4-yl | 84 ± 6 | 8.6 ± 4.4 | 250 (118-530) |
| 53 | thiazol-2-yl | 154 ± 14 | 20.1 ± 1.1 | 1258 (562-2,818) |
| 63 | N-Boc-pyrrol-2-yl | 3444 ± 451 | 11.0 ± 1.4 | 3,236 (1,480-7,070) |
| 65 | pyrrol-2-yl | 169 ± 34 | 13.7 ± 0.1 | 40 (29-55) |
| 68 | N-methylpyrrol-2-yl | 165 ± 14 | 3.4 ± 2.9 | 665 (501-883) |
| 72 | imidazol-2-yl | 529 ± 98 | 4.3 ± 0.5 | 343 (224-524) |
| 76 | piperidin-1-yl | 174 ± 31 | 1.1 ± 0 | ND$^d$ |
| 77 | morpholin-4-yl | 360 ± 64 | 12.4 ± 1.8 | ND$^d$ |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

| Compound | Ar | CB1 calcium assay IC$_{50}$ (nM)[a] | Agonist screen[b] (% CP55, 940 E$_{max}$) | [$^{35}$S]GTP-γ-S binding assay IC$_{50}$ (nM)[c] |
|---|---|---|---|---|
| 78 | pyrrolidine | 40 ± 4 | 0.6 ± 0.5 | ND[d] |
| 79 | 4-methylpiperazine | 2,885 ± 543 | 27.6 ± 2.0 | ND[d] |
| 80 | azetidine | 35 ± 5 | 21.6 ± 0.7 | 1381 (603-3,159) |
| 81 | 4,4-difluoropiperidine | 92 ± 9 | 14.0 ± 0.6 | ND[d] |
| 82 | cyclohexyl-N | 2,698 ± 305 | 5.5 ± 1.3 | ND[d] |
| 83 | azepane | 350 ± 37 | 18.6 ± 1.1 | ND[d] |
| 84 | 2-oxa-6-azaspiro[3.3]heptane | 792 ± 43 | 28.8 ± 0.2 | >10,000 |
| 85 | N(CH$_3$)$_2$ | 113 ± 19 | 14.5 ± 4.9 | ND[d] |
| 86 | N(Et)$_2$ | 297 ± 37 | 20.9 ± 0.2 | ND[d] |

TABLE 1-continued

Allosteric modulatory activities of diarylureas 15-53, 63, 65, 68, 72, 76-86, 90-91, and 95 in the CB1 calcium mobilization assay and [$^{35}$S]GTP-γ-S binding assay.

| | | CB1 calcium assay | | |
|---|---|---|---|---|
| Compound | Ar | IC$_{50}$ (nM)$^a$ | Agonist screen $^b$ (% CP55, 940 E$_{max}$) | [$^{35}$S]GTP-γ-S binding assay IC$_{50}$ (nM)$^c$ |
| 90 | (CH$_2$-pyrrolidinyl) | >10,000 | 27.5 ± 4.5 | ND$^d$ |
| 91 | OMe | 520 ± 36 | 13.6 ± 2.4 | ND$^d$ |
| 95 | (O-cyclopentyl) | 277 ± 36 | 11.7 ± 1.4 | ND$^d$ |

$^a$Against EC$_{80}$ (100 nM) of CP55, 940. Values are the mean ± S.E.M. of at least three independent experiments in duplicate.
$^b$ Agonist screen at 10,000 nM final concentration. Values are the mean ± SD of at least two independent experiments in duplicate.
$^c$Values are expressed as mean (95% confidence interval) from at least three independent experiments in duplicate.
$^d$ND: Not determined.

TABLE 2

Allosteric modulatory activities of diarylureas 55 and 59 in the CB1 calcium mobilization assay

| | | CB1 calcium assay | |
|---|---|---|---|
| Compound | Ar | IC$_{50}$ (nM)$^a$ | Agonist screen $^b$ (% CP55, 940 E$_{max}$) |
| 57 | (6-OMe-pyridin-2-yl) | 219 ± 50 | 23 ± 5 |
| 59 | (phenyl) | 66 ± 9 | 21 ± 4 |

$^a$Against EC$_{80}$ (100 nM) of CP55, 940. Values are the mean ± S.E.M. of at least three independent experiments in duplicate.
$^b$ Agonist screen at 10,000 nM final concentration. Values are the mean ± SD of at least two independent experiments in duplicate.

As illustrated, a number of compounds that showed good potency in the calcium mobilization assay were then evaluated for the potency in antagonizing agonist-stimulated [$^{35}$S]GTP-γ-S binding to CB1 receptor in mouse cerebellar membranes. CB1 receptor agonist CP55,940 was employed as the agonist probe. Similar to PSNCBAM-1 (B), the present diarylureas dose-dependently decreased [$^{35}$S]GTP-γ-S binding level as expected for CB1 negative allosteric modulators.

Metabolic Stability of Select Diarylureas

TABLE 3

Stability of select diarylureas in rat liver microsomes

| Compound | Half-life (min)$^a$ | Clearance (μl/min/mg)$^a$ |
|---|---|---|
| B (PSN) | 13.4 ± 4.1 | 113.7 ± 34.4 |
| 20 | 41.9 ± 1.3 | 33.1 ± 1.0 |
| 34 | >300 | <4.6 |

$^b$ Values are expressed as mean ± S.E.M. from two independent experiments.

Metabolism affects a drug's clearance and duration of action (half-life) and a drug must have sufficient stability to reach the action sites and elicit their designated effects. Therefore, the metabolic stability of select compounds (B, 20, 34) were evaluated in rat liver microsomes.

Table 3 lists the half-lives (T$_1$/2) and clearance (CL) of certain tested compounds. B was rapidly metabolized with T$_{1/2}$=13.4 min, suggesting modest stability in first pass metabolism. The metabolic stability increased by ~3 fold for compound 20 (T$_{1/2}$=41.9 min). Significant improvement in the metabolic stability is demonstrated by compound 34, which had a half-life of more than 300 min and clearance of less than 4.6 μl/min/mg.

Attenuation of Cocaine-Seeking Behavior in Rats after a Period of Extinguishment Blockade of the CB1 receptor with antagonists/inverse agonists SR141716A and AM251 has been demonstrated to reduce intake of palatable food, self-administration of several drugs of abuse, and reinstatement of food and drug-seeking behaviors. See, Carai, M. A.; Colombo, G.; Gessa, G. L. Rimonabant: the first therapeutically relevant cannabinoid antagonist. *Life Sci* 2005, 77, 2339-50; De Vries, T. J.;

Shaham, Y.; Homberg, J. R.; Crombag, H.; Schuurman, K.; Dieben, J.; Vanderschuren, L. J.; Schoffelmeer, A. N. A cannabinoid mechanism in relapse to cocaine seeking. *Nat Med* 2001, 7, 1151-4; and Fattore, L.; Spano, S.; Cossu, G.; Deiana, S.; Fadda, P.; Fratta, W. Cannabinoid CB(1) antagonist SR 141716A attenuates reinstatement of heroin self-administration in heroin-abstinent rats. *Neuropharmacology* 2005, 48, 1097-104; each incorporated herein with regard to such testing.

Compounds of the present invention were tested to determine if they would achieve the same effects in vivo.

Figure 2:
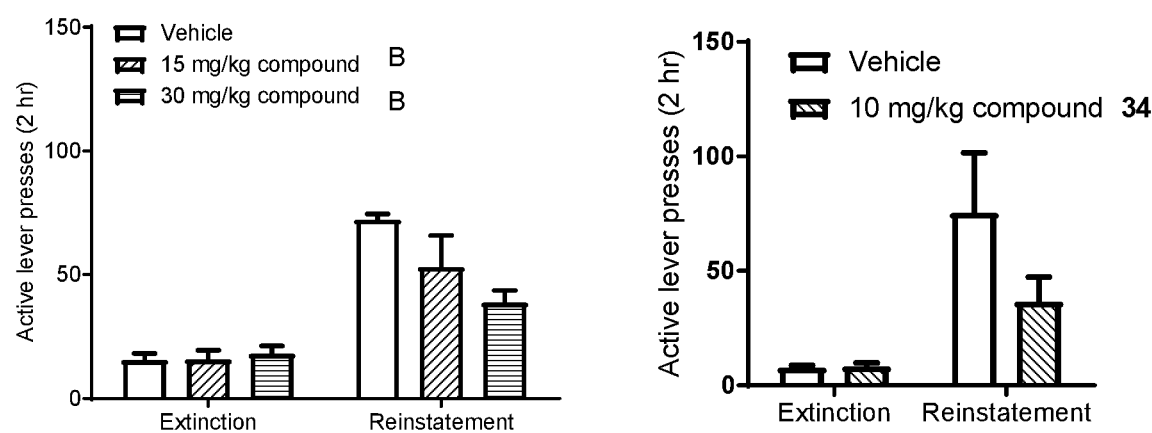
FIG. 2 is a graphical illustration demonstrating that Compounds B and 34 attenuated the resumption of extinguished cocaine-seeking behavior in rats.

As shown in FIG. 2, cocaine prime significantly reinstated the extinguished active lever response (t test: t[7]=16.29, p<0.0001). Pretreatment with B dose-dependently attenuated cocaine-induced reinstatement of cocaine-seeking behavior (one way ANOVA: F[2, 22]=5.174, p<0.05). Post hoc analysis revealed that at the dose of 30 mg/kg, B significantly reduced cocaine-induced reinstatement behavior. Excitingly, 34 at 10 mg/kg produced the same degree of attenuation as that of 30 mg/kg of B (t test: t[20]=1.24, p<0.05). Thus, 34, like B, demonstrated in vivo antagonist effects as expected for CB1 NAMs, but with greater potency. As B and 34 had equivalent in vitro $IC_{50}$ values in both calcium mobilization and [$^{35}S$]GTP-γ-S binding assays, the difference in in vivo potency is likely due to the improved of metabolic stability of 34 which was capable of reaching the sites of action in CNS at higher concentrations.

The endocannabinoid system, particularly the CB1 receptor, has shown promising potential as a therapeutic target in a number of neuropsychiatric disorders such as mood disorders and drug addiction.[34] Many CB1 antagonists/inverse agonists have been reported but the inherent untoward effects of these ligands limit their development to become drug candidates. The present study describes a series of novel diarylureas as an alternate approach to manipulate this important signaling pathway while circumventing side effects of orthosteric ligands.

The present diarylureas provide comparable or even great potency as determined in calcium mobilization and [$^{35}S$] GTP-γ-S binding assays. In particular, compound 34 provides similar in vitro potency but significantly improved microsomal stability. The compounds of the present invention are effective in attenuating the tendency of rats to resume cocaine taking after a period of extinction. In this model, the optimized analog 34 appeared more potent than the standard compound B, possibly resulting from its improved metabolic stability.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A compound of Formula (I):

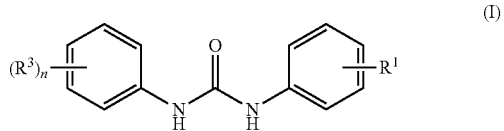

wherein:
$R^2$ is $C_{1-6}$ alkyl, $C_{1-6}$ alkoxy, halogen, or $C_{1-6}$ haloalkyl;
$R^3$ is H, $C_{1-6}$ alkyl, $C_{1-6}$ alkenyl, $C_{1-6}$ alkynyl, halogen, $C_{1-6}$ haloalkyl, $NO_2$, or CN; and
n is 1, 2, or 3;
or a pharmaceutically acceptable salt or solvate thereof.

2. The compound of claim 1, wherein n is 1.

3. The compound of claim 1, wherein $R^3$ is halogen or cyano.

4. The compound of claim 1, wherein $R^3$ is Cl.

5. The compound of claim 1, wherein $R^2$ is halogen.

6. A method for inhibiting the CB1 receptor comprising administering an effective amount of a compound of claim 1 to a patient in need thereof, wherein the patient suffers from a CB1 receptor mediated disorder selected from one or more of substance withdrawal, drug dependence, smoking cessation, opioid addiction, cocaine addiction, relapse of cocaine addiction, tobacco addiction, alcohol addiction, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, chronic pain, acute pain, somatic pain, visceral pain, neuropathic pain, inflammatory pain, infertility, memory loss, cognitive dysfunction, Alzheimer's Disease, Tourette's Syndrome, dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss.

7. The method of claim 6, wherein the disorder is selected from the group consisting of:
(a) substance withdrawal, drug dependence, smoking cessation, opioid addiction, cocaine addiction, tobacco addiction, alcohol addiction, and relapse of addiction;
(b) endometrial cancer, hepatocellular carcinoma, ovarian cancer, breast cancer, pancreatic cancer, colorectal cancer, lung cancer, prostate cancer, desmotrophic small round cell tumors, and renal cell carcinoma;
(c) infertility;
(d) hypercholesterolemia, dyslipidemia, diabetes, gastrointestinal disorders, intestinal hypomotility, obesity, appetite behavior, and weight loss; and
(e) retinopathy and glaucoma.

8. A pharmaceutical compositon comprising a compound of claim 1 and one or more pharmaceutically acceptable carriers.

9. A compound selected from the group consisting of:
3-(4-Chlorophenyl)-1-[3-(4-chlorophenyl)phenyl]urea;
3-(4-Chlorophenyl)-1-[3-(4-fluorophenyl)phenyl]urea;
3-(4-Chlorophenyl)-1-[3-(4-tert-butylphenyl)phenyl] urea;
and pharmaceutically acceptable salts or solvates thereof.

10. A method for inhibiting the CB1 receptor comprising administering an effective amount of a compound of claim 9 to a patient in need thereof, wherein the patient suffers from a CB1 receptor mediated disorder selected from one or more of substance withdrawal, drug dependence, smoking cessation, opioid addiction, cocaine addiction, relapse of cocaine addiction, tobacco addiction, alcohol addiction, endometrial cancer, hepatocellular carcinoma, ovarian cancer, breast cancer, pancreatic cancer, colorectal cancer, lung cancer, prostate cancer, desmotrophic small round cell tumors, and renal cell carcinoma, analgesia, chronic pain, acute pain, somatic pain, visceral pain, neuropathic pain, inflammatory pain, infertility, memory loss, cognitive dysfunction, Alzheimer's Disease, Tourette's Syndrome, dyskinesia, amyotrophic lateral sclerosis, stroke, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, obesity, appetite behavior, or weight loss.

11. The method of claim 10, wherein the disorder is selected from the group consisting of:
   (a) substance withdrawal, drug dependence, smoking cessation, opioid addiction, cocaine addiction, tobacco addiction, alcohol addiction, and relapse of addiction;
   (b) endometrial cancer, hepatocellular carcinoma, ovarian cancer, breast cancer, pancreatic cancer, colorectal cancer, lung cancer, prostate cancer, desmotrophic small round cell tumors, and renal cell carcinoma;
   (c) infertility;
   (d) hypercholesterolemia, dyslipidemia, diabetes, anxiety, gastrointestinal disorders, intestinal hypomotility, obesity, appetite behavior, and weight loss; and
   (e) retinopathy and glaucoma.

12. A pharmaceutical compositon comprising a compound of claim 9 and one or more pharmaceutically acceptable carriers.

13. The compound of claim 9, wherein the compound is 3-(4-Chlorophenyl)-1-[3-(4-fluorophenyl)phenyl]urea or a pharmaceutically acceptable salt or solvate thereof.

14. The compound of claim 1, wherein $R^3$ is halogen.

15. The compound of claim 1, wherein n is 2.

16. The compound of claim 1, wherein n is 3.

17. The compound of claim 1, wherein $R^2$ is $C_{1-6}$ alkyl or $C_{1-6}$ alkoxy.

18. The compound of claim 1, wherein $R^2$ is $C_{1-6}$ haloalkyl.

19. The compound of claim 1, wherein $R^2$ is fluorine.

20. The compound of claim 19, wherein $R^3$ is halogen.

21. The compound of claim 19, wherein $R^3$ is chlorine.

22. The compound of claim 21, wherein n is 1.

23. The pharmaceutical composition of claim 12, wherein the compound is 3-(4-Chlorophenyl)-1-[3-(4-fluorophenyl)phenyl]urea or a pharmaceutically acceptable salt or solvate thereof.

24. The method of claim 6, wherein the disorder is selected from the group consisting of substance withdrawal, drug dependence, smoking cessation, opioid addiction, cocaine addiction, tobacco addiction, alcohol addiction, and relapse of addiction.

25. The method of claim 10, wherein the disorder is selected from the group consisting of substance withdrawal, drug dependence, smoking cessation, opioid addiction, cocaine addiction, tobacco addiction, alcohol addiction, and relapse of addiction.

* * * * *

UNITED STATES PATENT AND TRADEMARK OFFICE
CERTIFICATE OF CORRECTION

PATENT NO. : 11,084,781 B2
APPLICATION NO. : 16/612680
DATED : August 10, 2021
INVENTOR(S) : Zhang et al.

Page 1 of 1

It is certified that error appears in the above-identified patent and that said Letters Patent is hereby corrected as shown below:

In the Claims

In Column 62, Line 3, please amend Claim 1 as follows:
1. A compound of Formula (I):

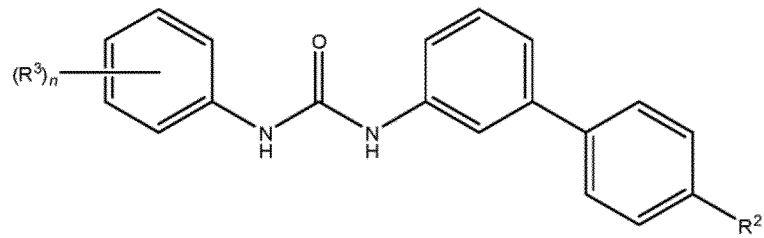

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*